US012559505B2

(12) United States Patent
Xie et al.

(10) Patent No.: US 12,559,505 B2
(45) Date of Patent: Feb. 24, 2026

(54) IDH MUTANT INHIBITOR AND USE THEREOF

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 679 days.

(21) Appl. No.: 17/922,345

(22) PCT Filed: Jun. 28, 2021

(86) PCT No.: PCT/CN2021/102623
§ 371 (c)(1),
(2) Date: Oct. 28, 2022

(87) PCT Pub. No.: WO2022/001916
PCT Pub. Date: Jan. 6, 2022

(65) Prior Publication Data

US 2023/0174550 A1 Jun. 8, 2023

(30) Foreign Application Priority Data

Jun. 28, 2020 (CN) ......................... 202010595326.9
Mar. 22, 2021 (CN) ......................... 202110302649.9

(51) Int. Cl.
*C07D 498/04* (2006.01)
*A61P 35/00* (2006.01)
*C07D 487/04* (2006.01)
*C07D 519/00* (2006.01)

(52) U.S. Cl.
CPC ............ *C07D 498/04* (2013.01); *A61P 35/00* (2018.01); *C07D 487/04* (2013.01); *C07D 519/00* (2013.01)

(58) Field of Classification Search
CPC .. C07D 498/04; C07D 487/04; C07D 519/00; A61P 35/00; A61K 31/5365
See application file for complete search history.

(56) References Cited

U.S. PATENT DOCUMENTS 10,253,041 B2 * 4/2019 Bauer .................. C07D 498/04

FOREIGN PATENT DOCUMENTS

| | | | | |
|---|---|---|---|---|
| CN | 107849059 A | | 3/2018 | |
| CN | 110072867 A | | 7/2019 | |
| CN | 107849059 B | * | 4/2020 | ........... C07D 498/04 |
| WO | 2016171755 A1 | | 10/2016 | |
| WO | 2019224096 A1 | | 11/2019 | |

* cited by examiner

*Primary Examiner* — Kamal A Saeed
*Assistant Examiner* — Meghan C Heasley
(74) *Attorney, Agent, or Firm* — SZDC Law PC

(57) ABSTRACT

The present invention relates to a compound of general formula (1a) or general formula (1b) and a method for preparing the same, and use of the compound of general formula (1a) or general formula (1b) and an isomer, a crystalline form, a pharmaceutically acceptable salt, a hydrate or a solvate thereof as an irreversible inhibitor for an IDH mutant in preparing a medicament for resisting a diseases such as a tumor related to an IDH mutant protein.

(1a)

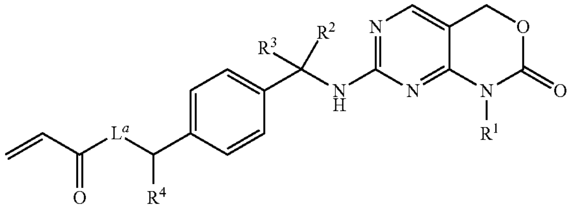

(1b)

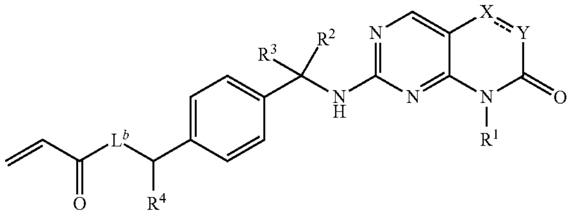

4 Claims, No Drawings

IDH MUTANT INHIBITOR AND USE THEREOF

The present application is the National Stage Application of PCT/CN2021/102623, filed on Jun. 28, 2021, which claims the priority to Chinese Patent Application No. CN202010595326.9 filed on Jun. 28, 2020 and Chinese Patent Application No. CN202110302649.9 filed on Mar. 22, 2021, which are incorporated herein by reference in their entirety.

TECHNICAL FIELD

The present invention relates to the field of pharmaceutical chemistry, and particularly to a novel IDH mutant inhibitor, a method for preparing the same and use of the compound.

BACKGROUND

Isocitrate dehydrogenase (IDH) is an important enzyme involved in the tricarboxylic acid cycle. It catalyzes the conversion of isocitrate to α-ketoglutarate (α-KG), which is the rate-limiting step in the tricarboxylic acid cycle. There are three different isocitrate dehydrogenases in humans, IDH1, IDH2 and IDH3. IDH1 is mainly localized in the cytoplasm and peroxisomes, and IDH2 and IDH3 are mainly distributed in mitochondria.

IDH1 and IDH2 are the most common metabolic genes in the identification of human cancer gene mutations, and IDH mutations are found in low-grade gliomas, secondary malignant gliomas, melanoma, angioimmunoblastic T-cell lymphoma, myeloproliferative tumors, myelodysplastic syndromes (MDSs), and acute myelocytic leukemia (AML). IDH mutation sites in tumor cells are IDH1 Arg132 (R132), IDH2 Arg172 (R172) or IDH2 Arg140 (R140). These mutations result in a loss of functions of the wild-type IDH protein, and instead provide the ability to convert α-KG to a tumorigenic metabolite D-2-hydroxyglutarate (D-2HG). The tumorigenic metabolite 2-HG inhibits DNA or histone demethylases, resulting in hypermethylation of DNA and histone, thereby promoting the development of cancers. IDH inhibitors can reduce the in vivo tumorigenic metabolite D-2HG by inhibiting the activity of protein with IDH1/R132, IDH2/R172 or IDH2/R140 mutation, induce the demethylation of histone H3K9me3, and achieve the effect of inhibiting the development of tumors. Therefore, targeting mutant IDH1 and IDH2 (mIDH1 and mIDH2) may be a promising approach for cancer therapy.

So far, some IDH micromolecule inhibitors have been marketed, such as enasidenib and ivosidenib developed by Agios Pharmaceuticals Inc, both of which are non-covalent inhibitors. Covalent inhibitors of IDH have been reported by Eli Lilly and Company in Patent Nos. WO2017019429, WO2017213910 and WO2018111707, which have better selectivity for mutant IDH1 and IDH2 relative to wild-type IDH1 and IDH2. However, no IDH covalent inhibitors have entered clinical phase, and thus there is a need to study and explore the covalent IDH inhibitors with better activity and better druggability.

SUMMARY

The present invention is intended to provide a compound of general formula (1a) or an isomer, a crystalline form, a pharmaceutically acceptable salt, a hydrate or a solvate thereof:

(1a)

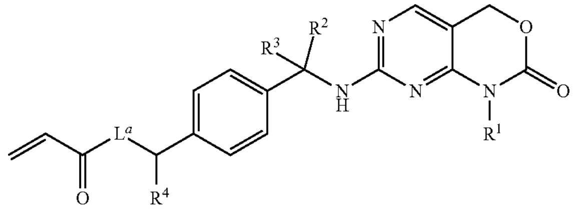

wherein in the general formula (1a):

$L^a$ is the following group:

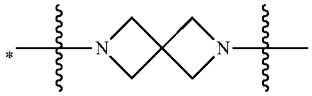
,

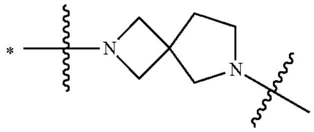
,

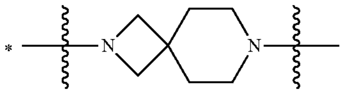
,

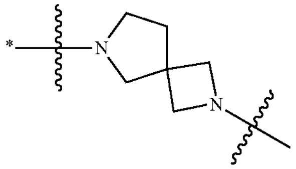
,

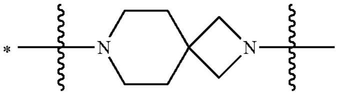
,

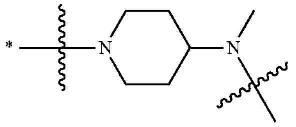
,

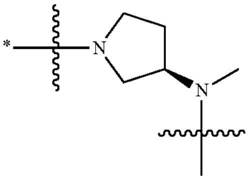
,

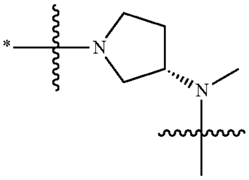
,

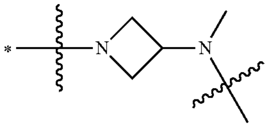
,

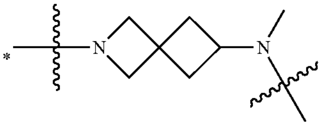
,

-continued

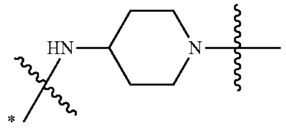,

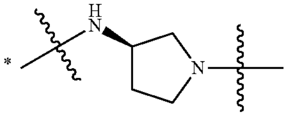,

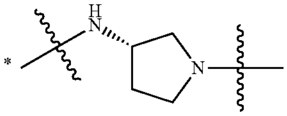,

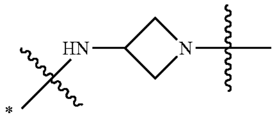,

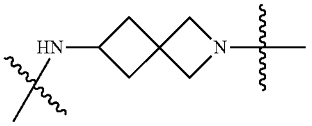,

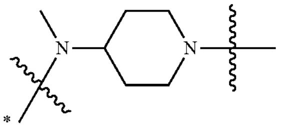,

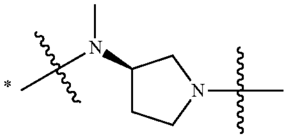,

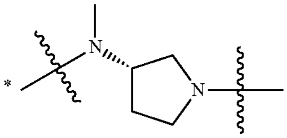,

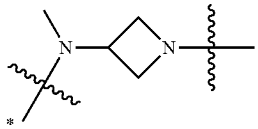 or

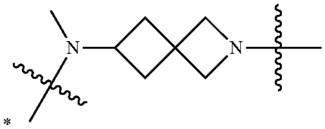, wherein "*" denotes a site linked to a carbonyl group;

$R^1$ is Me, Et, $—CH_2CH_2CH_3$, $—CH(CH_3)_2$,

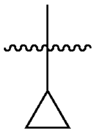, 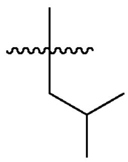 or 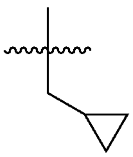;

$R^2$ and $R^3$ are independently H, Me or Et, or $R^2$ and $R^3$, together with the carbon atom, form

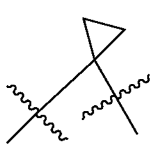 or 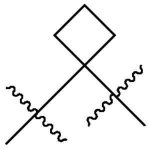;

and $R^4$ is Me, Et, $—CH_2CH_2CH_3$, $—CH(CH_3)_2$, $—CH_2CH(CH_3)_2$,

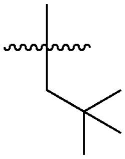, 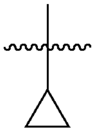, 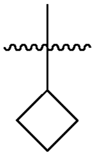, 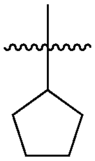, 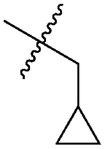, 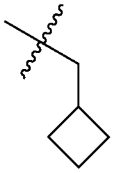, 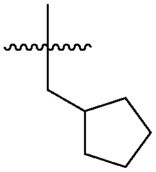, 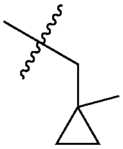, 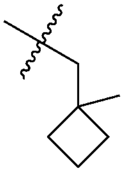, 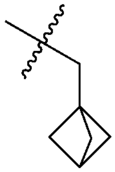, 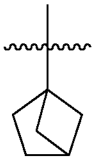, 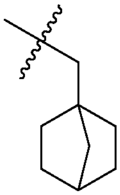 or 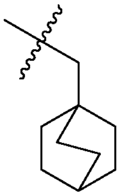.

In another specific embodiment of the present invention, the compound of general formula (1a) has one of the following structures:

1

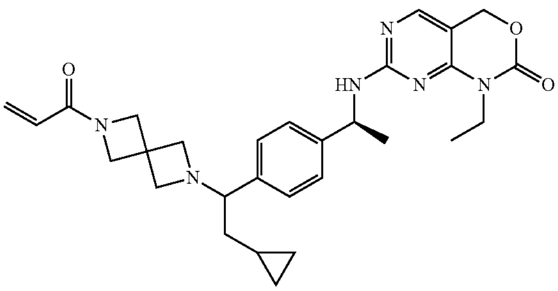

2
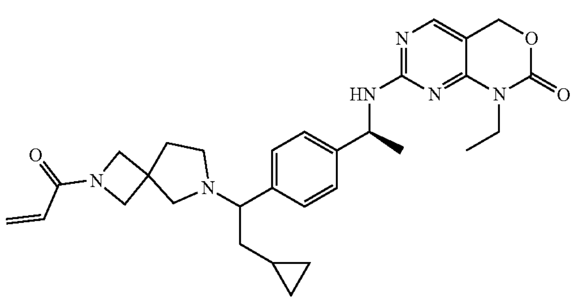
3
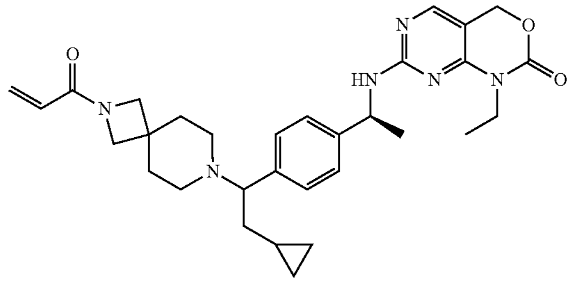
4
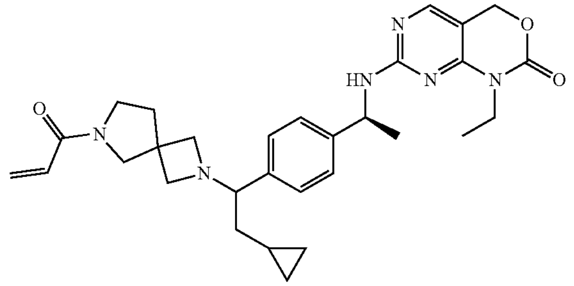
5
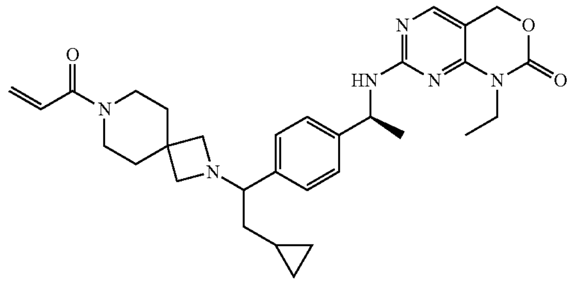
6
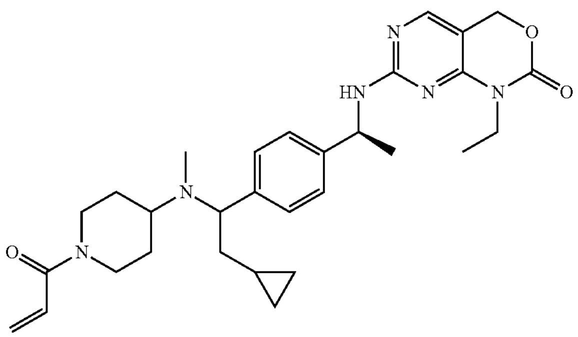
7
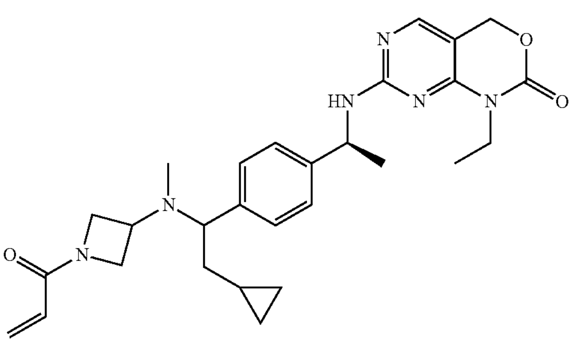
8
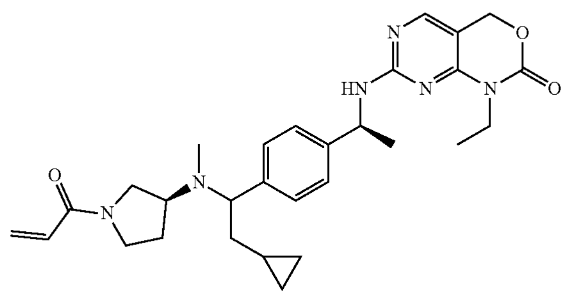
9
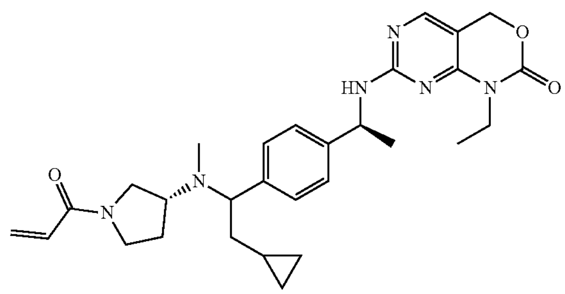
10
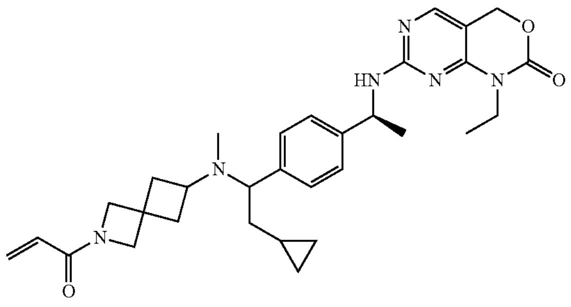
11
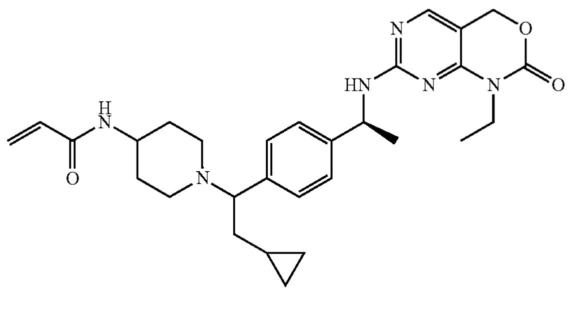

-continued
12
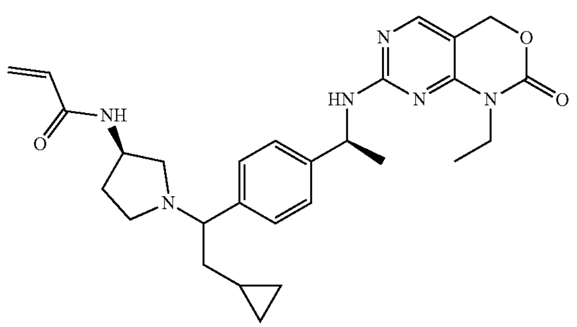
13
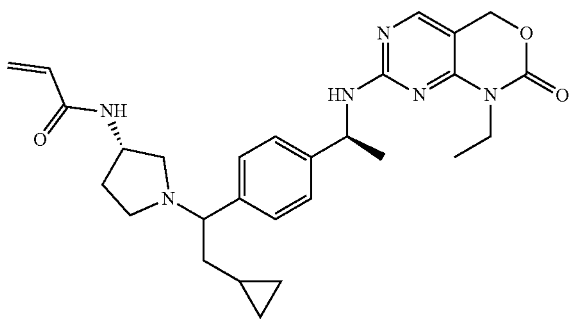
14
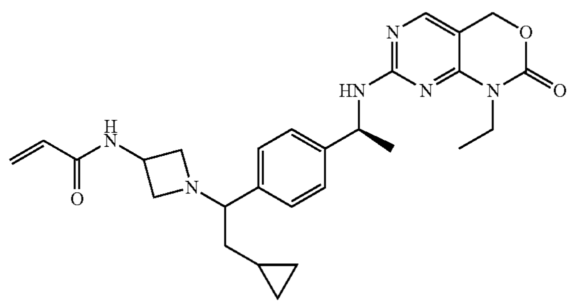
15
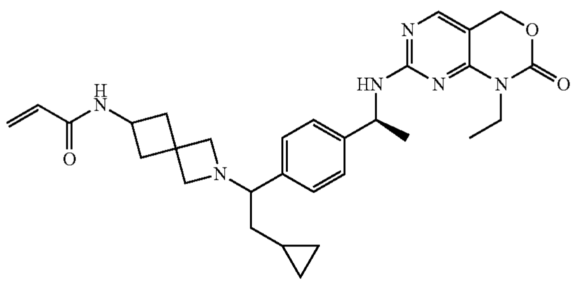
16
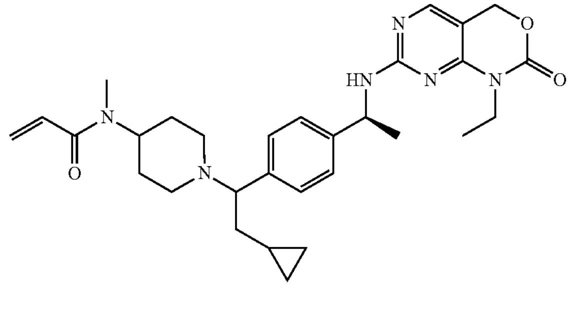
-continued
17
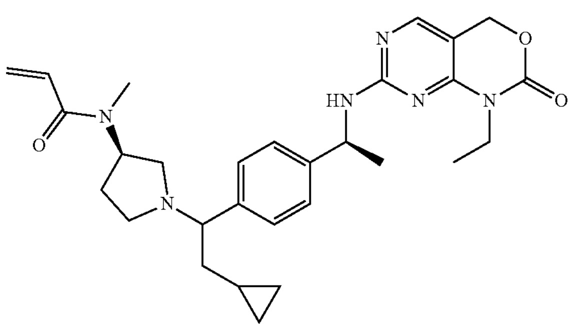
18
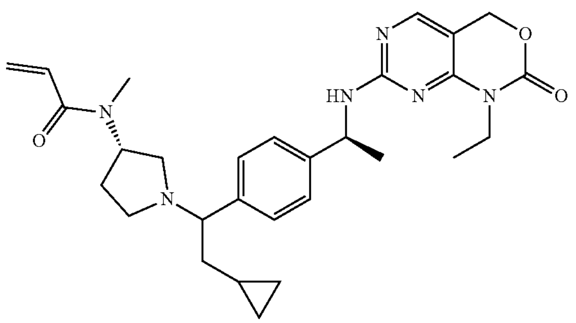
19
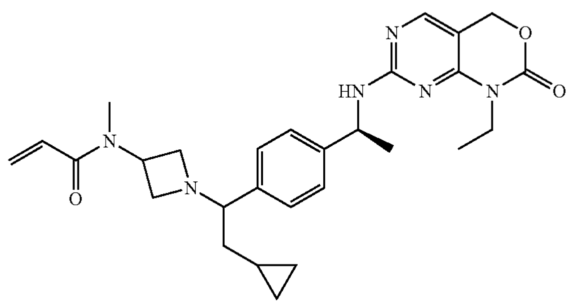
20
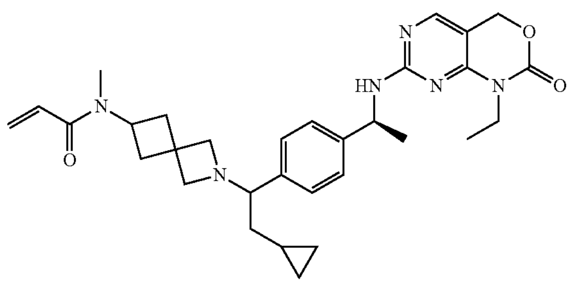
21
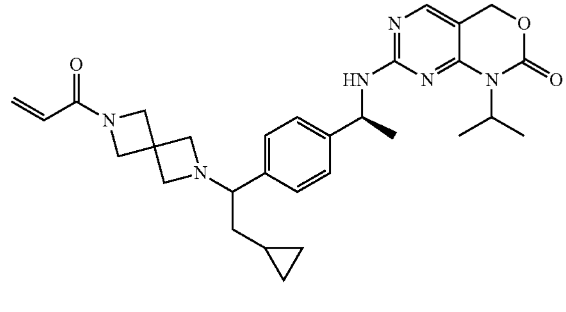

-continued
22
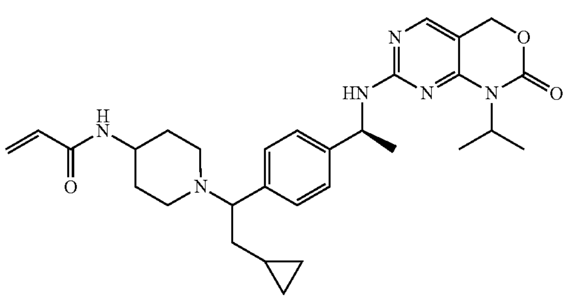
23
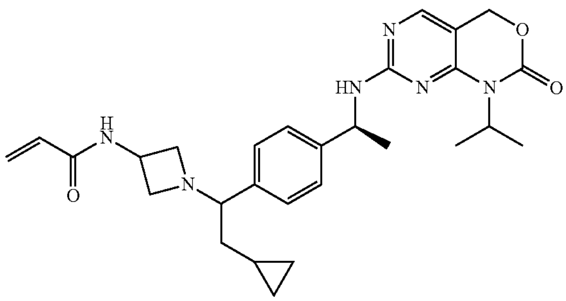
24
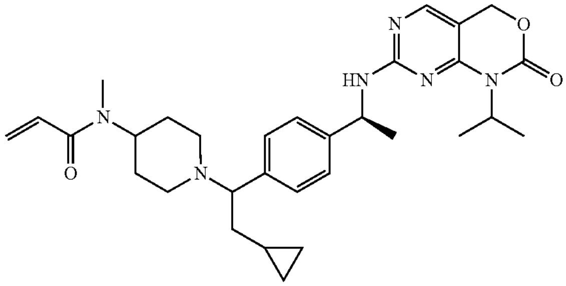
25
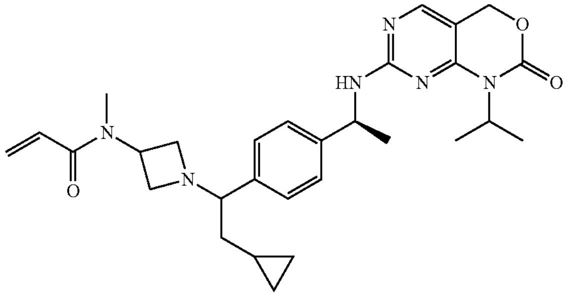
26
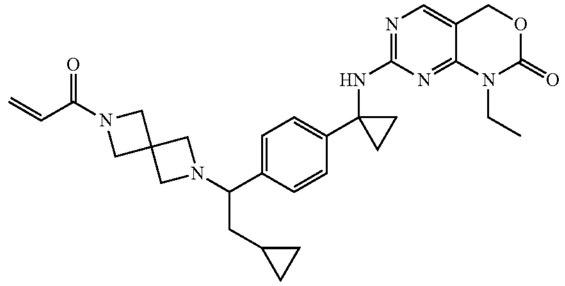
-continued
27
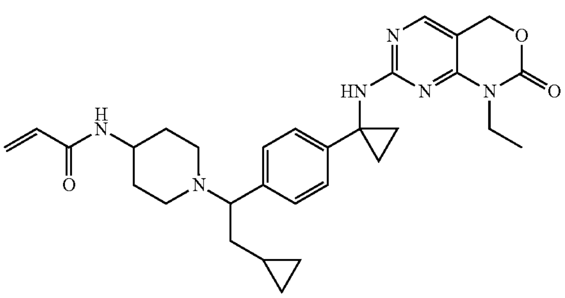
28
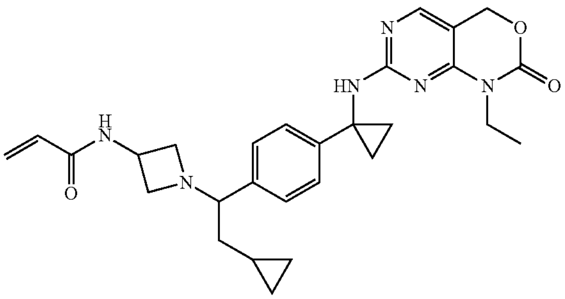
29
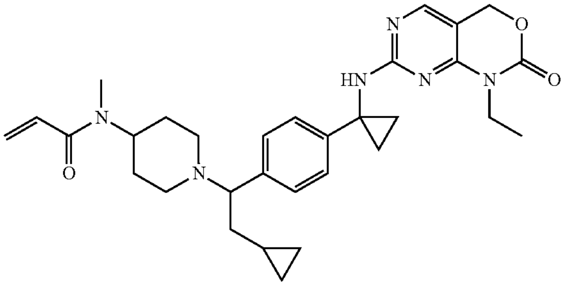
30
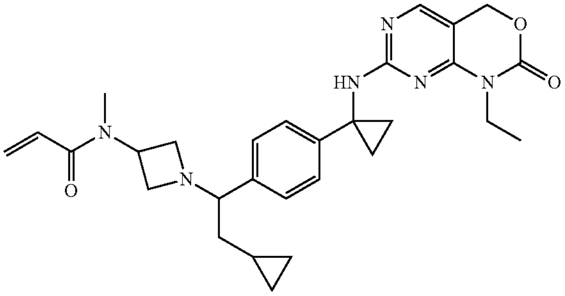
31
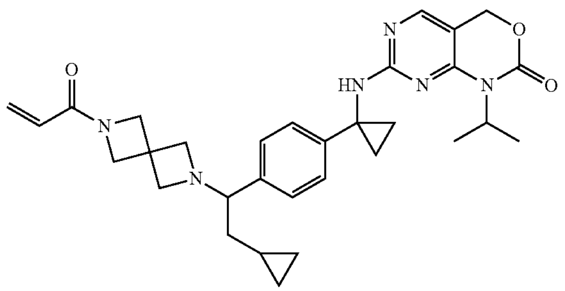

-continued
32
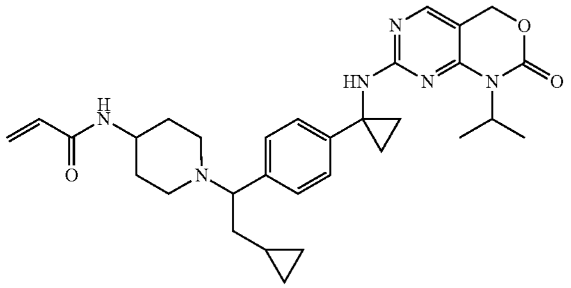
33
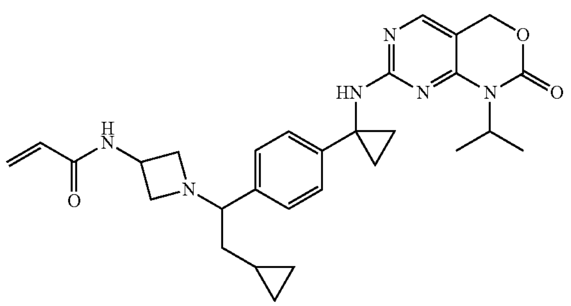
34
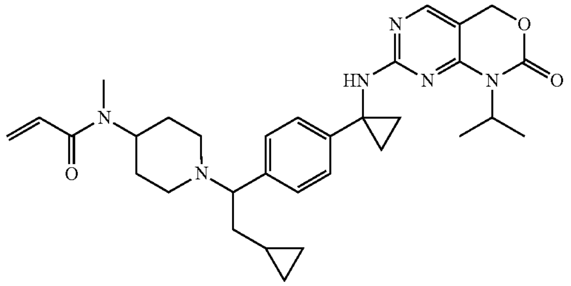
35
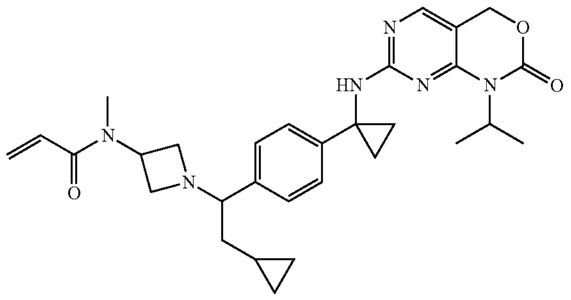
36
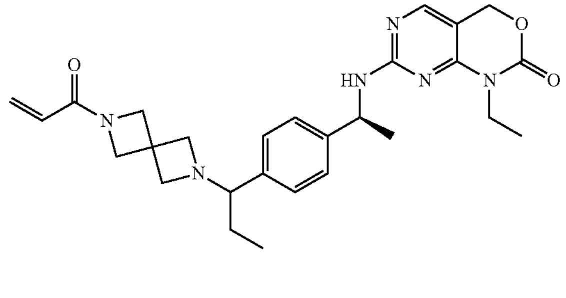
-continued
37
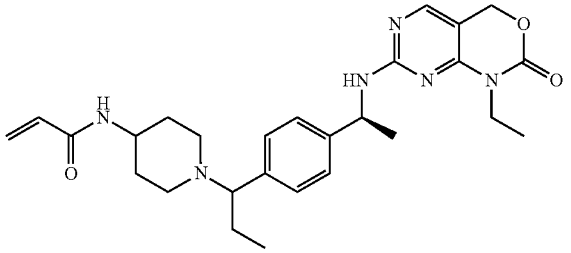
38
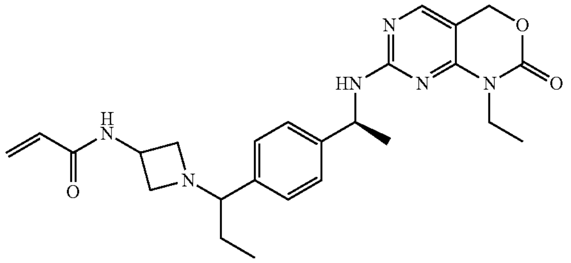
39
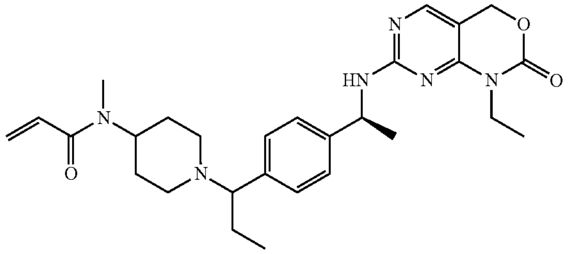
40
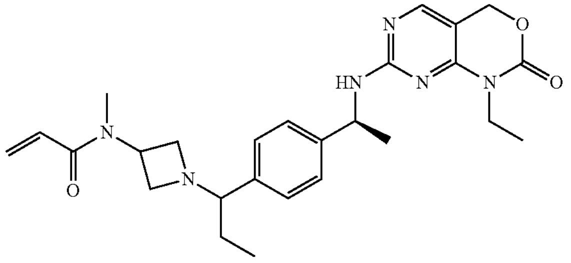
41
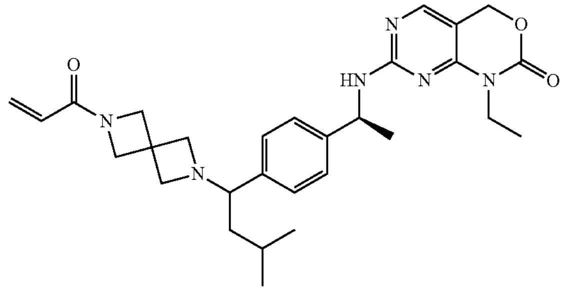

-continued
42
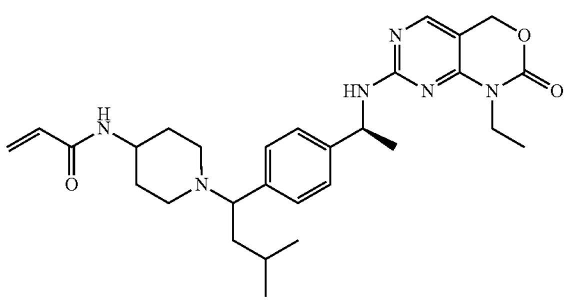
43
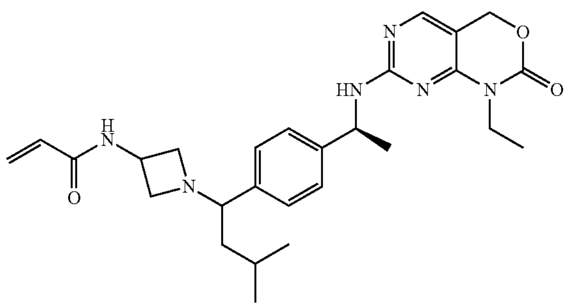
44
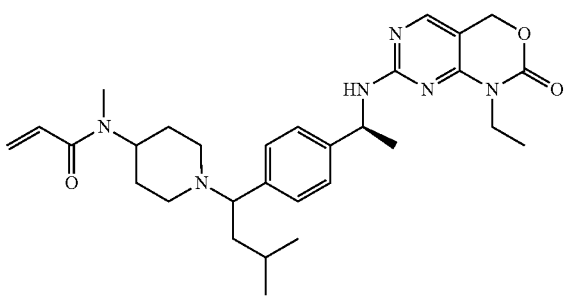
45
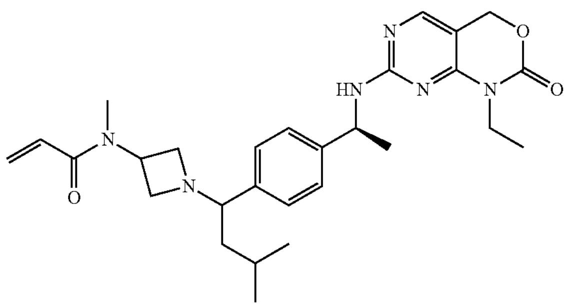
46
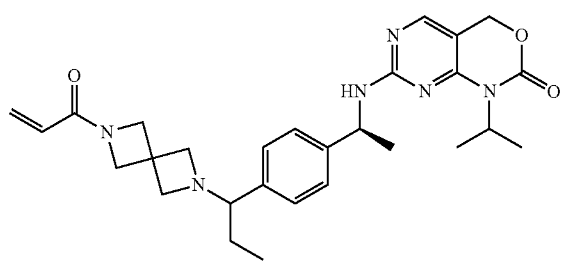
-continued
47
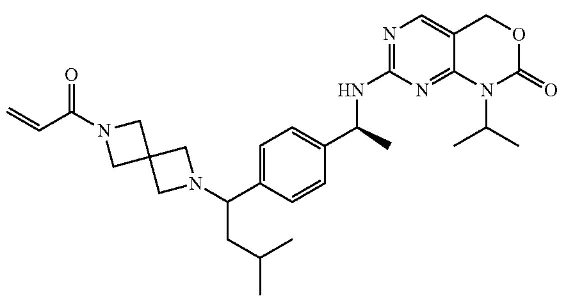
48
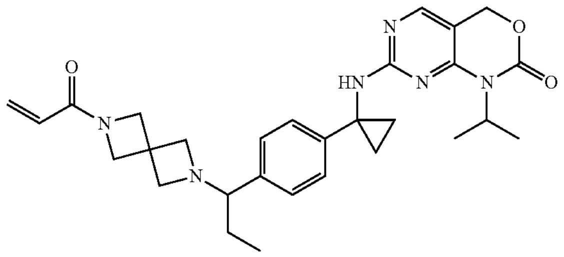
49
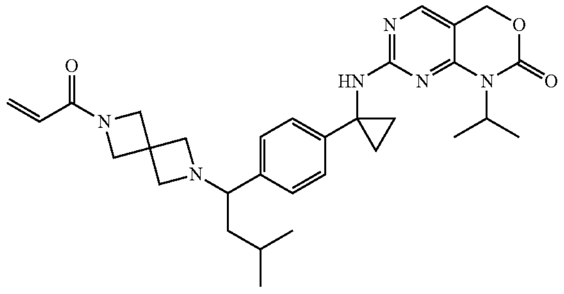
50
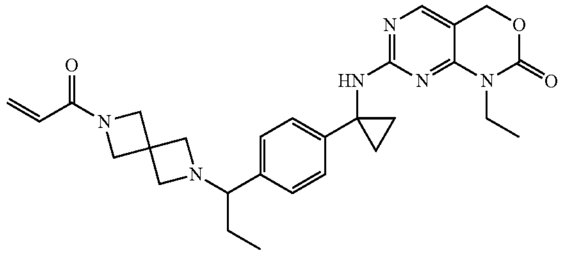
51
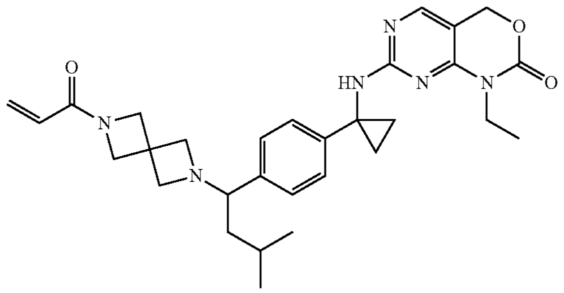

-continued
52
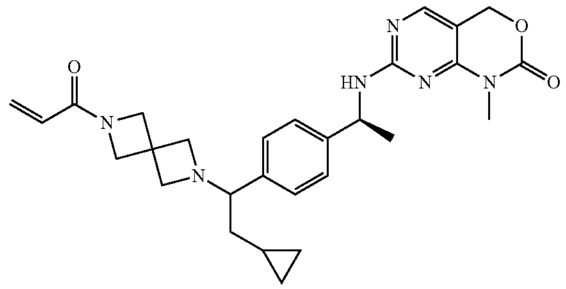
53
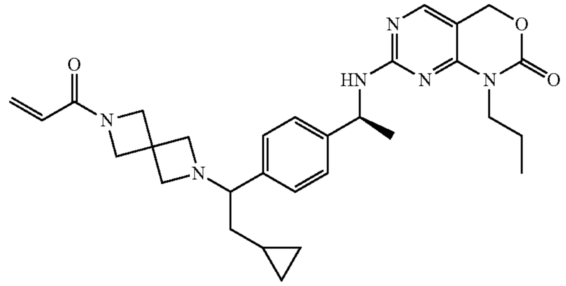
54
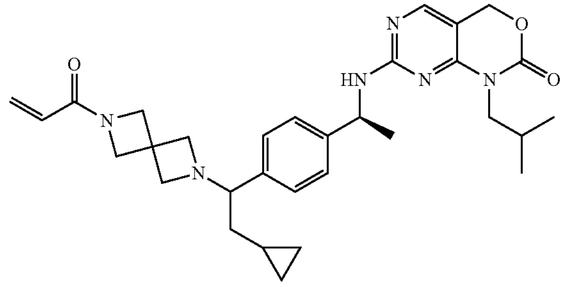
55
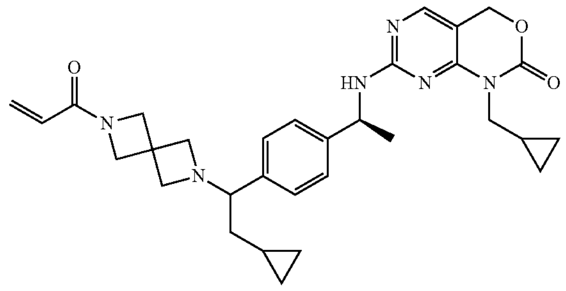
56
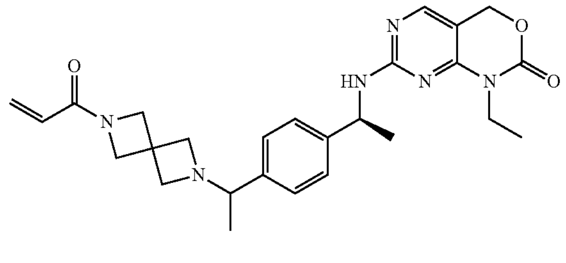
-continued
57
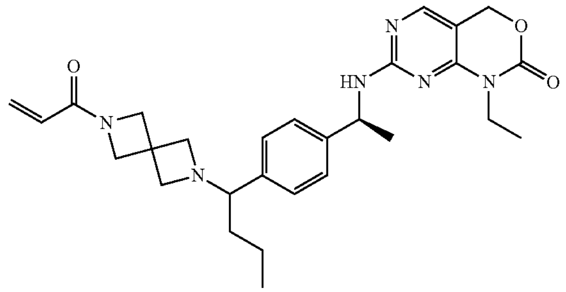
58
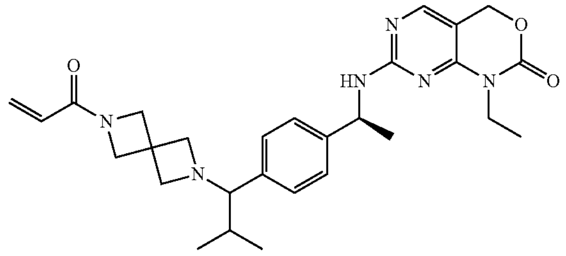
59
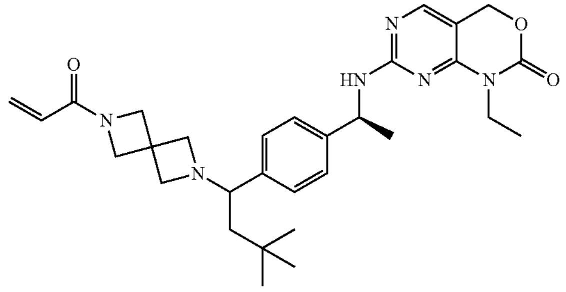
60
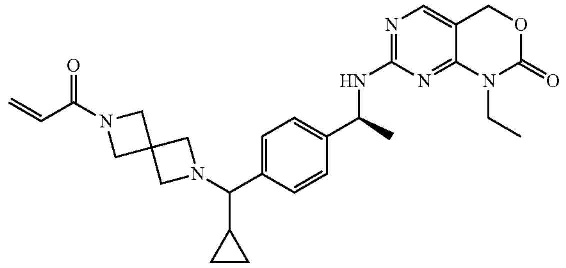
61
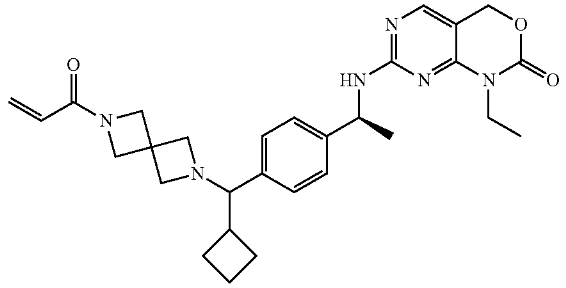

-continued
62
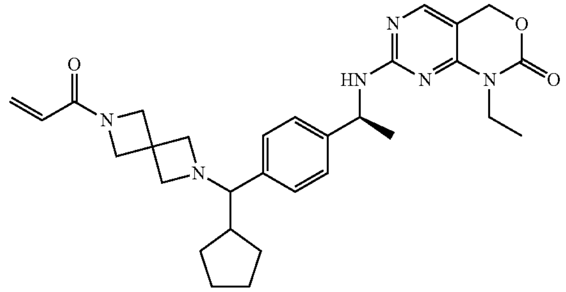
63
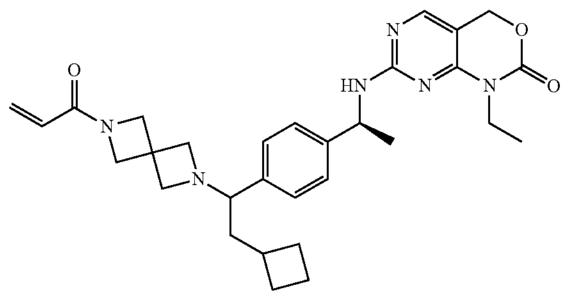
64
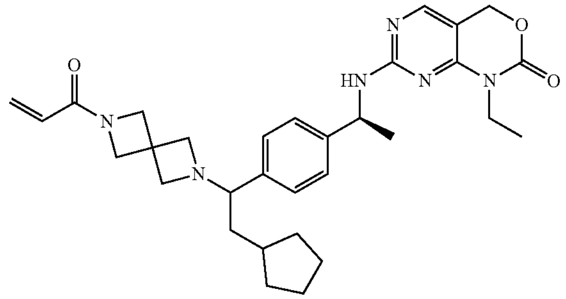
65
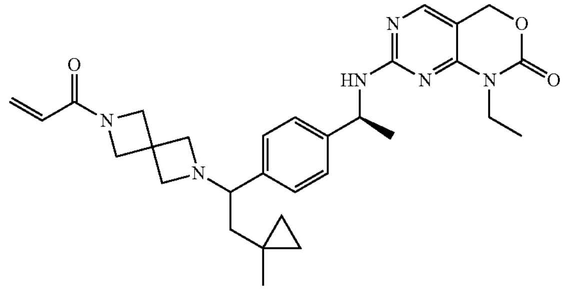
66
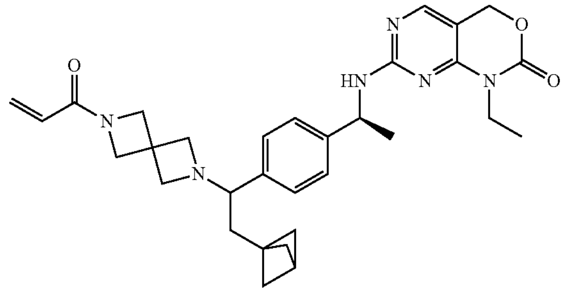
-continued
67
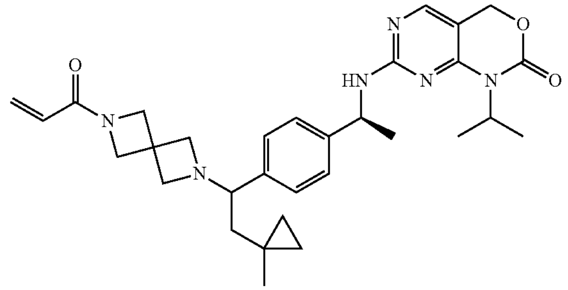
68
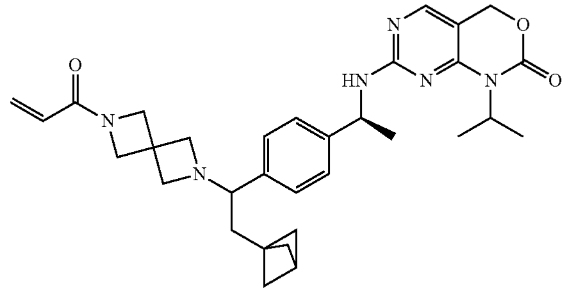
69
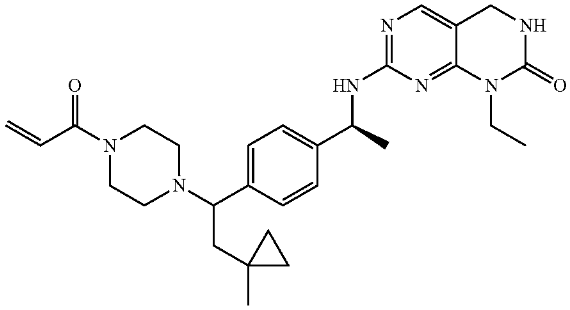
70
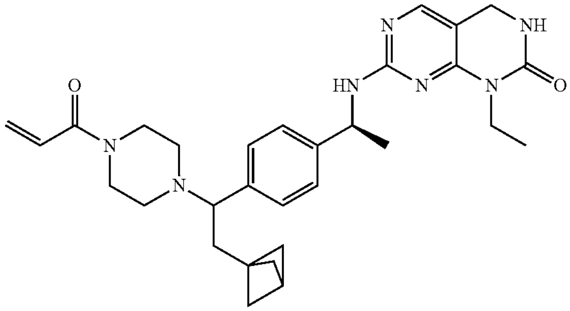
71
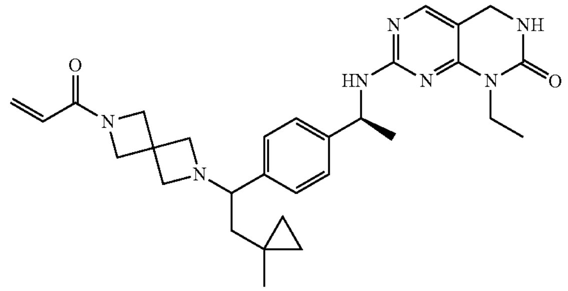

-continued
72
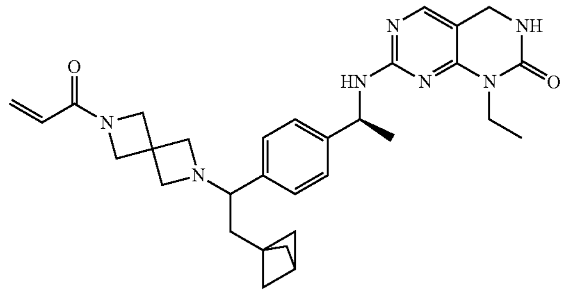
73
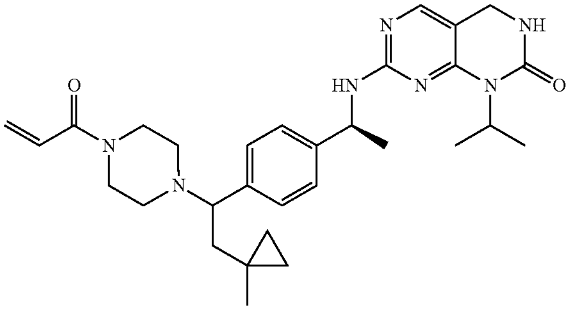
74
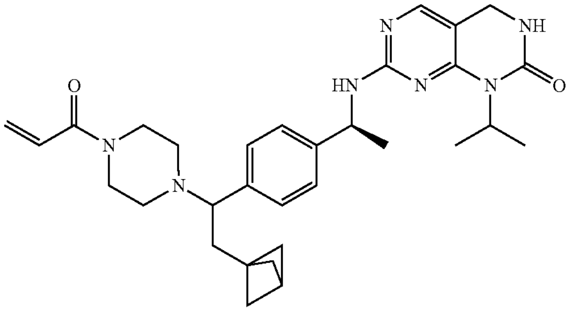
75
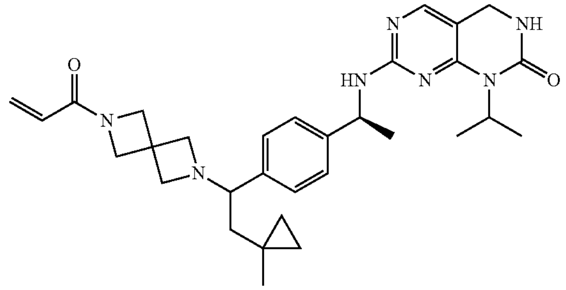
76
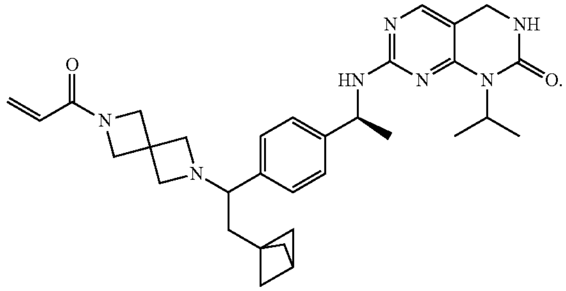
In another aspect, the present invention is intended to provide a compound of general formula (1b) or an isomer, a crystalline form, a pharmaceutically acceptable salt, a hydrate or a solvate thereof:
(1b)
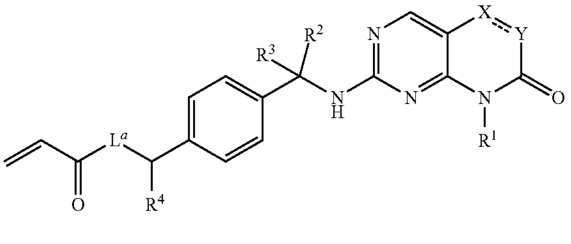
wherein in the general formula (1b):
$L^b$ is the following group:
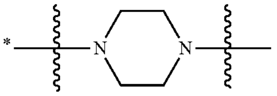
,
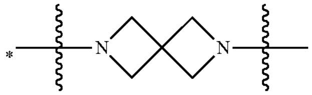
,
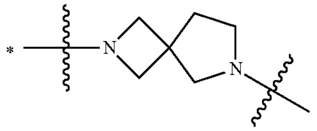
,
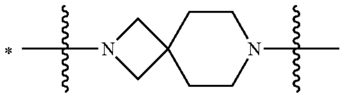
,
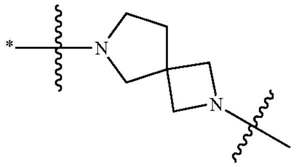
,
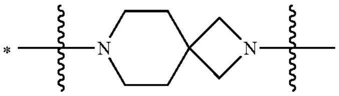
,
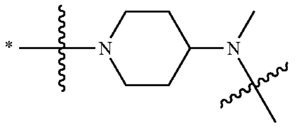
,
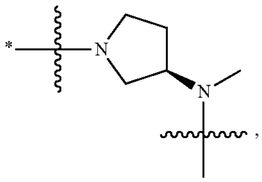
,
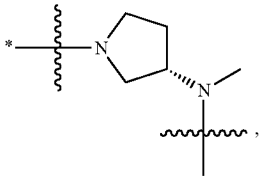
, -continued
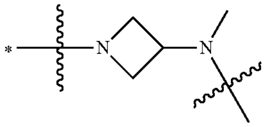
,
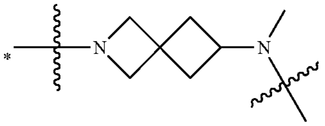
,
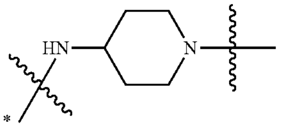
,
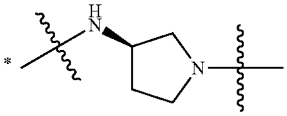
,
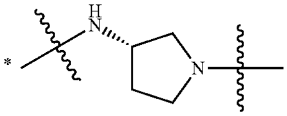
,
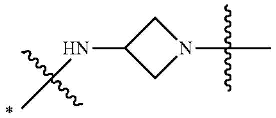
,
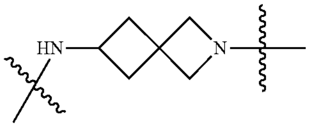
,
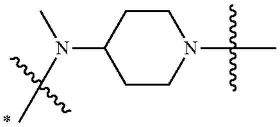
,
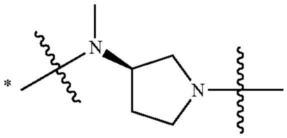
,
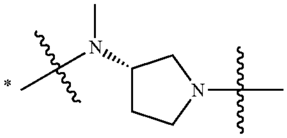
,
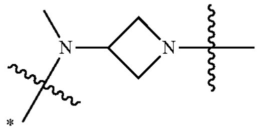
or
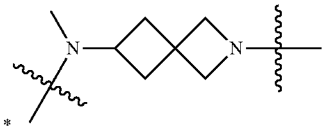
,
wherein "*" denotes a site linked to a carbonyl group;
is the following group:
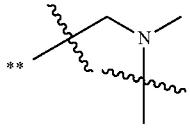
,
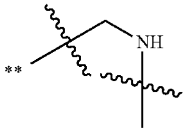
,
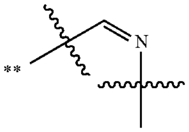
or
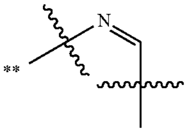
,
wherein "*" denotes the position X terminal;
$R^1$ is Me, Et, $-CH_2CH_2CH_3$, $-CH(CH_3)_2$,
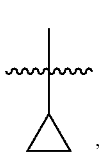
,
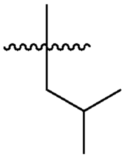
or
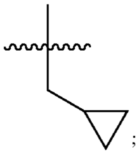
;
$R^2$ and $R^3$ are independently H, Me or Et, or $R^2$ and $R^3$, together with a carbon atom, form
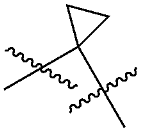
or
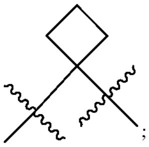
;
and
$R^4$ is Me, Et, $-CH_2CH_2CH_3$, $-CH(CH_3)_2$, $-CH_2CH(CH_3)_2$,
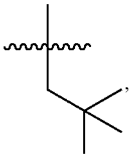
,
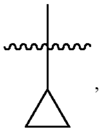
,
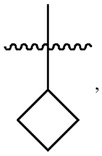
,
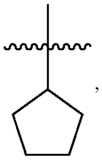
,
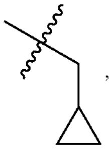
,
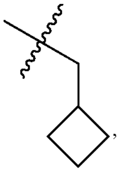
,
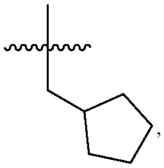
,
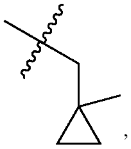
,
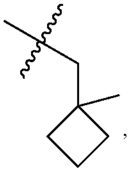
,
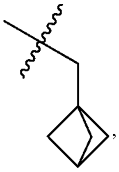
,
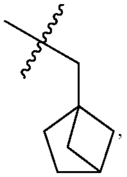
,
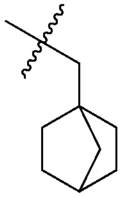
or
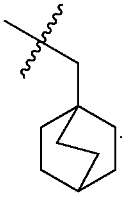
.

In another specific embodiment of the present invention, the compound of general formula (1b) has one of the following structures:
77
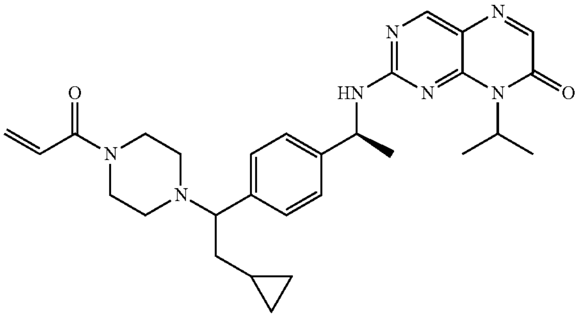
78
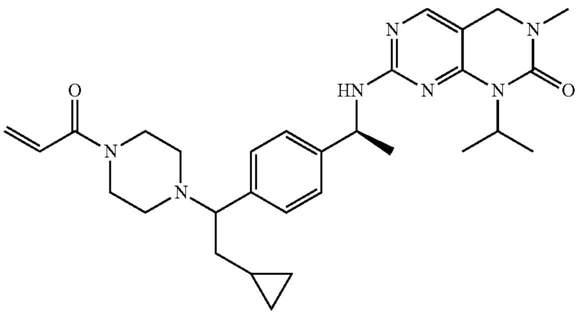
79
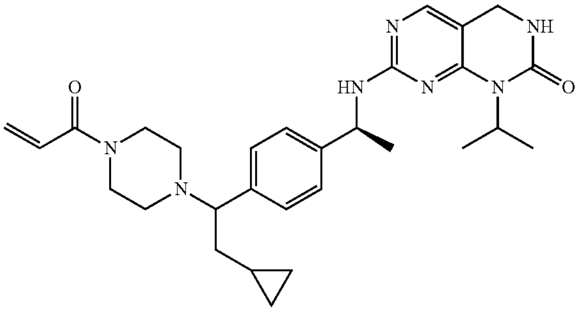
80
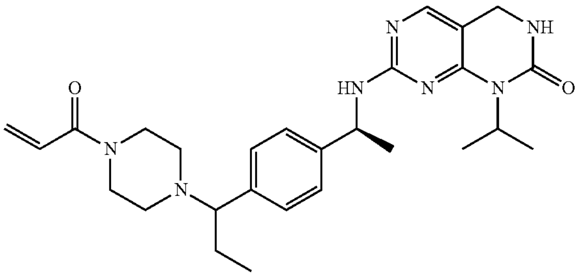
-continued
81
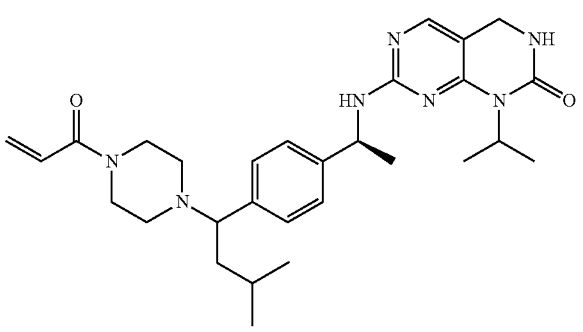
82
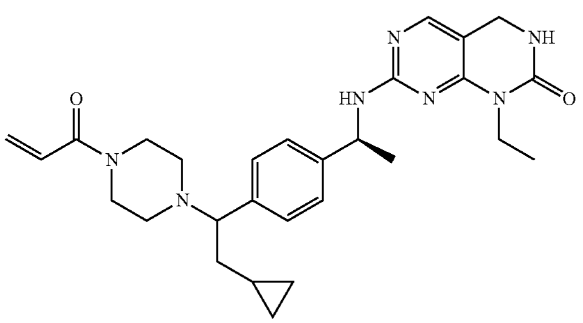
83
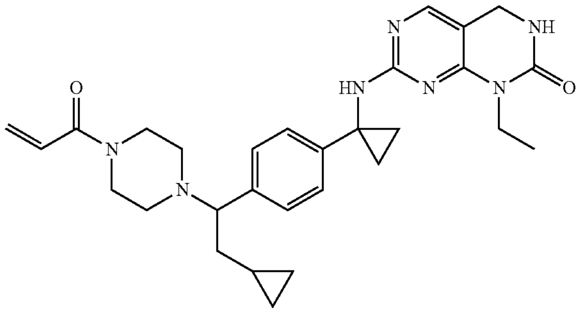
84
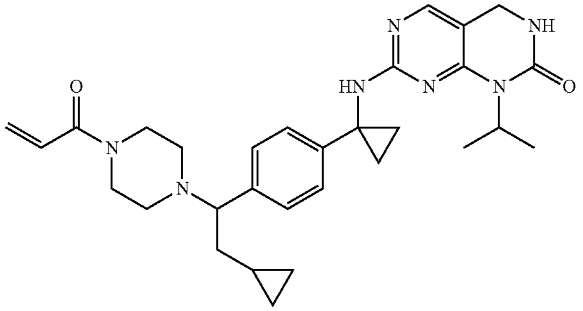

85
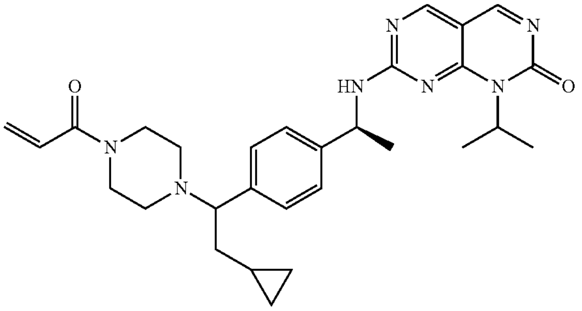
86
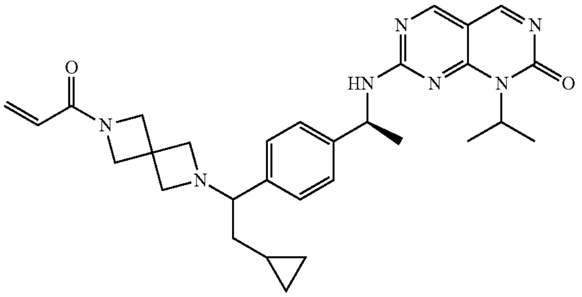
87
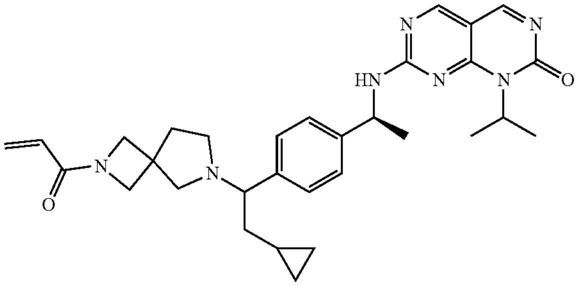
88
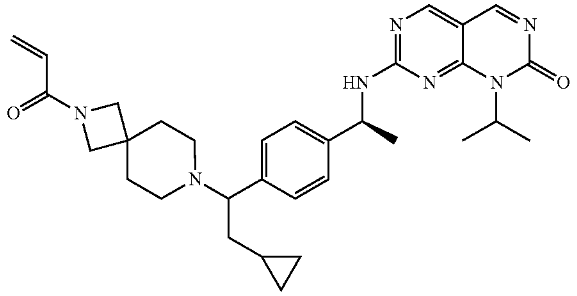
89
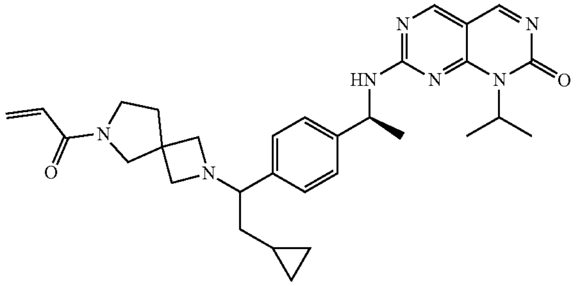
90
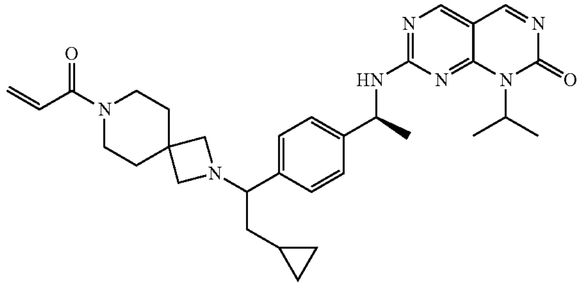
91
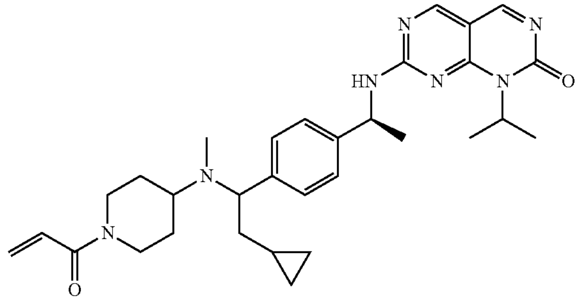
92
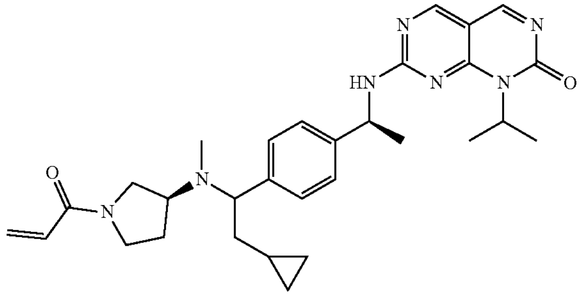
93
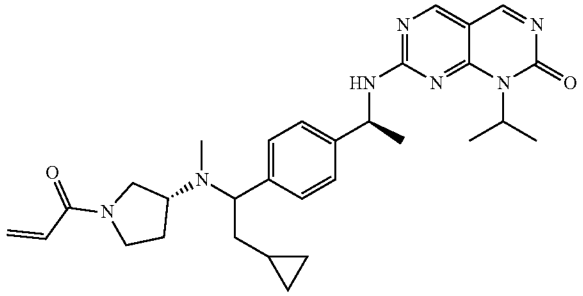
94
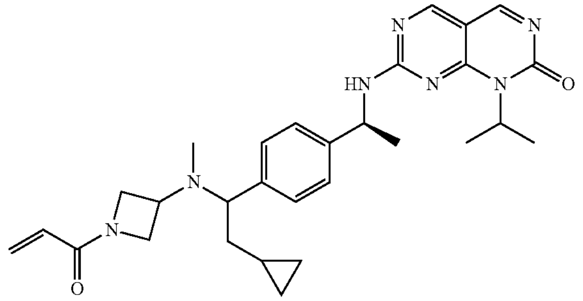

-continued
95
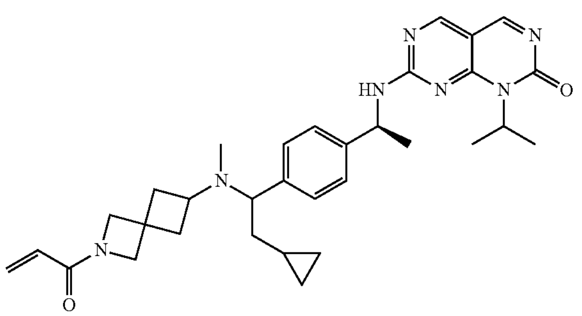
96
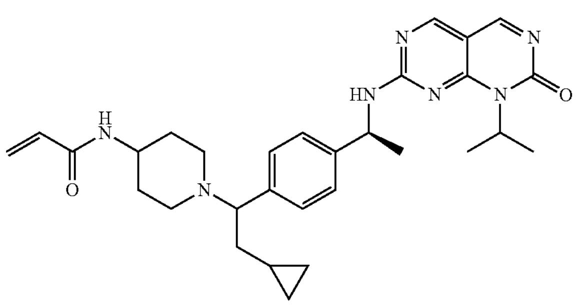
97
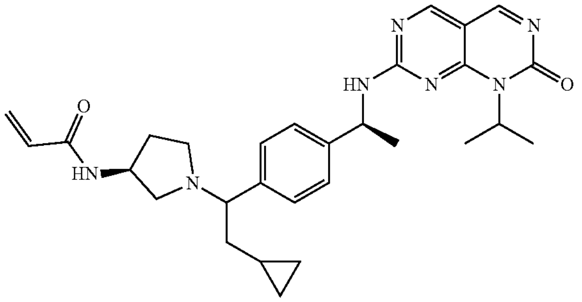
98
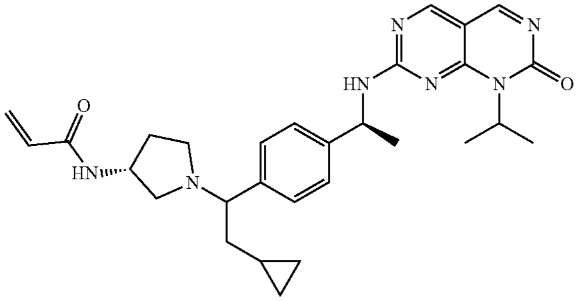
99
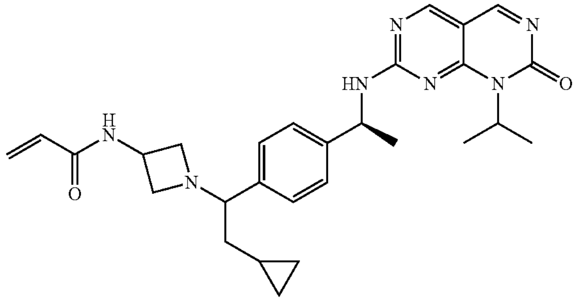
-continued
100
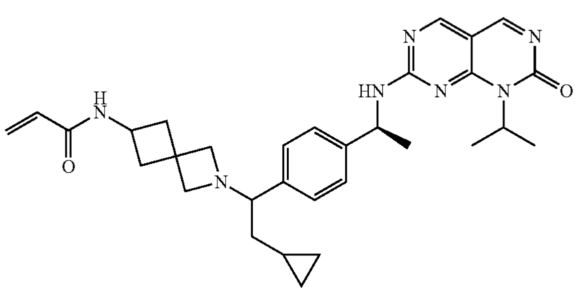
101
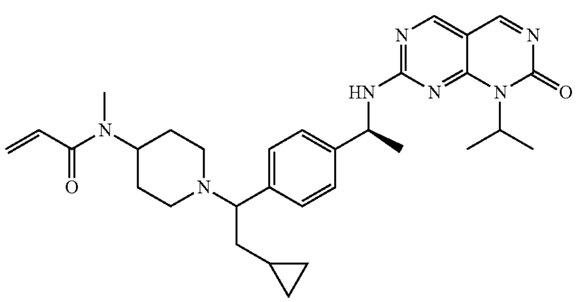
102
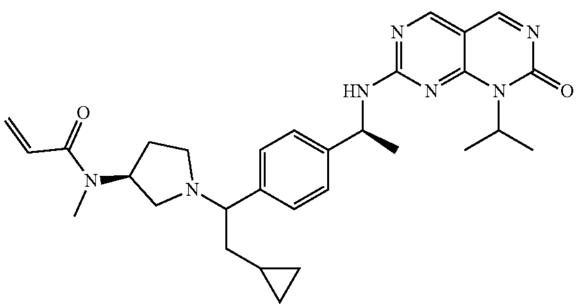
103
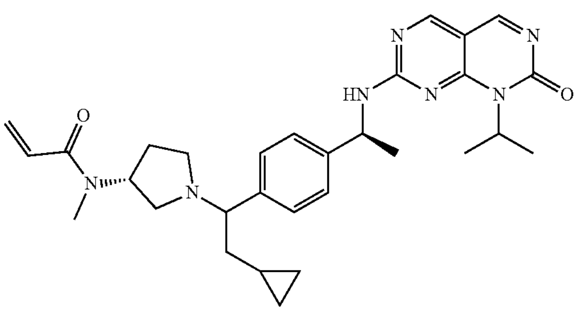
104
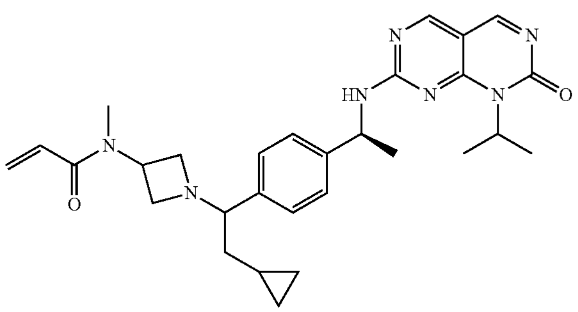

-continued
105
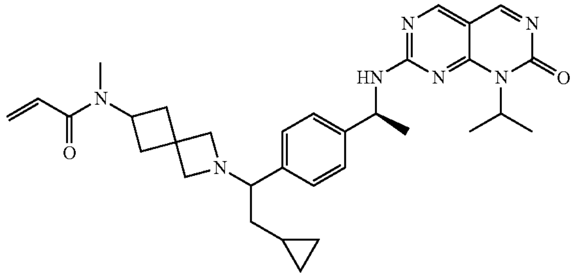
106
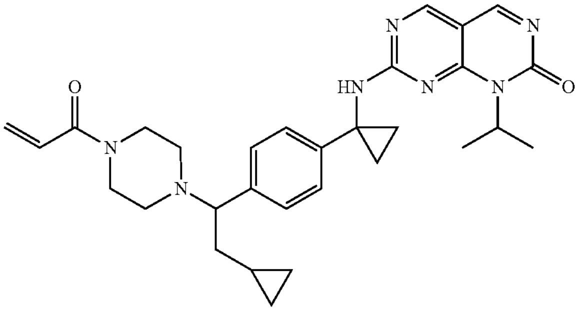
107
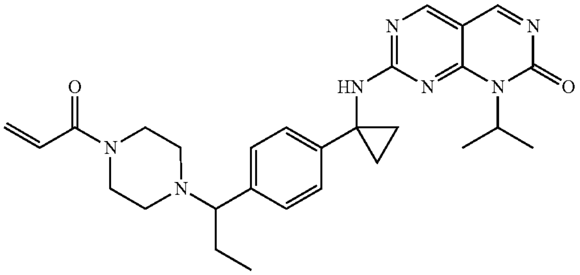
108
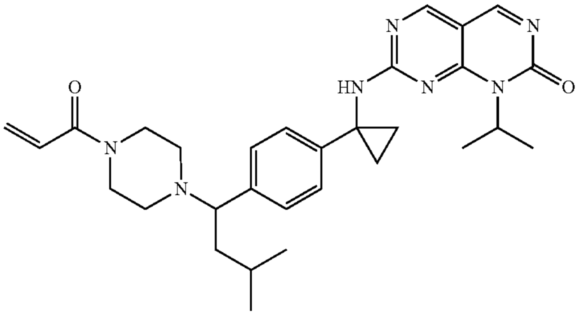
109
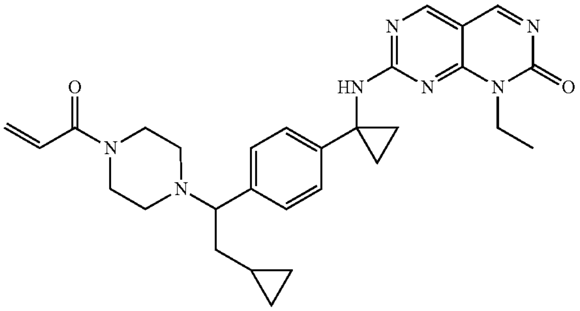
-continued
110
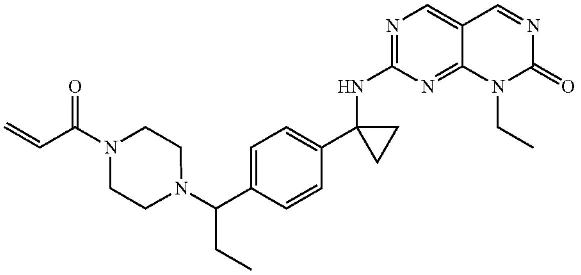
111
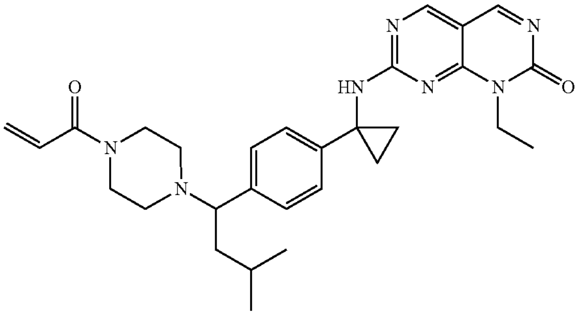
112
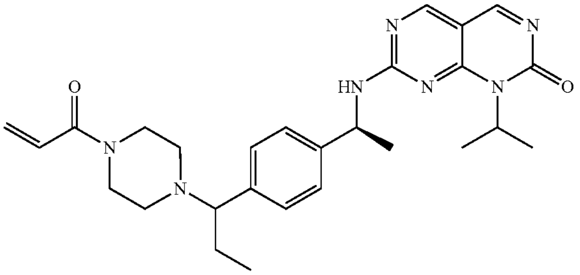
113
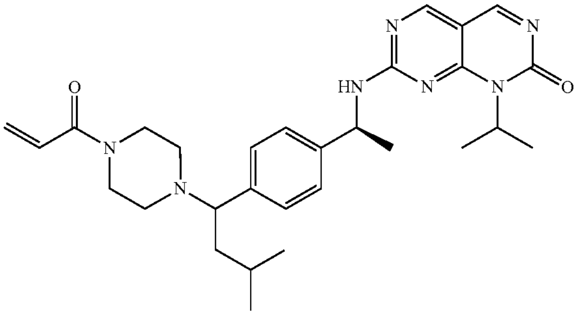
114
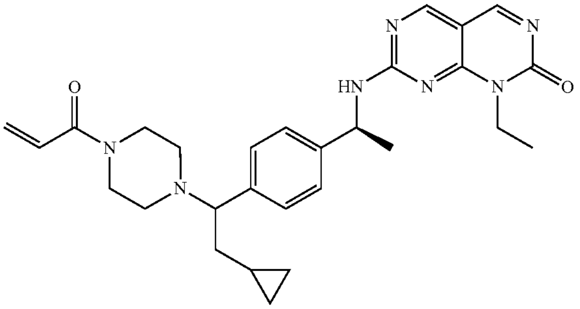

-continued
115
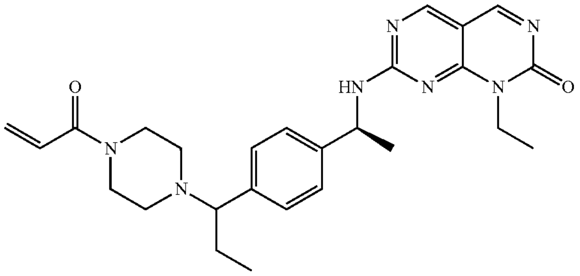
116
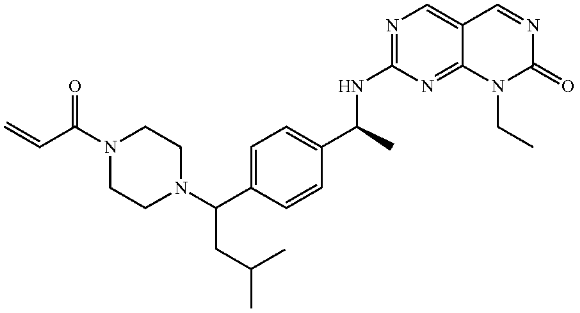
117
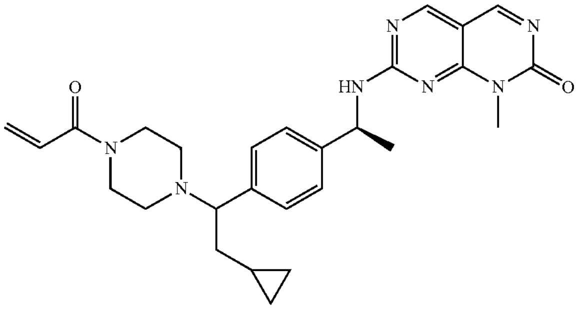
118
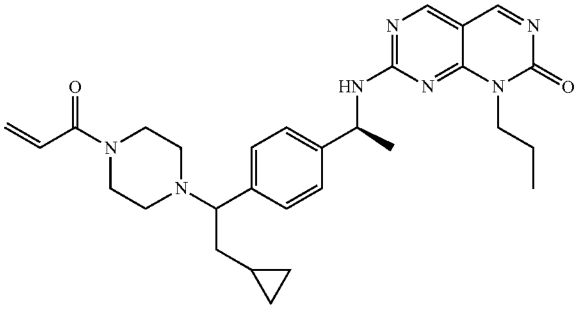
119
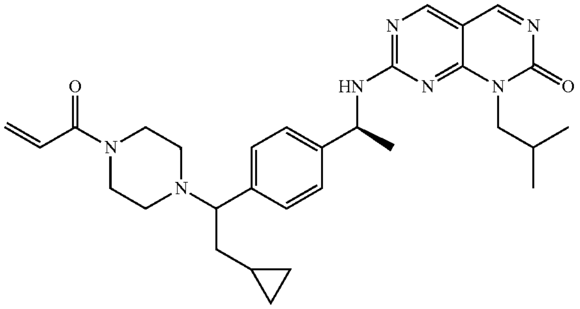
-continued
120
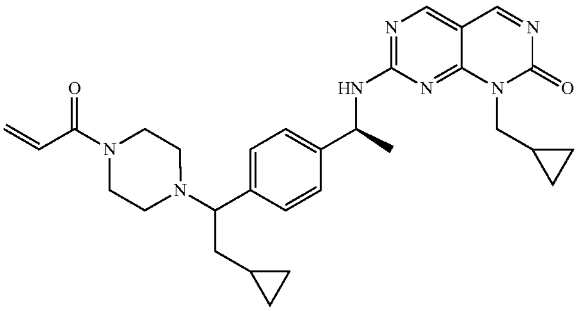
121
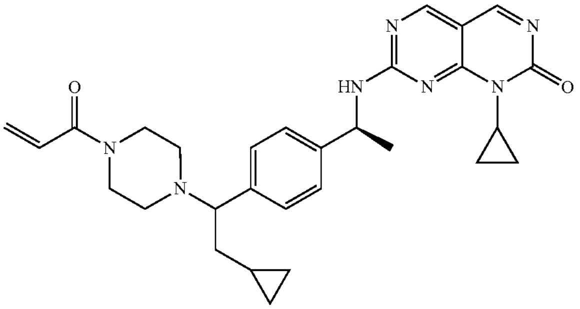
122
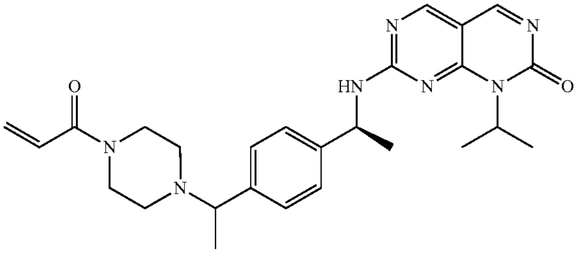
123
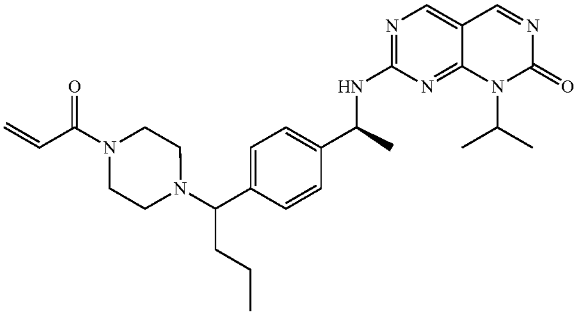
124
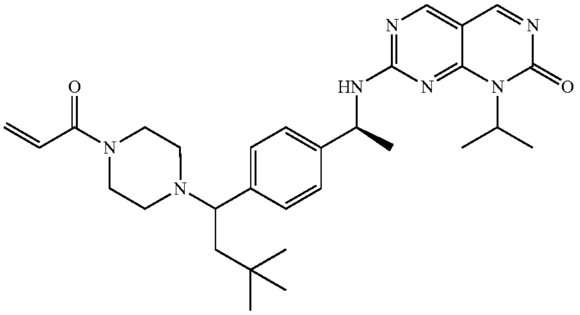

-continued
125
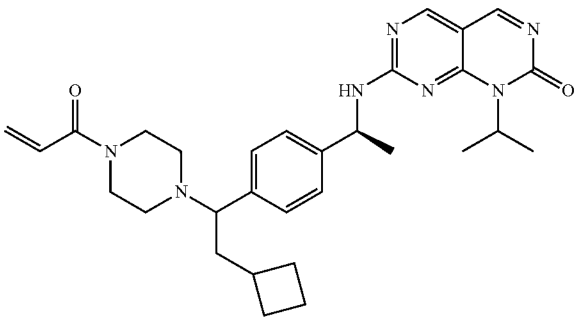
126
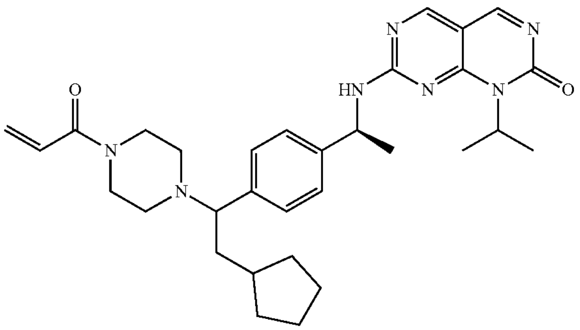
127
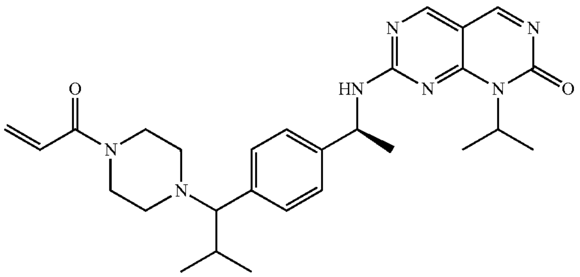
128
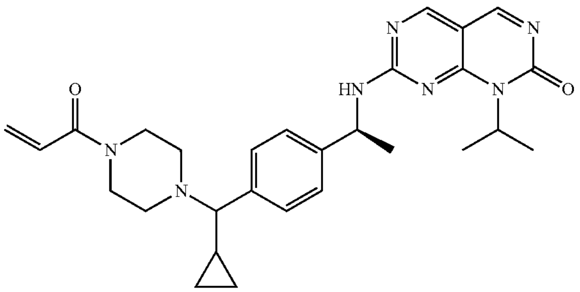
129
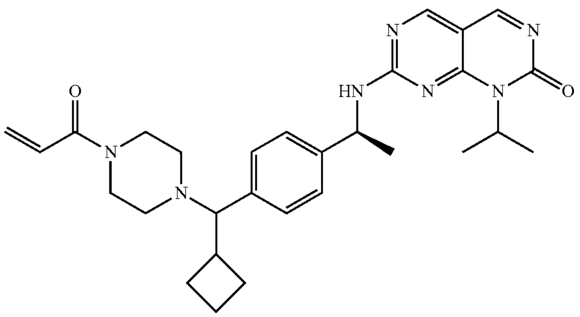
-continued
130
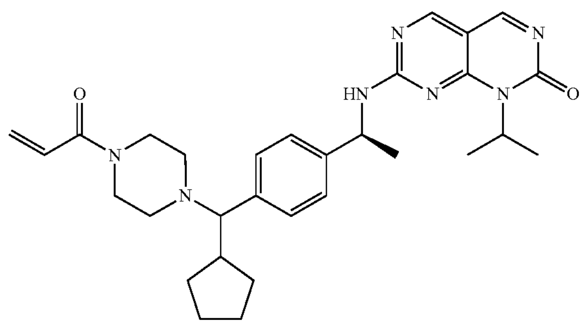
131
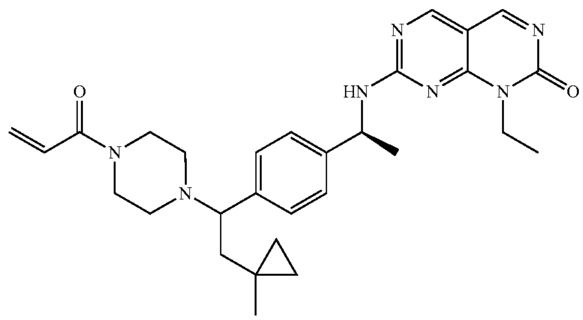
132
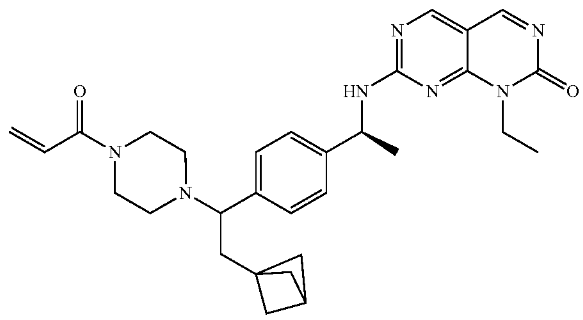
133
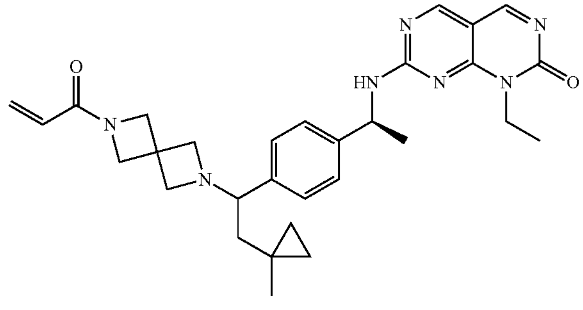

-continued
134
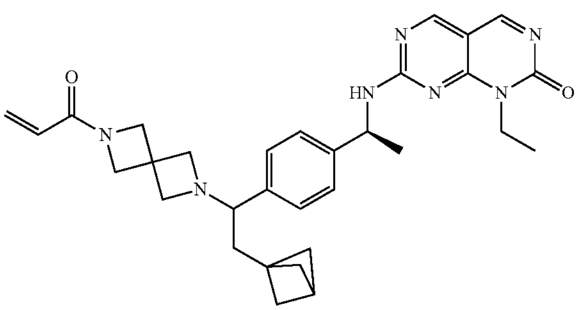
135
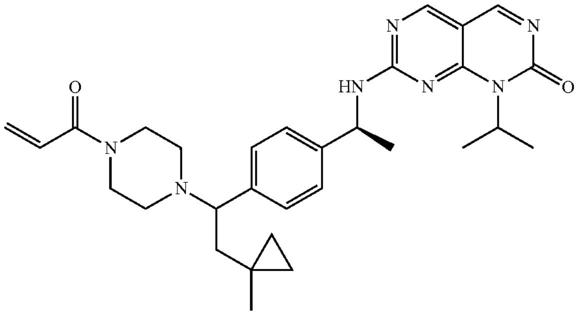
136
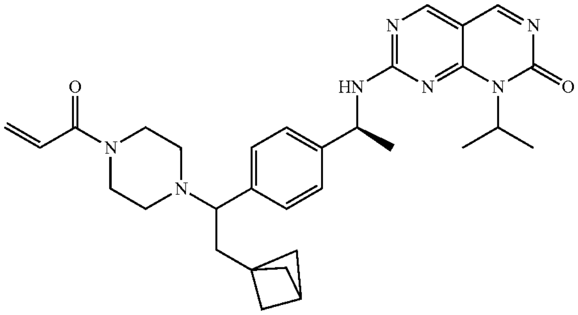
137
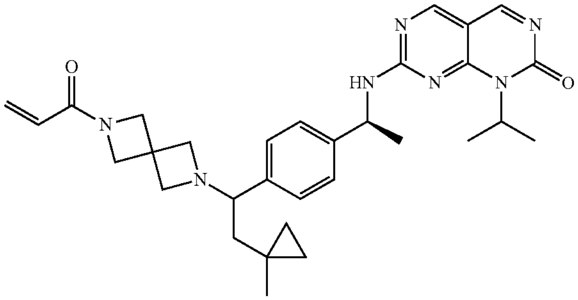
-continued
138
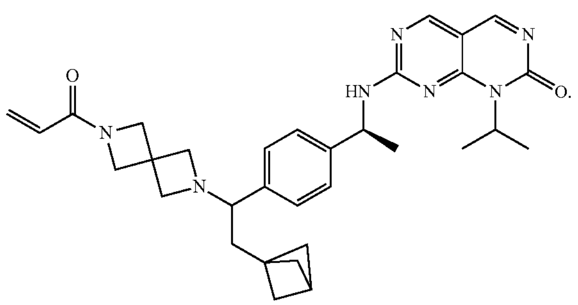
In another aspect, the present invention is intended to provide a compound having the following structure or an isomer, a crystalline form, a pharmaceutically acceptable salt, a hydrate or a solvate thereof.
139
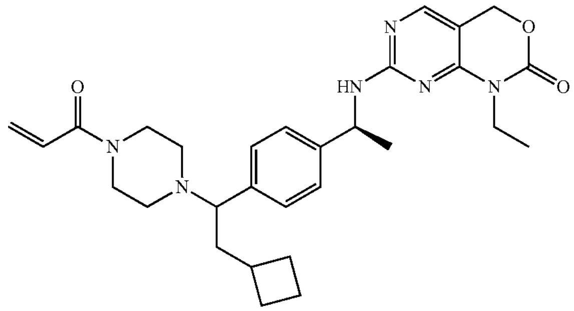
140
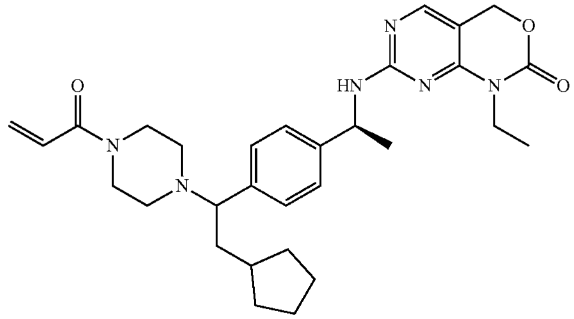
141
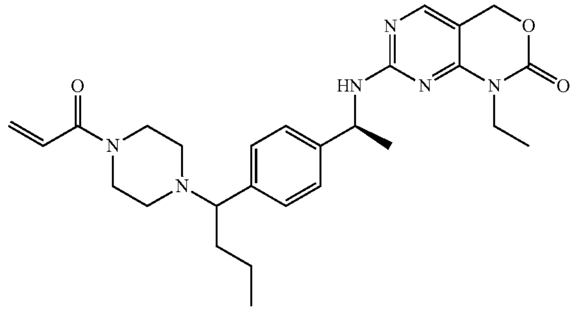

142
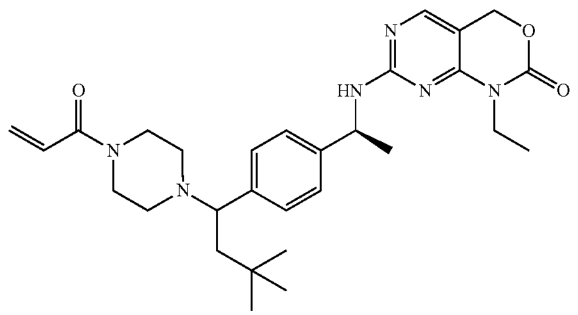
143
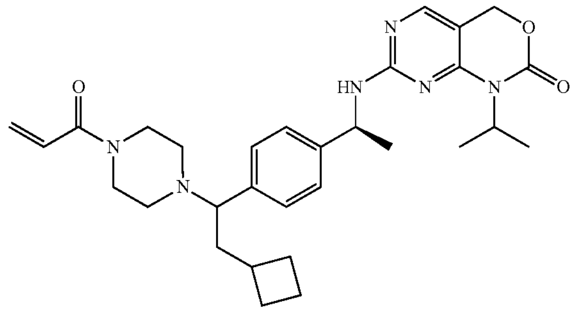
144
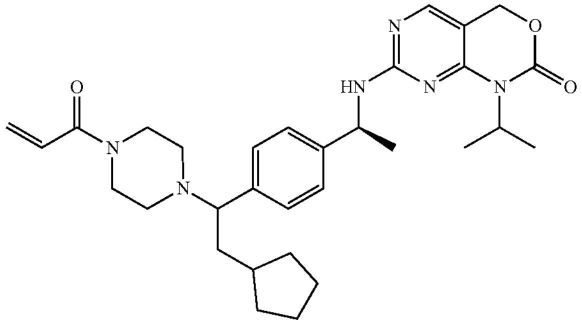
145
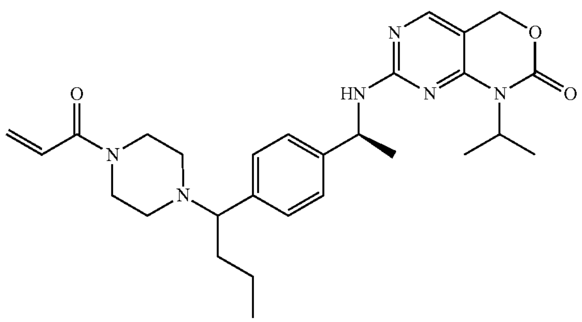
146
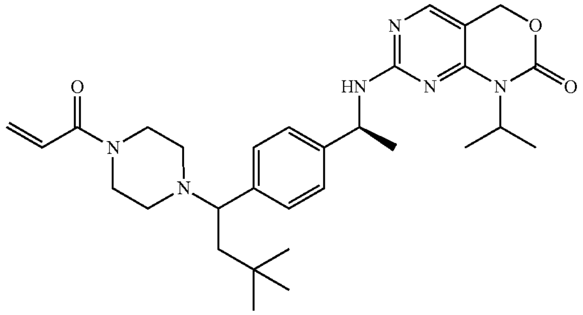
147
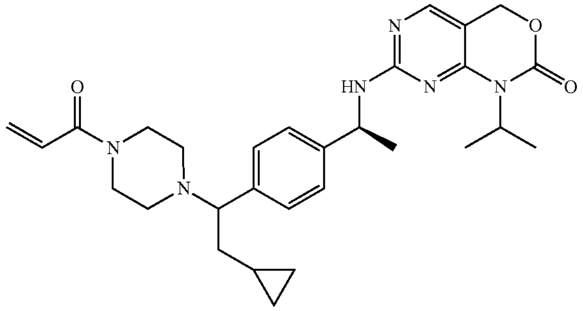
148
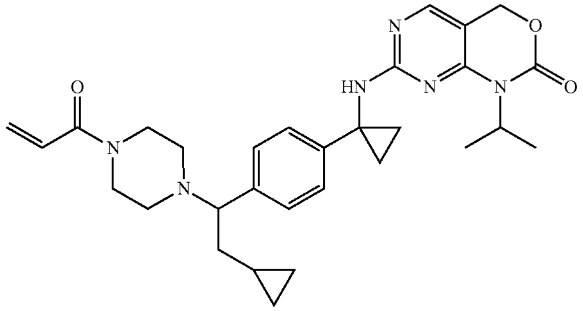
149
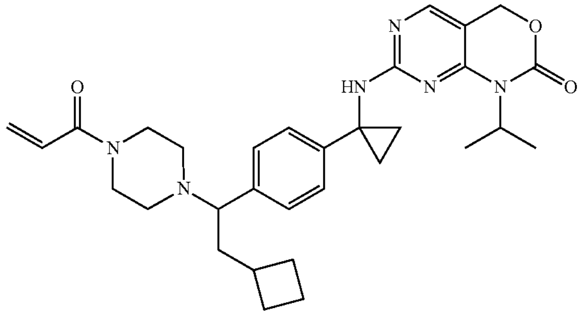

-continued
150
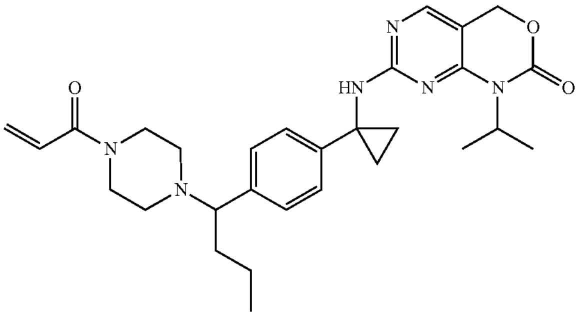
151
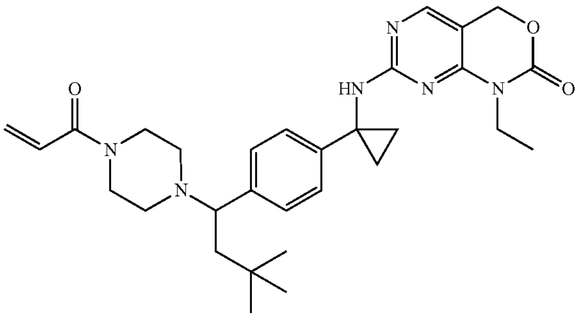
152
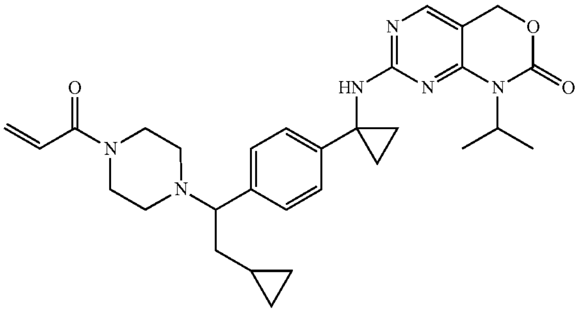
153
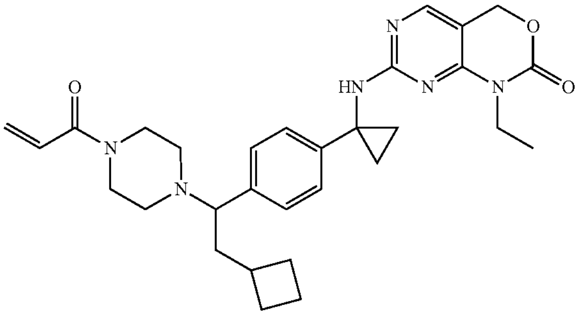
-continued
154
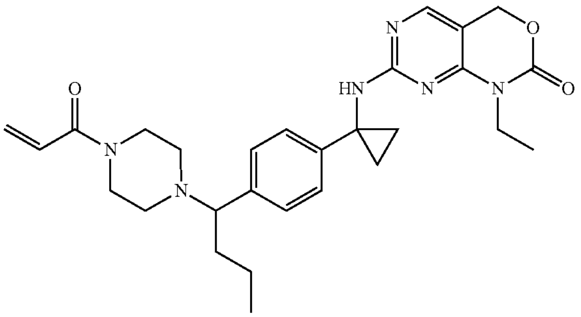
155
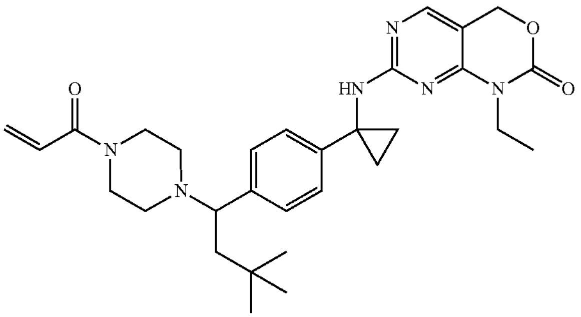
156
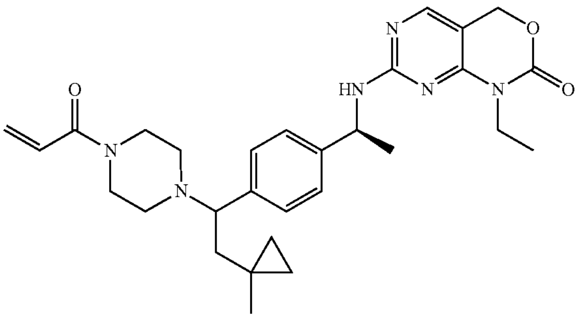
157
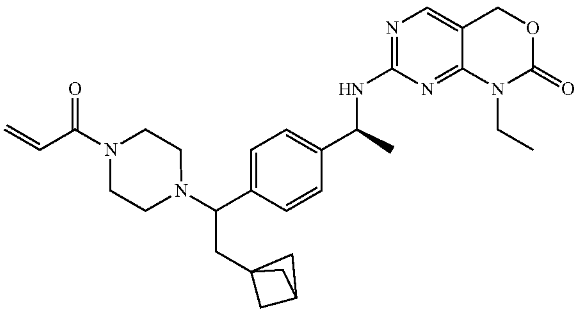

-continued

158

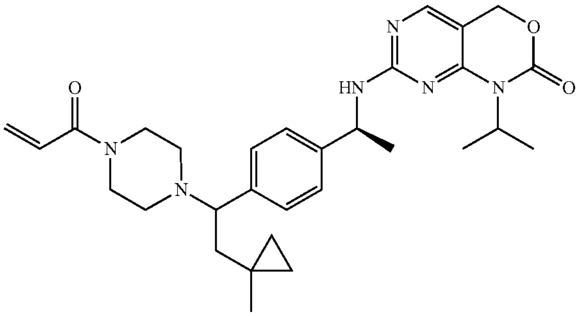

159

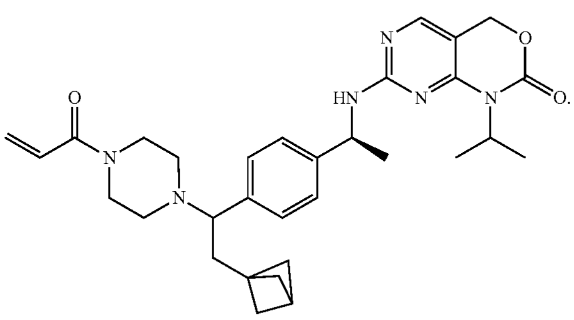

The present invention is further intended to provide a pharmaceutical composition comprising a pharmaceutically acceptable carrier, diluent and/or excipient, and the compound or the isomer, the crystalline form, the pharmaceutically acceptable salt, the hydrate or the solvate thereof disclosed herein as an active ingredient.

The present invention is still further intended to provide use of the compound or the isomer, the crystalline form, the pharmaceutically acceptable salt, the hydrate or the solvate thereof disclosed herein, or the above pharmaceutical composition in preparing a medicament for treating a disease related to an IDH mutant protein.

The present invention is even further intended to provide a method for treating, regulating and/or preventing a disease related to an IDH mutant protein, comprising administering to a subject a therapeutically effective amount of the compound or the isomer, the crystalline form, the pharmaceutically acceptable salt, the hydrate or the solvate thereof disclosed herein, or the above pharmaceutical composition.

It should be understood that both the above general description and the following detailed description of the present invention are exemplary and explanatory, and are intended to provide further explanation of the present invention claimed.

Synthesis of the Compounds

Methods for preparing the compounds of general formulas of the present invention are hereafter described in detail, but these specific methods do not limit the present invention in any way. The compounds of general formulas described above may be synthesized using standard synthetic techniques or well-known techniques in combination with the methods described herein. In addition, solvents, temperatures and other reaction conditions mentioned herein may vary. Starting materials for the synthesis of the compounds may be obtained synthetically or commercially. The compounds described herein and other related compounds having different substituents may be synthesized using well-known techniques and starting materials, including the methods found in March, Advanced Organic Chemistry, 4th Ed., (Wiley 1992); Carey and Sundberg, Advanced Organic Chemistry, 4th Ed., Vols. A and B (Plenum 2000, 2001), and Green and Wuts, Protective Groups in Organic Synthesis, 3rd Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention also provides a method for preparing the compounds of general formulas, which are prepared using general reaction scheme 1 or general reaction scheme 2 below:

General Reaction Scheme 1

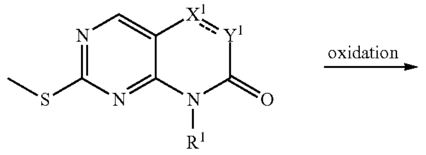

A1

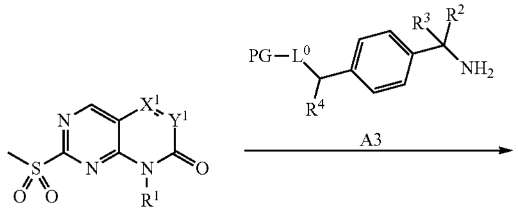

A2

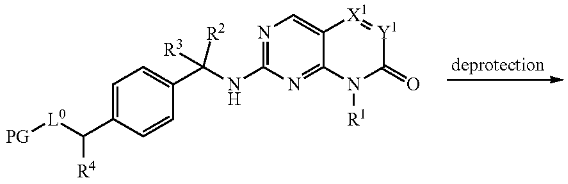

A4

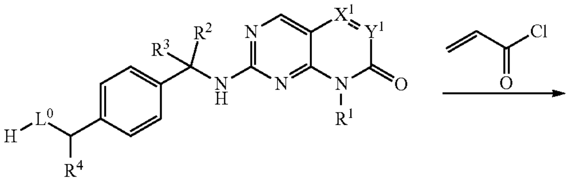

A5

-continued

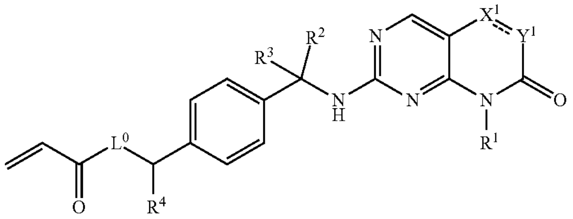

A6

When "$X^1$=$Y^1$" is the following group:

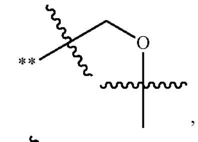 , 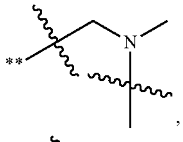 , 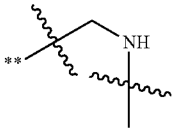 or 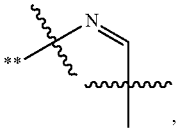 , the compound disclosed herein may be prepared according to general reaction scheme 1 (method A), wherein "**" denotes the position $X^1$ terminal, $L^0$ denotes $L^a$ or $L^b$, PG denotes a protecting group for an amine group, $R^1$, $R^2$, $R^3$, $R^4$, $L^a$ and $L^b$ are as defined above. As shown in general reaction scheme 1, starting material A1 is subjected to oxidation reaction to give compound A2, compound A2 and A3 react in basic conditions to give compound A4, the protecting group PG (e.g., Boc) in compound A4 is removed to give compound A5, and compound A5 reacts with acryloyl chloride to give the target compound A6.

General Reaction Scheme 2

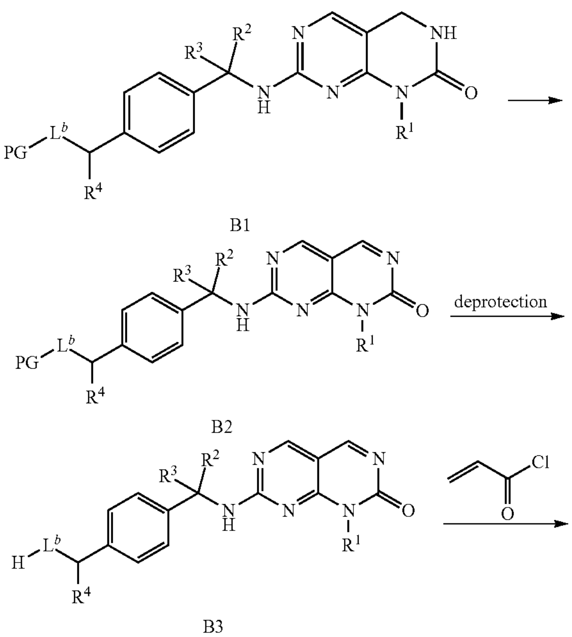

B1

B2

B3

-continued

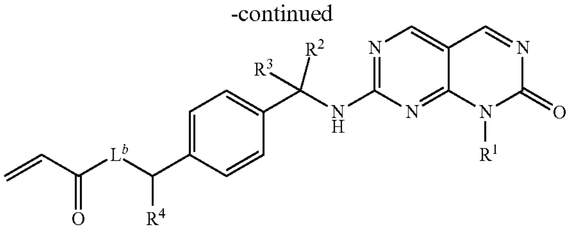

B4

When is

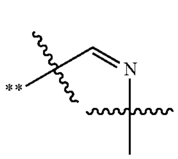

in the compound of general formula (1b), the compound disclosed herein may be prepared according to general reaction scheme 2 (method B), wherein $R^1$, $R^2$, $R^3$, $R^4$ and $L^b$ are as defined above, and PG denotes a protecting group for an amine group. Starting material B1 may be prepared according to the general reaction scheme 1. As shown in general reaction scheme 2, compound B1 is subjected to elimination reaction in basic conditions to give compound B2, the protecting group PG (e.g., Boc) in compound B2 is removed to give compound B3, and compound B3 reacts with acryloyl chloride to give a target compound B4.

Further Forms of Compounds

"Pharmaceutically acceptable" herein refers to a substance, such as a carrier or diluent, which will not cause a compound to lose its biological activity or properties. It is relatively non-toxic; for example, when an individual is given a substance, it will not cause unwanted biological effects or interact with any component contained therein in a deleterious manner.

The term "pharmaceutically acceptable salt" refers to a form of a compound that does not cause significant irritation to the organism for drug administration or eliminate the biological activity and properties of the compound. In certain specific aspects, pharmaceutically acceptable salts are obtained by reacting the compounds of general formulas with acids, e.g. inorganic acids such as hydrochloric acid, hydrobromic acid, hydrofluoric acid, sulfuric acid, phosphoric acid and nitric acid, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid and p-toluenesulfonic acid, and acidic amino acids such as aspartic acid and glutamic acid.

It should be understood that references to pharmaceutically acceptable salts include solvent addition forms or crystal forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. The solvates of the compounds of general formulas are conveniently prepared or formed according to the methods described herein. For example, the hydrates of the compounds of general formulas are conveniently prepared by recrystallization from a mixed solvent of water/organic solvent, wherein the organic solvent used includes, but is not limited to, tetrahydrofuran, acetone, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific examples, the compounds of general formulas are prepared into different forms, including but not limited to amorphous, pulverized and nanoparticle forms. In addition, the compound of general formula includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compound of general formula may have a chiral center and/or axial chirality, and thus may be present in the form of a racemate, a racemic mixture, a single enantiomer, a diastereomeric compound, a single diastereomer and a cis-trans isomer. Each chiral center or axial chirality will independently produce two optical isomers, and all possible optical isomers, diastereomeric mixtures and pure or partially pure compounds are included within the scope of the present invention. The present invention is meant to include all such isomeric forms of these compounds.

The compound of the present invention may contain unnatural proportions of atomic isotopes at one or more of the atoms that constitute such the compound. For example, the compound may be labeled with radioactive isotopes, such as tritium (3H), iodine-125 (125I) and C-14 (14C). For another example, deuterium can be used to substitute a hydrogen atom to form a deuterated compound, the bond formed by deuterium and carbon is stronger than that formed by common hydrogen and carbon, and compared with an undeuterated medicament, the deuterated medicament generally has the advantages of reducing toxic and side effects, increasing medicament stability, enhancing curative effect, prolonging in vivo half-life period of the medicament and the like. All isotopic variations of the compound of the present invention, whether radioactive or not, are intended to be encompassed within the scope of the present invention.

Terminology

Unless otherwise stated, the terms used in the present application, including those in the specification and claims, are defined as follows.

It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA technology and pharmacology are used. As used herein, "or" or "and" refers to "and/or" unless otherwise stated.

"Optional" or "optionally" means that the subsequently described event or circumstance may, but does not necessarily, occur, and the description includes instances where the event or circumstance occurs and instances where it does not.

Unless otherwise stated, the absolute configuration of a stereogenic center is represented by a wedged solid bond ( ) and a wedged dashed bond ( ) and the relative configuration of a stereogenic center is represented by a straight solid bond ( ) and a straight dashed bond ( ). A wavy line ( ) represents a wedged solid bond ( ) or a wedged dashed bond ( ) or a wavy line ( ) represents a straight solid bond ( ) or a straight dashed bond ( ).

Specific Pharmaceutical and Medical Terminology

The term "acceptable", as used herein, means that a formula component or an active ingredient does not unduly adversely affect a general therapeutic target's health.

The terms "treatment," "treatment course," or "therapy", as used herein, include alleviating, inhibiting, or ameliorating a symptom or condition of a disease; inhibiting the development of complications; ameliorating or preventing underlying metabolic syndrome; inhibiting the development of the disease or symptom, e.g., controlling the progression of the disease or condition; alleviating the disease or symptom; causing the disease or symptom to subside; alleviating a complication caused by the disease or symptom, or preventing or treating a sign caused by the disease or symptom. As used herein, a compound or pharmaceutical composition, when administered, can ameliorate a disease, symptom, or condition, particularly meaning ameliorating the severity, delaying the onset, slowing the progression, or reducing the duration of the disease. Fixed or temporary administration, or continuous or intermittent administration, may be attributed to or associated with the administration.

The "active ingredient" refers to compounds of general formulas, and pharmaceutically acceptable inorganic or organic salts of the compounds of general formulas. The compounds of the present invention may contain one or more asymmetric centers (axial chirality) and thus occur in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), is capable of inducing a desired pharmacological and/or physiological response by local and/or systemic action.

The term "administered, administering or administration" refers herein to the direct administration of the compound or composition, or the administration of a prodrug, derivative, analog or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range ±10%, 5%, 1%, or 0.5%. Alternatively, the term "about" indicates that the actual value falls within the acceptable standard error of a mean, as considered by those skilled in the art. All ranges, quantities, values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be construed as the significant digits indicated or the numerical value obtained using conventional rounding rules.

Unless otherwise defined in the specification, the scientific and technical terms used herein have the same meaning as commonly understood by those skilled in the art. Furthermore, the singular nouns used in the specification encompass their plural forms, unless contradicted by context; the plural nouns used also encompass their singular forms.

Therapeutic Use

The present invention provides a method for treating a disease, including but not limited to a condition related to an IDH mutant protein (e.g., a cancer), with the compound or pharmaceutical composition disclosed herein.

In some embodiments, provided is a method for treating a cancer, comprising administering to an individual in need an effective amount of any aforementioned pharmaceutical composition comprising the compound disclosed herein. In some embodiments, the cancer is mediated by an IDH mutant protein. In other embodiments, the cancer is a hematologic cancer and a solid tumor, including but not limited to leukemia, lung cancer, pancreatic cancer, colon cancer, gallbladder cancer or colorectal cancer.

Route of Administration

The compound and the pharmaceutically acceptable salt thereof of the present invention can be prepared into various preparations which include the compound or the pharmaceutically acceptable salt thereof disclosed herein in a safe and effective amount range and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound of the present invention and with each other, without significantly diminishing the pharmaceutical efficacy of the compound. Examples of pharmaceutically acceptable excipients or carriers are cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., TWEEN), wetting agents (e.g., sodium lauryl sulfate), colorants, flavoring agents, stabilizers, antioxidants, preservatives, pyrogen-free water, etc. When the compound of the present invention is administered, it may be administered orally, rectally, parenterally (intravenously, intramuscularly or subcutaneously) or topically. Solid dosage forms for oral administration include capsules, tablets, pills, and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato or tapioca starch, alginic acid, certain complex silicates and sodium carbonate; I solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may also include buffers.

Solid dosage forms such as tablets, dragees, capsules, pills and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, groundnut oil, corn germ oil, olive oil, castor oil and sesame oil, or mixtures of these substances.

Besides such inert diluents, the composition may also include adjuvants, such as wetting agents, emulsifiers, suspending agents, sweeteners, flavoring agents, and perfuming agents. Suspensions, in addition to the active compound, may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound of the present invention include ointments, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds.

When the pharmaceutical composition is used, a safe and effective amount of the compound of the present invention is administered to a mammal (such as a human) to be treated, wherein the administration dose is a pharmaceutically effective administration dose. For a human weighing 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise expressly stated, the features disclosed are merely general examples of equivalent or similar features.

DETAILED DESCRIPTION

Various specific aspects, features and advantages of the compounds, methods and pharmaceutical compositions described above are set forth in detail in the following description, which makes the present invention clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, $^1$H-NMR spectra were recorded with a Vian Mercury 400 nuclear magnetic resonance spectrometer, and chemical shifts are expressed in δ (ppm); silica gel for separation was 200-300 mesh silica gel if not specified, and the ratio of the eluents was volume ratio. In the present invention, the following abbreviations are used: AcOH (or HOAc) represents acetic acid; Ar represents argon; $CDCl_3$ represents deuterated chloroform; CDI represents carbonyldiimidazole; $Cs_2CO_3$ represents cesium carbonate; CsF represents cesium fluoride; DBU represents 1,8-diazabicyclo [5.4.0]undec-7-ene; DCM represents dichloromethane; DIPEA represents diisopropylethylamine; DMF represents dimethylformamide; DMSO represents dimethyl sulfoxide; EA represents ethyl acetate; EtOH represents ethanol; h represents hour; $H_2$ represents hydrogen; NaOH represents sodium hydroxide; KOH represents potassium hydroxide; LC-MS represents liquid chromatography—mass spectrometry; $LiAlH_4$ represents lithium aluminum hydride; m-CPBA represents m-chloroperoxybenzoic acid; MeOH represents methanol; min represents minute; mL represents milliliter; $MnO_2$ represents manganese dioxide; MS represents mass spectrum; $NaBH_3CN$ represents sodium cyanoborohydride; $NaBH_4$ represents sodium borohydride; n-BuLi represents n-butyllithium; $NaBH(OAc)_3$ represents sodium triacetoxyborohydride; $Na_2SO_3$ represents sodium sulfite; $Na_2SO_4$ represents sodium sulfate; $NH_4Cl$ represents ammonium chloride; NMR represents nuclear magnetic resonance; Pd/C represents palladium on carbon; PE represents petroleum ether; t-BuOK represents potassium tert-butoxide; TEA represents triethylamine; TFA (or $CF_3COOH$) represents trifluoroacetic acid; THF represents tetrahydrofuran; $Ti(O^iPr)_4$ represents titanium tetraisopropoxide; and toluene represents methylbenzene.

Preparation Example 1. Synthesis of 1-ethyl-7-(methylthio)-1,4-dihydro-2H-pyrimidinyl[4,5-d][1,3]oxazin-2-one (A-1)

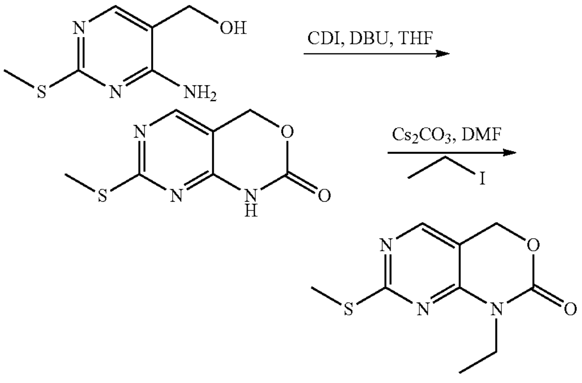

A-1

Synthesis of 7-(methylthio)-1,4-dihydro-2H-pyrimidinyl[4,5-d][1,3]oxazin-2-one In a 250 mL single-neck flask, (4-amino-2-(methylthio) pyrimidin-5-yl)methanol (4.5 g, 26.28 mmol) was dissolved in THF (50 mL), DBU (8.0 g, 52.56 mmol) and CDI (4.69 g, 28.91 mmol) were added, and the mixed solution was purged with argon and stirred at room temperature for 2 h. After the completion of the reaction as detected by LC-MS, the mixed solution was quenched with $H_2O$ (50 mL), adjusted to pH 4-5 with 6 N hydrochloric acid, and then EA (15 mL)/PE (15 mL) was added. The mixed solution was stirred at room temperature for 30 min and then filtered at reduced pressure, and the filter cake was rinsed with a mixed solution of EA/PE=1/1 (10 mL) and dried in vacuum to give a light brown solid product (3.57 g, 69% yield). ESI-MS m/z: 198 $[M+H]^+$.

Synthesis of 1-ethyl-7-(methylthio)-1,4-dihydro-2H-pyrimidinyl[4,5-d][1,3]oxazin-2-one In a 250 mL single-neck flask, 7-(methylthio)-1,4-dihydro-2H-pyrimidinyl[4,5-d][1,3]oxazine-2-one (3.69 g, 18.71 mmol) was dissolved in DMF (40 mL), and $Cs_2CO_3$ (7.5 g, 23.01 mmol) was added. The mixed solution was cooled to 0-5° C. in an ice bath in argon atmosphere, and then EtI (3.77 g, 24.14 mmol) was added dropwise. After the addition, the mixed solution was stirred at room temperature for 20 h. After the completion of the reaction as detected by LC-MS, the mixed solution was quenched with $H_2O$ (80 mL), and extracted with EA (40 mL×3). The organic phases were combined, washed twice with saturated sodium chloride solution (40 mL×2), dried over anhydrous $Na_2SO_4$, filtered, and concentrated at reduced pressure. The residue was purified by column chromatography to give an off-white solid A-1 (3.9 g, 93% yield). ESI-MS m/z: 226 $[M+H]^+$.

Preparation Examples 2-6. Synthesis of Intermediates A-2 to A-6

Target intermediates A-2 to A-6 were obtained by using different starting materials according to the synthesis method for the intermediate A-1.

TABLE 1

| Structural formulas of intermediates A-2 to A-6 | | |
|---|---|---|
| Intermediate | Compound structure | MS $[M + H]^+$ |
| A-2 | 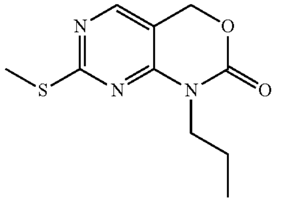 [SMILES: CCCN1C(=O)OCc2cnc(SC)nc21] | 240 |
| A-3 | 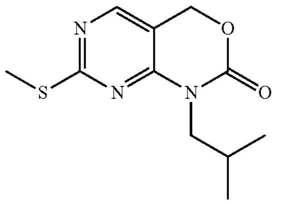 | 254 |
| A-4 | 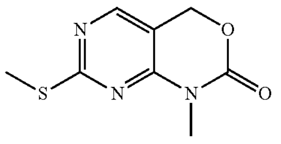 | 212 |
| A-5 | 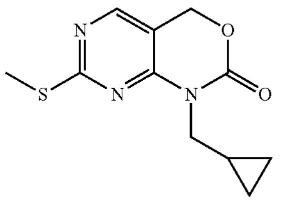 [SMILES: CSc1ncc2c(n1)N(CC1CC1)C(=O)OC2] | 252 |
| A-6 | 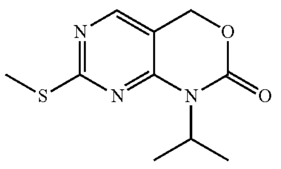 [SMILES: CSc1ncc2c(n1)N(C(C)C)C(=O)OC2] | 240 |

Preparation Example 7. Synthesis of 1-isopropyl-7-(methylthio)-3,4-dihydropyrimido[4,5-d]pyrimidine-2(1H)-one (A-7)

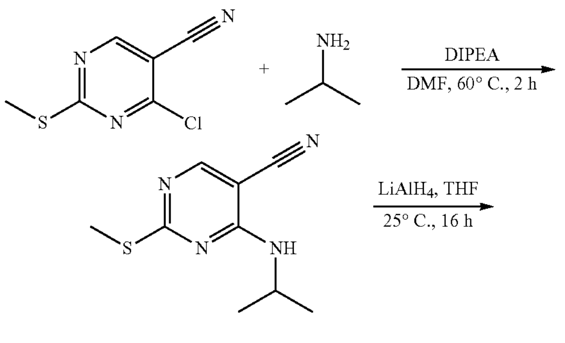

-continued

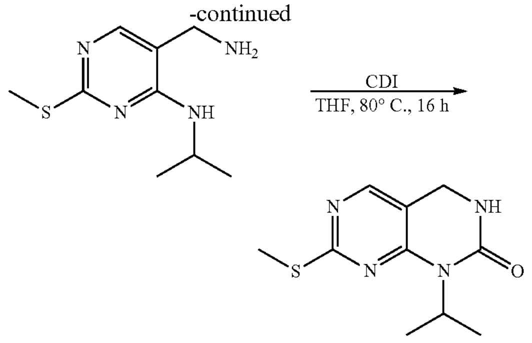

A-7

Synthesis of 4-(isopropylamino)-2-(methylthio)pyrimidine-5-carbonitrile

4-Chloro-2(methylthio)pyrimidine-5-carbonitrile (3.71 g, 20 mmol) was dissolved in DMF (30 mL), and isopropylamine (1.2 g, 20 mmol) and DIPEA (6.5 g, 50 mmol) were added. After the addition, the mixed solution was heated to 60° C., and incubated for 2 h for reaction. After the completion of the reaction as detected by TLC, the mixed solution was diluted with water (100 mL), and extracted 3 times with EA (50 mL×3). The organic phases were combined, washed with saturated sodium chloride solution (50 mL), dried over anhydrous $Na_2SO_4$, filtered, and concentrated at reduced pressure to give a crude product (3.82 g, 92% yield). ESI-MS m/z: 209 $[M+H]^+$.

Synthesis of 5-(methylamino)-N-isopropyl-2-(methylthio)pyrimidine-4-amine 4-(Isopropylamino)-2-(methylthio)pyrimidine-5-carbonitrile (3.74 g, 18 mmol) obtained in the previous step was dissolved in anhydrous THF (15 mL), the mixed solution was cooled to 0° C. in nitrogen atmosphere, and a solution of $LiAlH_4$ (1.37 g, 36 mmol) dissolved in THF (40 mL) was added slowly to the reaction system. After the addition, the system was heated to room temperature, and incubated for 16 h for reaction. After the completion of the reaction as detected by TLC, $Na_2SO_4·10H_2O$ (7 g) was added slowly to the system at 0° C., the solid was filtered, and the filter cake was washed with a small amount of THF. The organic phases were combined, and the solvent was concentrated to dryness by rotary evaporation at reduced pressure to give an intermediate 5-(methylamino)-N-isopropyl-2-(methylthio)pyrimidine-4-amine (3.21 g, 84% yield). ESI-MS m/z: 213 $[M+H]^+$.

Synthesis of 1-isopropyl-7-(methylthio)-3,4-dihydropyrimido[4,5-d]pyrimidine-2(1H)-one 5-(Methylamino)-N-isopropyl-2-(methylthio)pyrimidine-4-amine (3.18 g, 15 mmol) was dissolved in anhydrous THF (50 mL), the mixed solution was cooled to 0° C. in an ice salt bath, CDI (2.92 g, 18 mmol) and TEA (3.03 g, 30 mmol) were added. The mixed solution was incubated for 0.5 h for reaction, then heated to 80° C., and incubated for 16 h for reaction. After the completion of the reaction as detected by TLC, the mixed solution was concentrated, and the residue was purified by column chromatography to give 1-isopropyl-7-(methylthio)-3,4-dihydropyrimido[4,5-d]pyrimidine-2(1H)-one (2.36 g, 66% yield). $^1H$ NMR (400 MHz, DMSO- $d_6$) δ: 8.18 (s, 1H), 7.41 (br s, 1H), 4.97 (spt, J=6.9 Hz, 1H), 4.19 (d, J=0.9 Hz, 2H), 2.49 (s, 3H), 1.43 (d, J=6.9 Hz, 6H); ESI-MS m/z: 239 $[M+H]^+$.

Preparation Examples 8-13. Synthesis of Intermediates A-8 to A-13

Target intermediates A-8 to A-13 were obtained by using different starting materials according to the synthesis method for the intermediate A-7.

TABLE 2

Structural formulas of intermediates A-8 to A-13

| Intermediate | Compound structure | MS $[M + H]^+$ |
|---|---|---|
| A-8 | 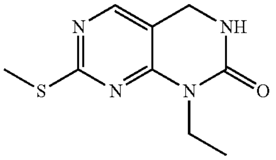 | 225 |
| A-9 | 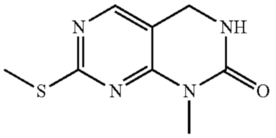 | 211 |
| A-10 | 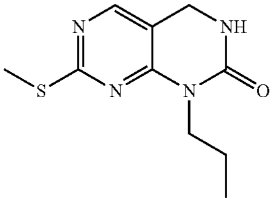 [SMILES: CCCN1C(=O)NCc2cnc(SC)nc21] | 239 |
| A-11 | 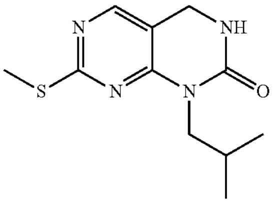 [SMILES: CSc1ncc2c(n1)N(CC(C)C)C(=O)NC2] | 253 |
| A-12 | 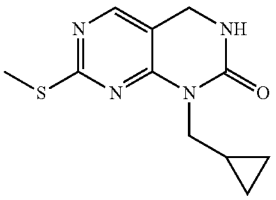 [SMILES: CSc1ncc2c(n1)N(CC1CC1)C(=O)NC2] | 251 |
| A-13 | 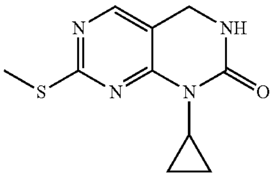 [SMILES: CSc1ncc2c(n1)N(C1CC1)C(=O)NC2] | 237 |

Preparation Example 14. Synthesis of 1-isopropyl-3-methyl-7-(methylthio)-3,4-dihydropyrimidine[4,5-d]pyrimidine-2(1H)-one (A-14)

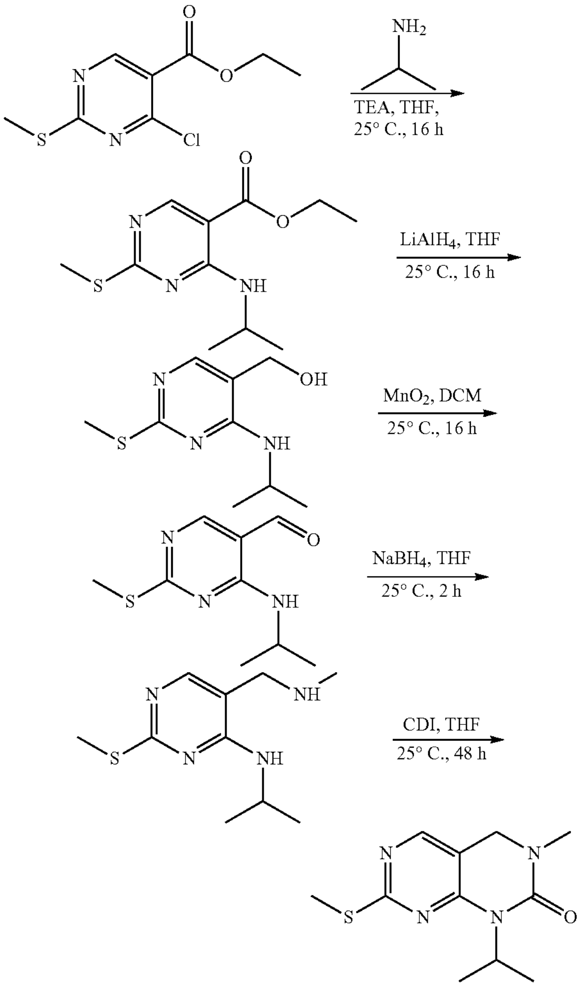

A-14

Synthesis of ethyl 4-(isopropylamino)-2-(methylthio)pyrimidine-5-carboxylate Ethyl 4-chloro-2-(methylthio)pyrimidine-5-carboxylate (50 g, 214.88 mmol) was dissolved in THF (500 mL), the mixed solution was cooled to 0° C. in an ice salt bath, and TEA (43.49 g, 429.76 mmol, 59.82 mL) was added. After the addition, the mixed solution was incubated at room temperature for 16 h for reaction. After the completion of the reaction as detected by TLC, water (200 mL) was added, and the mixed solution was extracted with EA (200 mL×2). The organic phases were combined, washed with saturated sodium chloride solution (100 mL), dried over anhydrous $Na_2SO_4$, filtered, and concentrated at reduced pressure to give a target compound (52.50 g, 96% yield).

$^1H$ NMR (400 MHz, DMSO-$d_6$) δ: 8.54 (s, 1H), 8.08 (br d, J=7.4 Hz, 1H), 4.30-4.23 (m, 2H), 2.48 (s, 3H), 1.30 (t, J=7.1 Hz, 3H), 1.23 (d, J=6.5 Hz, 6H); ESI-MS m/z: 256 $[M+H]^+$.

Synthesis of (4-(isopropylamino)-2-(methylthio)pyrimidin-5-yl)methanol

Ethyl 4-(isopropylamino)-2-(methylthio)pyrimidine-5-carboxylate (30 g, 117.49 mmol) was dissolved in anhydrous THF (300 mL), the mixed solution was cooled to 0° C. in nitrogen atmosphere, and a solution of $LiAlH_4$ (6.69 g, 176.24 mmol) dissolved in THF (50 mL) was added slowly to the reaction system. After the addition, the mixed solution was incubated for 3 h for reaction. After the completion of the reaction as detected by TLC, $Na_2SO_4.10H_2O$ (10 g) was added slowly to the system at 0° C., the solid was filtered, and the filter cake was washed with a small amount of THF. The organic phases were combined, the solvent was concentrated to dryness by rotary evaporation at reduced pressure, and the residue was purified by column chromatography to give (4-(isopropylamino)-2-(methylthio)pyrimidin-5-yl)methanol (19.5 g, 78% yield).

$^1$H NMR (400 MHz, DMSO-$d_6$) δ: 7.82 (s, 1H), 6.40 (br d, J=7.5 Hz, 1H), 5.13 (t, J=5.5 Hz, 1H), 4.31 (d, J=5.5 Hz, 2H), 2.41 (s, 3H), 1.18 (d, J=6.5 Hz, 5H), 1.23-1.12 (m, 1H); ESI-MS m/z: 214 $[M+H]^+$.

Synthesis of 4-(isopropylamino)-2-(methylthio)pyrimidine-5-carbaldehyde (4-(Isopropylamino)-2-(methylthio)pyrimidin-5-yl) methanol (19.50 g, 91.42 mmol) obtained in the previous step was dissolved in DCM (150 mL), $MnO_2$ (119.22 g, 1.37 mol) was added, and the mixed solution was incubated at room temperature for 16 h for reaction. After the completion of the reaction as detected by TLC, the mixed solution was filtered, and the filter cake was washed with a small amount of DCM. The organic phases were combined, the solvent was concentrated to dryness by rotary evaporation at reduced pressure, and the residue was purified by column chromatography to give 4-(isopropylamino)-2-(methylthio) pyrimidine-5-carbaldehyde (18.2 g, 94% yield).

$^1$H NMR (400 MHz, DMSO-$d_6$) δ: 9.84-9.68 (m, 1H), 8.58-8.48 (m, 1H), 4.48-4.25 (m, 1H), 2.51 (s, 3H), 1.24 (d, J=6.5 Hz, 6H); ESI-MS m/z: 212 $[M+H]^+$.

Synthesis of N-isopropyl-5-((methylamino)methyl)-2-(methylthio)pyrimidine-4-amine 4-(Isopropylamino)-2-(methylthio)pyrimidine-5-carbaldehyde (10 g, 47.33 mmol) was dissolved in MeOH (100 mL), and AcOH (2.84 g, 47.33 mmol, 2.71 mL), methylamine (14.70 g, 141.99 mmol, 30% aqueous solution) and $NaBH_3CN$ (6.84 g, 108.86 mmol) were added. After the addition, the mixed solution was incubated at room temperature for 16 h for reaction. After the completion of the reaction as detected by TLC, $H_2O$ (30 mL) was added, and the mixed solution was extracted with EA (100 mL×2). The organic phases were combined, washed with saturated sodium chloride solution (50 mL), dried over anhydrous $Na_2SO_4$, filtered, and concentrated at reduced pressure. The residue was purified by column chromatography to give a target compound (5.70 g, 67% yield).

$^1$H NMR (400 MHz, DMSO-$d_6$) δ: 8.29 (d, J=1.3 Hz, 1H), 8.16 (s, 1H), 4.41-4.18 (m, 1H), 4.03 (q, J=7.1 Hz, 1H), 3.41 (d, J=1.3 Hz, 3H), 2.46 (s, 3H), 1.21 (d, J=6.6 Hz, 6H); ESI-MS m/z: 227 $[M+H]^+$.

Synthesis of 1-isopropyl-3-methyl-7-(methylthio)-3,4-dihydropyrimidine[4,5-d]pyrimidine-2(1H)-one (A-14)

N-isopropyl-5-((methylamino)methyl)-2-(methylthio)pyrimidine-4-amine (3.0 g, 13.25 mmol) was dissolved in anhydrous THF (40 mL), the mixed solution was cooled to 0° C. in an ice salt bath, and CDI (2.58 g, 15.91 mmol) and TEA (2.68 g, 26.51 mmol, 3.69 mL) were added. After addition, the mixed solution was heated to 80° C., reacted for 48 h. After the completion of the reaction as detected by TLC, the system was concentrated, and the residue was purified by column chromatography to give a target compound A-14 (2.18 g, 65% yield).

$^1$H NMR (400 MHz, DMSO-$d_6$) δ: 8.20 (s, 1H), 5.02 (spt, J=6.9 Hz, 1H), 4.31 (d, J=0.8 Hz, 2H), 2.90 (s, 3H), 1.43 (d, J=6.9 Hz, 6H); ESI-MS m/z: 253 $[M+H]^+$.

Preparation Example 15. Synthesis of 8-isopropyl-2-(methylthio)pteridine-7(8H)-one (A-15)

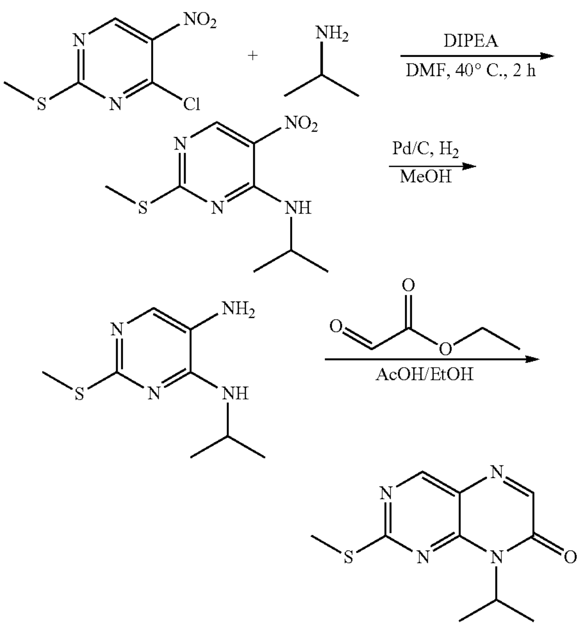

A-15

N-isopropyl-2-(methylthio)-5-nitropyrimidine-4-amine

4-Chloro-2-methylthio-5-nitropyrimidine (20.56 g, 100 mmol) was dissolved in DMF (150 mL), and isopropylamine (5.9 g, 100 mmol) and DIPEA (32.5 g, 250 mmol) were added. After the addition, the mixed solution was heated to 60° C., and incubated for 2 h for reaction. After the completion of the reaction as detected by TLC, the mixed solution was diluted with water (400 mL) and extracted 3 times with EA (300 mL×3). The organic phases were combined, washed with saturated sodium chloride solution (200 mL), dried over anhydrous $Na_2SO_4$, filtered, and concentrated at reduced pressure to give a crude product (18.55 g, 81% yield). ESI-MS m/z: 229 $[M+H]^+$.

$N^4$-isopropyl-2-(methylthio)pyrimidine-4,5-diamine

N-isopropyl-2-(methylthio)-5-nitropyrimidine-4-amine (18.0 g, 78.85 mmol) was dissolved in MeOH (150 mL), and Pd/C (3.00 g, 78.85 mmol, 10% content) was added slowly in batches. The mixed solution was purged three times with $H_2$, and incubated at room temperature in $H_2$ atmosphere for 2 h for reaction. After the completion of the reaction as detected by TLC, the mixed solution was filtered, the filter cake was washed with a small amount of MeOH, and the filtrate was dried by rotary evaporation to give a target compound (11.0 g, 70% yield). $^1$H NMR (400 MHz, DMSO-$d_6$) δ: 1.17 (d, J=6.48 Hz, 6H), 2.30-2.39 (m, 3H), 4.12-4.23 (m, 1H), 4.54 (br s, 2H), 6.26 (br d, J=7.09 Hz, 1H), 7.38-7.44 (m, 1H); ESI-MS m/z: 199 $[M+H]^+$.

Synthesis of 8-isopropyl-2-(methylthio)pteridine-7 (8H)-one (A-15)

$N^4$-isopropyl-2-(methylthio)pyrimidine-4,5-diamine (11.00 g, 55.47 mmol) was dissolved in EtOH (200 mL), ethyl glyoxalate (11.33 g, 110.95 mmol) was added, and HOAc (11.55 g, 192.33 mmol, 11.00 mL) was added slowly. After the addition, the mixed solution was heated to 100° C., and incubated for 16 h for reaction. After the completion of the reaction as detected by TLC, the solvent was concentrated to dryness by rotary evaporation at reduced pressure, and the residue was purified by column chromatography to give a target compound A-15 (6.60 g, 50% yield). $^1$H NMR (400 MHz, DMSO-$d_6$) δ: 1.54 (d, J=6.97 Hz, 6H), 2.62 (s, 3H), 5.52 (dt, J=13.82, 6.91 Hz, 1H), 8.11-8.16 (m, 1H), 8.94 (s, 1H); ESI-MS m/z: 237 $[M+H]^+$.

Preparation Example 16. Synthesis of tert-butyl 4-(1-(4-((S)-1-aminoethyl)phenyl)-2-cyclopropyl-ethyl)piperazine-1-carboxylate (B-1)

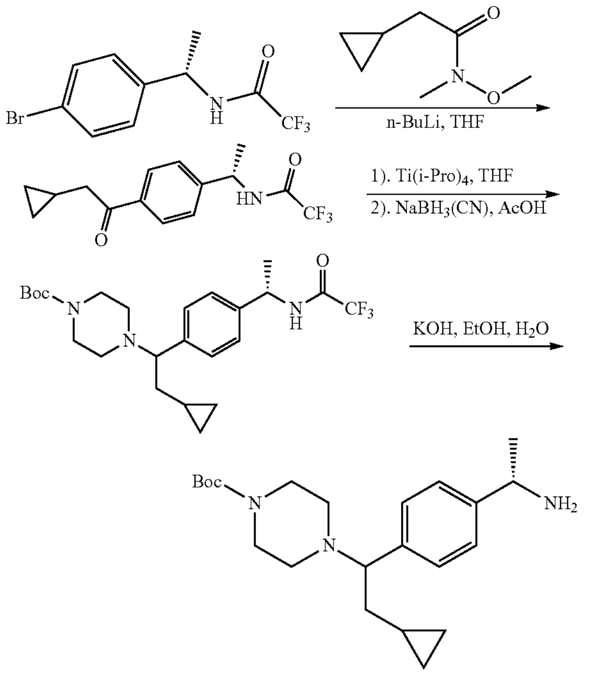

B-1

Synthesis of (S)—N-(1-(4-(2-cyclopropylacetyl) phenyl)ethyl)-2,2,2-trifluoroacetamide (S)—N-(1-(4-bromophenyl)ethyl)-2,2,2-trifluoroacetamide (10.7 g, 36.2 mmol) was dissolved in anhydrous THF (100 mL), and n-BuLi (2.5 M, 30 mL, 72.3 mmol) was added dropwise at −78° C. in argon atmosphere. After the addition, the mixed solution was incubated at −78° C. to −60° C. for about 1 h for reaction, and then a solution of 2-cyclopropyl-N-methoxy-N-methylacetamide (5.7 g, 39.8 mmol) in anhydrous THF (50 mL) was slowly added dropwise. After the addition, the mixed solution was incubated at the temperature for 0.5 h for reaction. After the completion of the reaction as detected by LC-MS, the mixed solution was quenched with saturated aqueous $NH_4Cl$ solution (100 mL), and extracted twice with EA (50 mL×2), the organic phase was concentrated, and the residue was purified by column chromatography to give a white solid product (6.06 g, 56% yield). ESI-MS m/z: 300 $[M+H]^+$.

Synthesis of tert-butyl 4-(2-cyclopropyl-1-(4-((S)-1-(2,2,2-trifluoroacetylamino)ethyl)phenyl)ethyl)piperazine-1-carboxylate (S)—N-(1-(4-(2-cyclopropylacetyl)phenyl)ethyl)-2,2,2-trifluoroacetamide (3.068 g, 10.25 mmol) and tert-butyl piperazine-1-carboxylate (3.82 g, 20.5 mmol) were dissolved in anhydrous THF (50 mL), $Ti(i\text{-}PrO)_4$ (15 mL, 51.25 mmol) was added dropwise in argon atmosphere, and the mixed solution was incubated overnight at 60° C. for reaction. After cooling to room temperature, methanol (20 mL) and $NaBH(OAc)_3$ (1.288 g, 20.5 mmol) were added, the mixed solution was incubated at room temperature for 10 h for reaction, and a small amount of remaining starting materials was detected by LC-MS. The mixed solution was quenched with water (100 mL), and extracted with EA (50 mL×2). The organic phase was concentrated, and the residue was purified by column chromatography to give a white solid product (957 mg, 20% yield) while recovering the unreacted starting materials (2.2 g). ESI-MS m/z: 470 $[M+H]^+$.

Synthesis of tert-butyl 4-(1-(4-((S)-1-aminoethyl) phenyl)-2-cyclopropylethyl)piperazine-1-carboxylate (B-1)

tert-Butyl 4-(2-cyclopropyl-1-(4-((S)-1-(2,2,2-trifluoroacetylamino)ethyl)phenyl)ethyl)-piperazine-1-carboxylate (3.74 g, 7.97 mmol) was dissolved in $EtOH/H_2O$ (100 mL/20 mL), KOH (2.24 g, 39.87 mmol) was added in batches in an ice bath, and the mixed solution was heated to 50° C. in argon atmosphere and incubated for 3 h for reaction. After the completion of the reaction as detected by LC-MS, the mixed solution was concentrated at reduced pressure to remain about 30 mL, and the remaining mixture was diluted with water (50 mL), and extracted with DCM (50 mL×2). The organic phases were combined, washed with saturated sodium chloride solution (50 mL), dried over anhydrous sodium sulfate, filtered and concentrated at reduced pressure to give a target compound (3.854 g, 100% yield). ESI-MS m/z: 374 $[M+H]^+$.

Preparation Examples 17-83. Synthesis of Intermediates B-2 to B-68

Target intermediates B-2 to B-68 were obtained by using different starting materials according to the synthesis method for the intermediate B-1

TABLE 3
| Structural formulas of intermediates B-2 to B-68 | | |
|---|---|---|
| Intermediate | Compound structure | MS $[M + H]^+$ |
| B-2 | 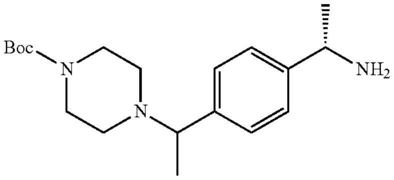 [SMILES: CC(c1ccc([C@H](C)N)cc1)N1CCN(C(=O)OC(C)(C)C)CC1] | 334 |
| B-3 | 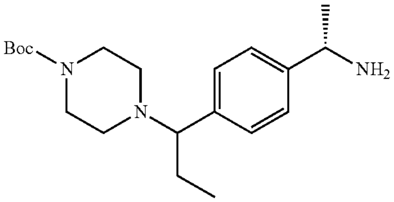 [SMILES: CCC(c1ccc([C@H](C)N)cc1)N1CCN(C(=O)OC(C)(C)C)CC1] | 348 |
| B-4 | 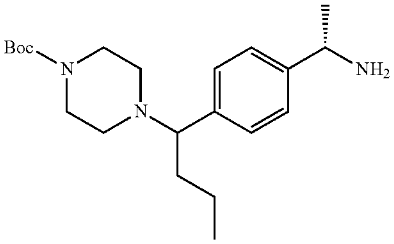 [SMILES: CCCC(c1ccc([C@H](C)N)cc1)N1CCN(C(=O)OC(C)(C)C)CC1] | 362 |
| B-5 | 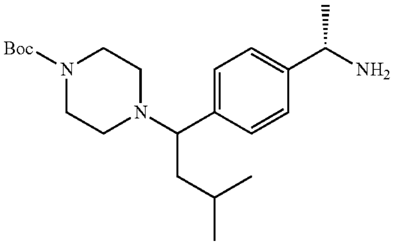 [SMILES: CC(C)CC(c1ccc([C@H](C)N)cc1)N1CCN(C(=O)OC(C)(C)C)CC1] | 376 |
| B-6 | 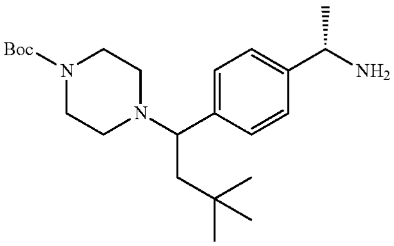 [SMILES: C[C@H](N)c1ccc(C(CC(C)(C)C)N2CCN(C(=O)OC(C)(C)C)CC2)cc1] | 390 |
| B-7 | 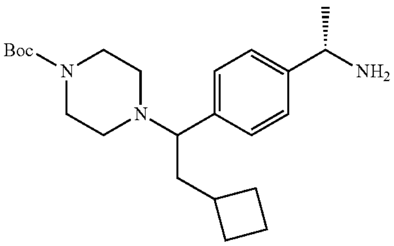 [SMILES: C[C@H](N)c1ccc(C(CC2CCC2)N2CCN(C(=O)OC(C)(C)C)CC2)cc1] | 388 |

TABLE 3-continued
| Structural formulas of intermediates B-2 to B-68 | | |
|---|---|---|
| Intermediate | Compound structure | MS [M + H]$^+$ |
| B-8 | 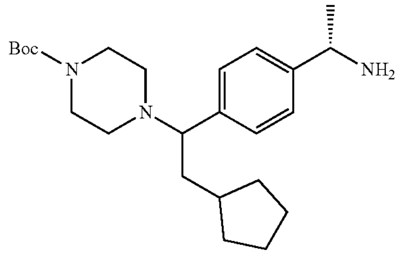 [SMILES: C[C@H](N)c1ccc(C(CC2CCCC2)N2CCN(C(=O)OC(C)(C)C)CC2)cc1] | 402 |
| B-9 | 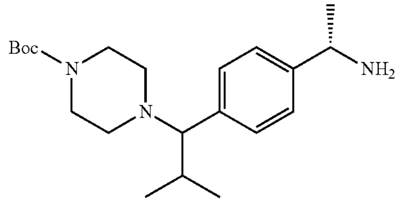 [SMILES: CC(C)C(c1ccc([C@H](C)N)cc1)N1CCN(C(=O)OC(C)(C)C)CC1] | 362 |
| B-10 | 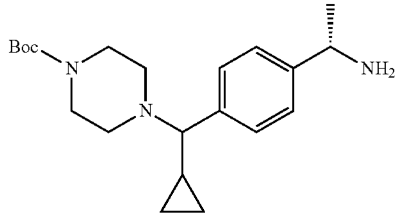 [SMILES: C[C@H](N)c1ccc(C(C2CC2)N2CCN(C(=O)OC(C)(C)C)CC2)cc1] | 360 |
| B-11 | 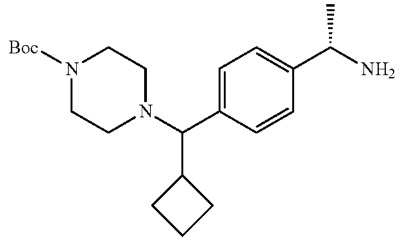 [SMILES: C[C@H](N)c1ccc(C(C2CCC2)N2CCN(C(=O)OC(C)(C)C)CC2)cc1] | 374 |
| B-12 | 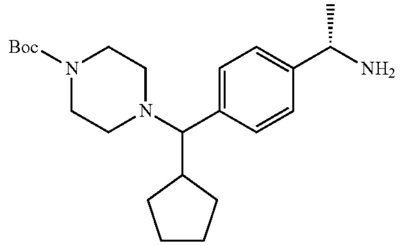 [SMILES: C[C@H](N)c1ccc(C(C2CCCC2)N2CCN(C(=O)OC(C)(C)C)CC2)cc1] | 388 |
| B-13 | 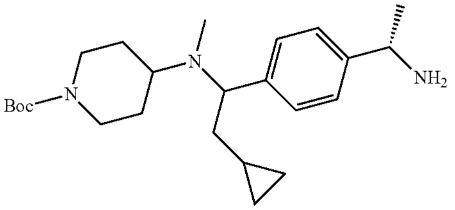 [SMILES: C[C@H](N)c1ccc(C(CC2CC2)N(C)C2CCN(C(=O)OC(C)(C)C)CC2)cc1] | 402 |

TABLE 3-continued
| Structural formulas of intermediates B-2 to B-68 | | |
|---|---|---|
| Intermediate | Compound structure | MS [M + H]+ |
| B-14 | 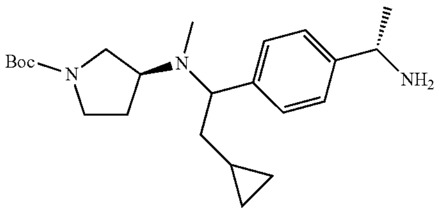 [SMILES: C[C@H](N)c1ccc(C(CC2CC2)N(C)[C@H]2CCN(C(=O)OC(C)(C)C)C2)cc1] | 388 |
| B-15 | 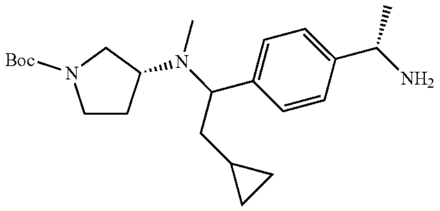 [SMILES: C[C@H](N)c1ccc(C(CC2CC2)N(C)[C@@H]2CCN(C(=O)OC(C)(C)C)C2)cc1] | 388 |
| B-16 | 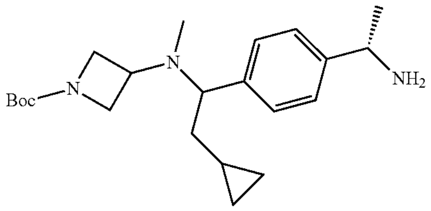 [SMILES: C[C@H](N)c1ccc(C(CC2CC2)N(C)C2CN(C(=O)OC(C)(C)C)C2)cc1] | 374 |
| B-17 | 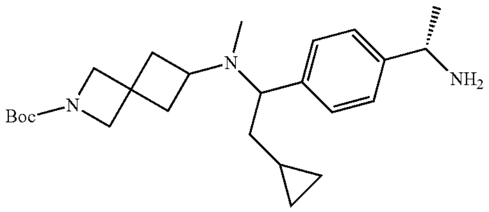 [SMILES: C[C@H](N)c1ccc(C(CC2CC2)N(C)C2CC3(C2)CN(C(=O)OC(C)(C)C)C3)cc1] | 414 |
| B-18 | 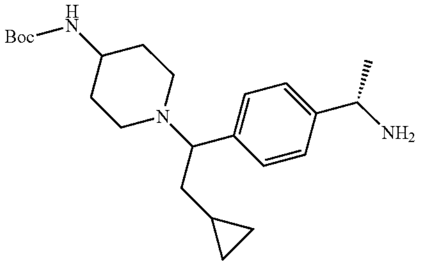 [SMILES: C[C@H](N)c1ccc(C(CC2CC2)N2CCC(NC(=O)OC(C)(C)C)CC2)cc1] | 388 |
| B-19 | 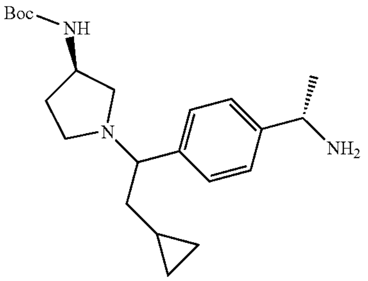 [SMILES: C[C@H](N)c1ccc(C(CC2CC2)N2CC[C@@H](NC(=O)OC(C)(C)C)C2)cc1] | 374 |

TABLE 3-continued
| Structural formulas of intermediates B-2 to B-68 | | |
|---|---|---|
| Intermediate | Compound structure | MS [M + H]+ |
| B-20 | 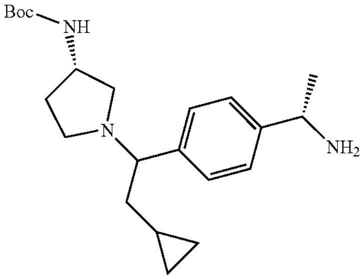 [SMILES: C[C@H](N)c1ccc(C(CC2CC2)N2CC[C@H](NC(=O)OC(C)(C)C)C2)cc1] | 374 |
| B-21 | 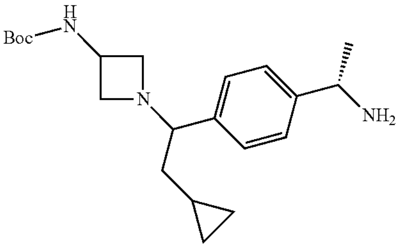 [SMILES: C[C@H](N)c1ccc(C(CC2CC2)N2CC(NC(=O)OC(C)(C)C)C2)cc1] | 360 |
| B-22 | 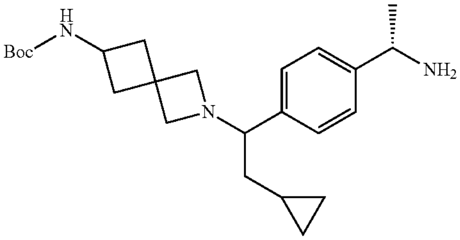 [SMILES: C[C@H](N)c1ccc(C(CC2CC2)N2CC3(CC(NC(=O)OC(C)(C)C)C3)C2)cc1] | 400 |
| B-23 | 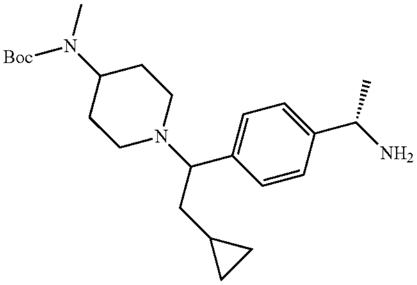 [SMILES: C[C@H](N)c1ccc(C(CC2CC2)N2CCC(N(C)C(=O)OC(C)(C)C)CC2)cc1] | 402 |
| B-24 | 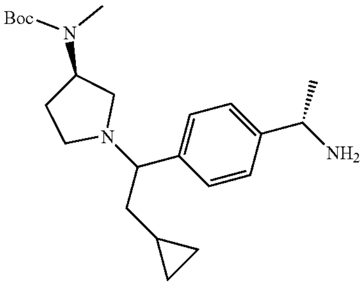 [SMILES: C[C@H](N)c1ccc(C(CC2CC2)N2CC[C@@H](N(C)C(=O)OC(C)(C)C)C2)cc1] | 388 |

TABLE 3-continued
| Structural formulas of intermediates B-2 to B-68 | | |
|---|---|---|
| Intermediate | Compound structure | MS [M + H]+ |
| B-25 | 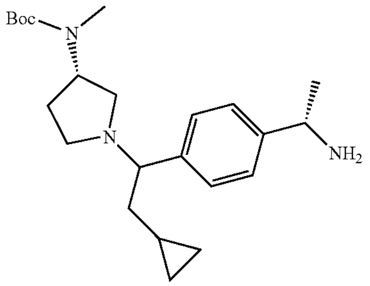 [SMILES: C[C@H](N)c1ccc(C(CC2CC2)N2CC[C@H](N(C)C(=O)OC(C)(C)C)C2)cc1] | 388 |
| B-26 | 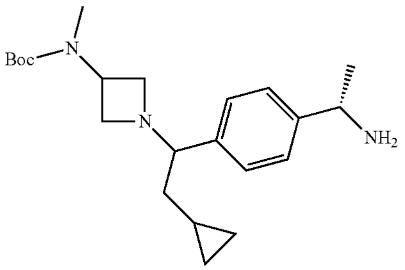 [SMILES: C[C@H](N)c1ccc(C(CC2CC2)N2CC(N(C)C(=O)OC(C)(C)C)C2)cc1] | 374 |
| B-27 | 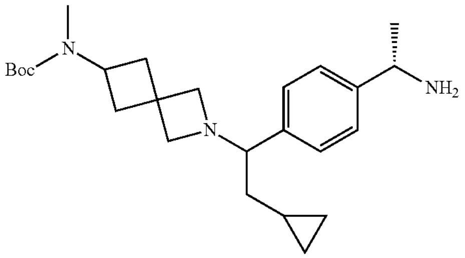 [SMILES: C[C@H](N)c1ccc(C(CC2CC2)N2CC3(CC(N(C)C(=O)OC(C)(C)C)C3)C2)cc1] | 414 |
| B-28 | 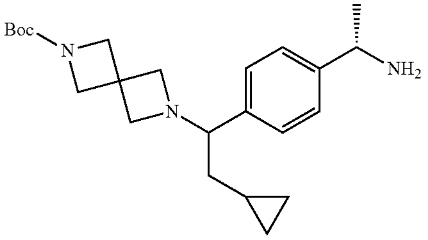 [SMILES: C[C@H](N)c1ccc(C(CC2CC2)N2CC3(CN(C(=O)OC(C)(C)C)C3)C2)cc1] | 386 |
| B-29 | 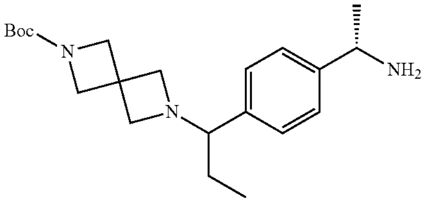 [SMILES: CCC(c1ccc([C@H](C)N)cc1)N1CC2(CN(C(=O)OC(C)(C)C)C2)C1] | 360 |
| B-30 | 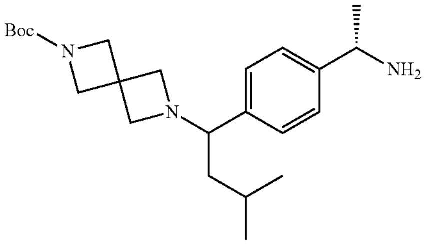 [SMILES: CC(C)CC(c1ccc([C@H](C)N)cc1)N1CC2(CN(C(=O)OC(C)(C)C)C2)C1] | 388 |

TABLE 3-continued
| Structural formulas of intermediates B-2 to B-68 | | |
|---|---|---|
| Intermediate | Compound structure | MS [M + H]+ |
| B-31 | 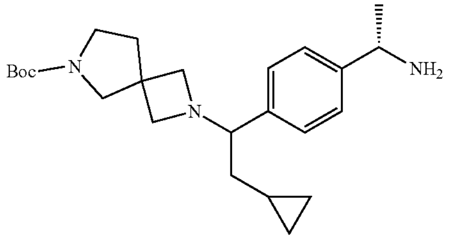 [SMILES: C[C@H](N)c1ccc(C(CC2CC2)N2CC3(CCN(C(=O)OC(C)(C)C)C3)C2)cc1] | 400 |
| B-32 | 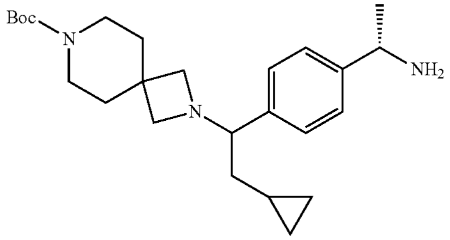 [SMILES: C[C@H](N)c1ccc(C(CC2CC2)N2CC3(CCN(C(=O)OC(C)(C)C)CC3)C2)cc1] | 414 |
| B-33 | 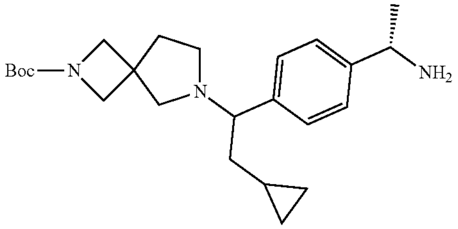 [SMILES: C[C@H](N)c1ccc(C(CC2CC2)N2CCC3(CN(C(=O)OC(C)(C)C)C3)C2)cc1] | 400 |
| B-34 | 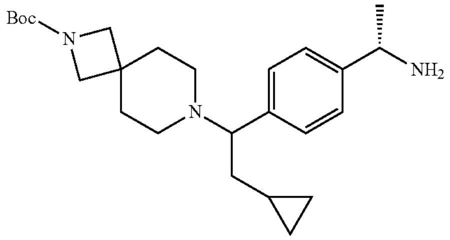 [SMILES: C[C@H](N)c1ccc(C(CC2CC2)N2CCC3(CC2)CN(C(=O)OC(C)(C)C)C3)cc1] | 414 |
| B-35 | 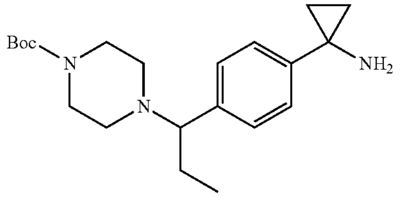 [SMILES: CCC(c1ccc(C2(N)CC2)cc1)N1CCN(C(=O)OC(C)(C)C)CC1] | 360 |
| B-36 | 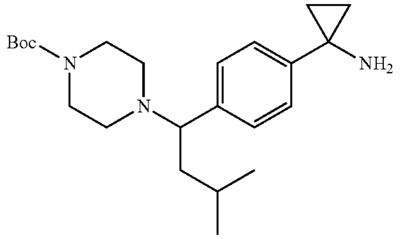 [SMILES: CC(C)CC(c1ccc(C2(N)CC2)cc1)N1CCN(C(=O)OC(C)(C)C)CC1] | 388 |

TABLE 3-continued
| Intermediate | Compound structure | MS [M + H]+ |
| --- | --- | --- |
| Structural formulas of intermediates B-2 to B-68 | | |
| B-37 | 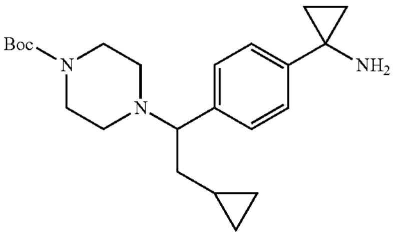 [SMILES: CC(C)(C)OC(=O)N1CCN(C(CC2CC2)c2ccc(C3(N)CC3)cc2)CC1] | 386 |
| B-38 | 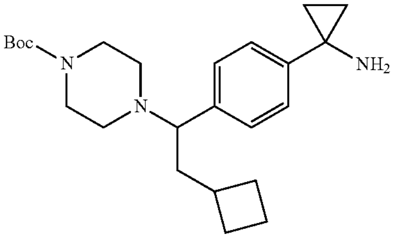 [SMILES: CC(C)(C)OC(=O)N1CCN(C(CC2CCC2)c2ccc(C3(N)CC3)cc2)CC1] | 400 |
| B-39 | 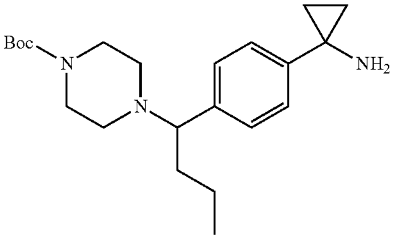 [SMILES: CCCC(c1ccc(C2(N)CC2)cc1)N1CCN(C(=O)OC(C)(C)C)CC1] | 374 |
| B-40 | 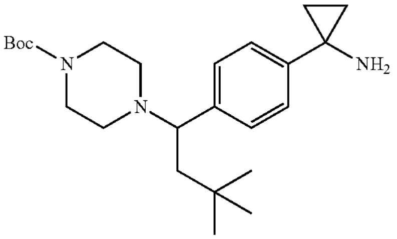 [SMILES: CC(C)(C)CC(c1ccc(C2(N)CC2)cc1)N1CCN(C(=O)OC(C)(C)C)CC1] | 402 |
| B-41 | 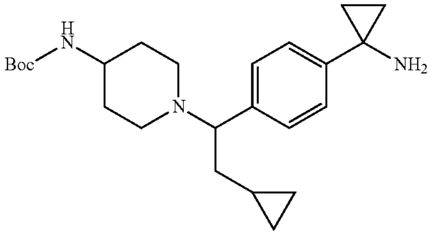 [SMILES: CC(C)(C)OC(=O)NC1CCN(C(CC2CC2)c2ccc(C3(N)CC3)cc2)CC1] | 400 |
| B-42 | 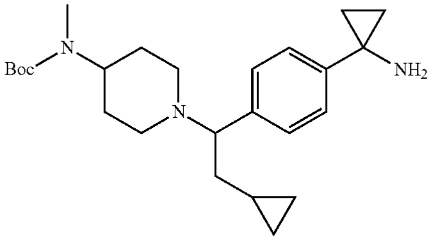 [SMILES: CN(C(=O)OC(C)(C)C)C1CCN(C(CC2CC2)c2ccc(C3(N)CC3)cc2)CC1] | 414 |

TABLE 3-continued
| Structural formulas of intermediates B-2 to B-68 | | |
|---|---|---|
| Intermediate | Compound structure | MS [M + H]+ |
| B-43 | 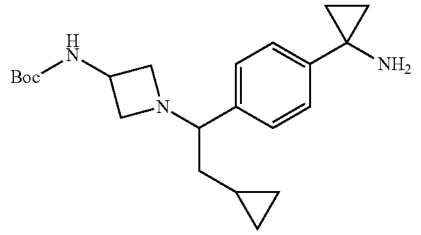 [SMILES: CC(C)(C)OC(=O)NC1CN(C(CC2CC2)c2ccc(C3(N)CC3)cc2)C1] | 372 |
| B-44 | 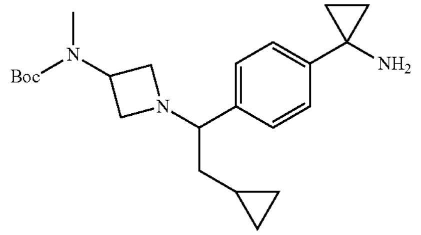 [SMILES: CN(C(=O)OC(C)(C)C)C1CN(C(CC2CC2)c2ccc(C3(N)CC3)cc2)C1] | 386 |
| B-45 | 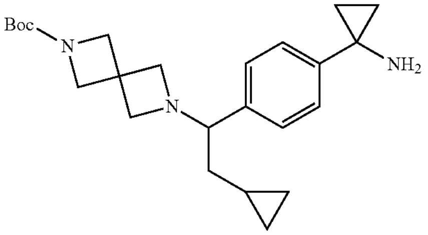 [SMILES: CC(C)(C)OC(=O)N1CC2(C1)CN(C(CC1CC1)c1ccc(C3(N)CC3)cc1)C2] | 398 |
| B-46 | 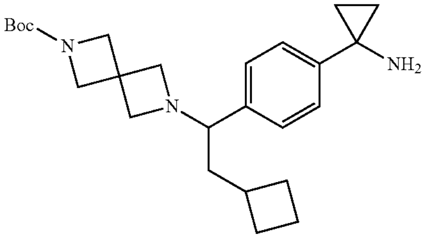 [SMILES: CC(C)(C)OC(=O)N1CC2(C1)CN(C(CC1CCC1)c1ccc(C3(N)CC3)cc1)C2] | 412 |
| B-47 | 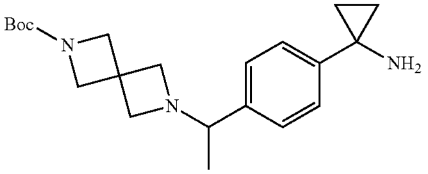 [SMILES: CC(c1ccc(C2(N)CC2)cc1)N1CC2(CN(C(=O)OC(C)(C)C)C2)C1] | 358 |
| B-48 | 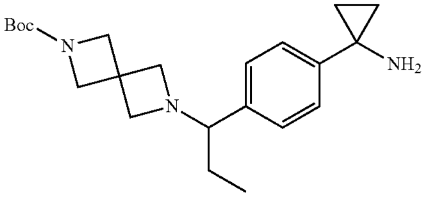 [SMILES: CCC(c1ccc(C2(N)CC2)cc1)N1CC2(CN(C(=O)OC(C)(C)C)C2)C1] | 372 |

TABLE 3-continued
| Structural formulas of intermediates B-2 to B-68 | | |
|---|---|---|
| Intermediate | Compound structure | MS [M + H]+ |
| B-49 | 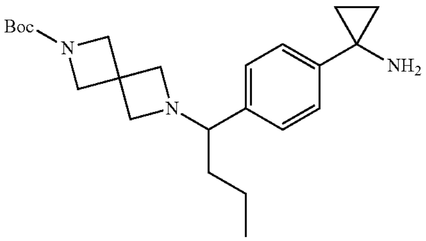 [SMILES: CCCC(c1ccc(C2(N)CC2)cc1)N1CC2(CN(C(=O)OC(C)(C)C)C2)C1] | 386 |
| B-50 | 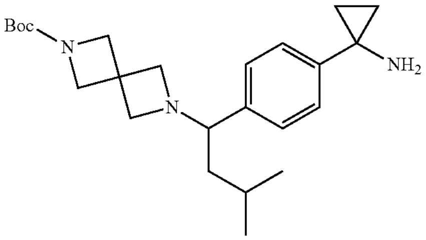 [SMILES: CC(C)CC(c1ccc(C2(N)CC2)cc1)N1CC2(CN(C(=O)OC(C)(C)C)C2)C1] | 400 |
| B-51 | 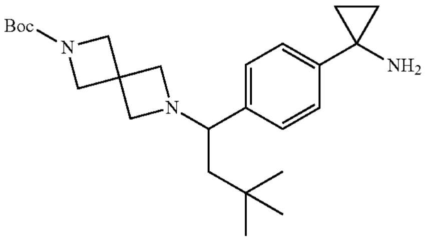 [SMILES: CC(C)(C)CC(c1ccc(C2(N)CC2)cc1)N1CC2(CN(C(=O)OC(C)(C)C)C2)C1] | 414 |
| B-52 | 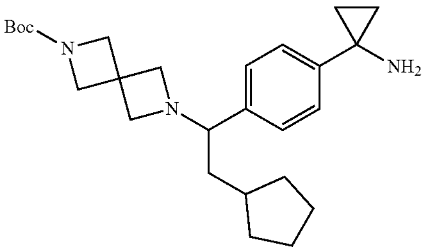 [SMILES: CC(C)(C)OC(=O)N1CC2(C1)CN(C(CC1CCCC1)c1ccc(C3(N)CC3)cc1)C2] | 426 |
| B-53 | 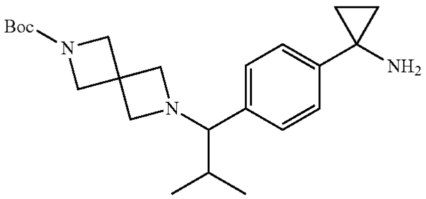 [SMILES: CC(C)C(c1ccc(C2(N)CC2)cc1)N1CC2(CN(C(=O)OC(C)(C)C)C2)C1] | 386 |
| B-54 | 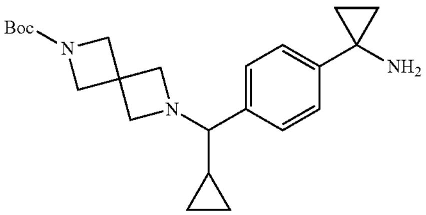 [SMILES: CC(C)(C)OC(=O)N1CC2(C1)CN(C(c1ccc(C3(N)CC3)cc1)C1CC1)C2] | 384 |

TABLE 3-continued
| Structural formulas of intermediates B-2 to B-68 | | |
|---|---|---|
| Intermediate | Compound structure | MS [M + H]+ |
| B-55 | 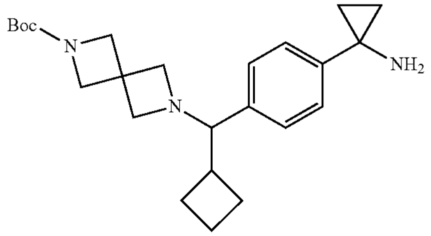 [SMILES: CC(C)(C)OC(=O)N1CC2(C1)CN(C(c1ccc(C3(N)CC3)cc1)C1CCC1)C2] | 398 |
| B-56 | 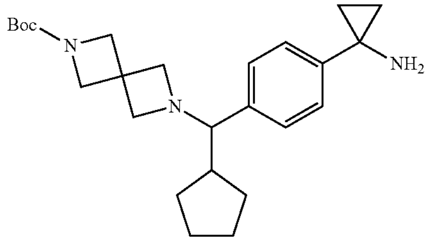 [SMILES: CC(C)(C)OC(=O)N1CC2(C1)CN(C(c1ccc(C3(N)CC3)cc1)C1CCCC1)C2] | 412 |
| B-57 | 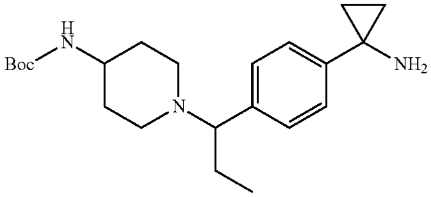 [SMILES: CCC(c1ccc(C2(N)CC2)cc1)N1CCC(NC(=O)OC(C)(C)C)CC1] | 374 |
| B-58 | 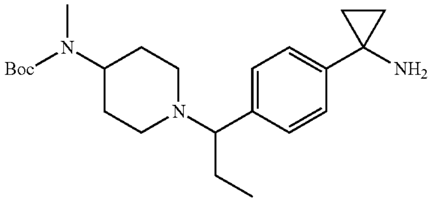 [SMILES: CCC(c1ccc(C2(N)CC2)cc1)N1CCC(N(C)C(=O)OC(C)(C)C)CC1] | 388 |
| B-59 | 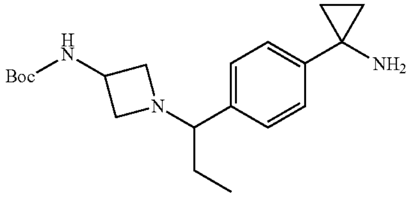 [SMILES: CCC(c1ccc(C2(N)CC2)cc1)N1CC(NC(=O)OC(C)(C)C)C1] | 346 |
| B-60 | 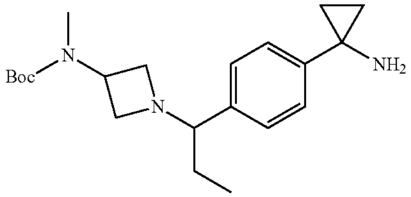 [SMILES: CCC(c1ccc(C2(N)CC2)cc1)N1CC(N(C)C(=O)OC(C)(C)C)C1] | 360 |

TABLE 3-continued
Structural formulas of intermediates B-2 to B-68
| Intermediate | Compound structure | MS $[M + H]^+$ |
| --- | --- | --- |
| B-61 | 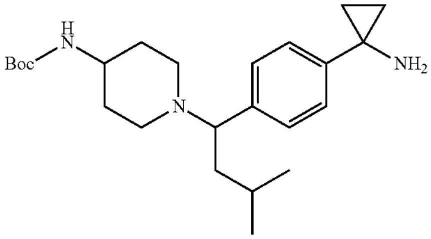 [SMILES: CC(C)CC(c1ccc(C2(N)CC2)cc1)N1CCC(NC(=O)OC(C)(C)C)CC1] | 402 |
| B-62 | 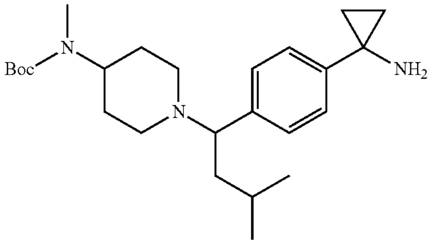 [SMILES: CC(C)CC(c1ccc(C2(N)CC2)cc1)N1CCC(N(C)C(=O)OC(C)(C)C)CC1] | 416 |
| B-63 | 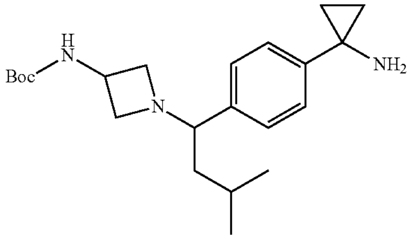 [SMILES: CC(C)CC(c1ccc(C2(N)CC2)cc1)N1CC(NC(=O)OC(C)(C)C)C1] | 374 |
| B-64 | 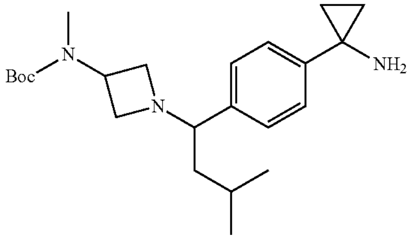 [SMILES: CC(C)CC(c1ccc(C2(N)CC2)cc1)N1CC(N(C)C(=O)OC(C)(C)C)C1] | 388 |
| B-65 | 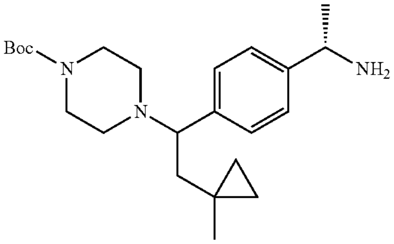 [SMILES: C[C@H](N)c1ccc(C(CC2(C)CC2)N2CCN(C(=O)OC(C)(C)C)CC2)cc1] | 388 |
| B-66 | 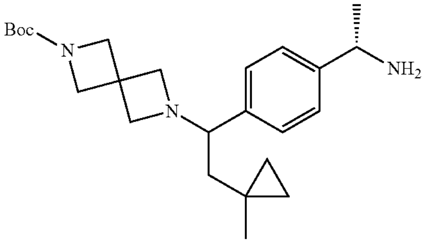 [SMILES: C[C@H](N)c1ccc(C(CC2(C)CC2)N2CC3(CN(C(=O)OC(C)(C)C)C3)C2)cc1] | 400 |

TABLE 3-continued

Structural formulas of intermediates B-2 to B-68

| Intermediate | Compound structure | MS [M + H]+ |
|---|---|---|
| B-67 | 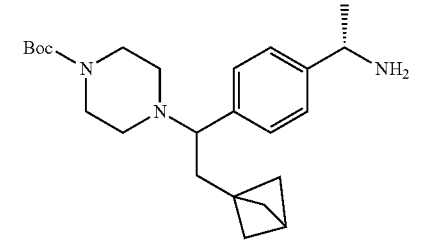 [SMILES: C[C@H](N)c1ccc(C(CC23CC(C2)C3)N2CCN(C(=O)OC(C)(C)C)CC2)cc1] | 400 |
| B-68 | 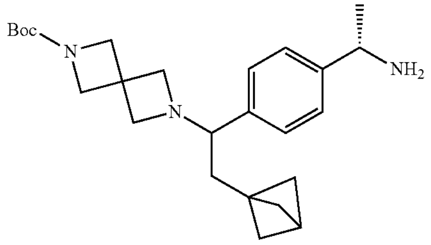 [SMILES: C[C@H](N)c1ccc(C(CC23CC(C2)C3)N2CC3(CN(C(=O)OC(C)(C)C)C3)C2)cc1] | 412 |

Example 1. Synthesis of 7-(((1S)-1-(4-(1-(4-acryloylpiperazin-1-yl)-2-cyclobutylethyl)-phenyl)ethyl) amino)-1-ethyl-1,4-dihydro-2H-pyrimido[4,5-d][1,3] oxazin-2-one (Compound 139)

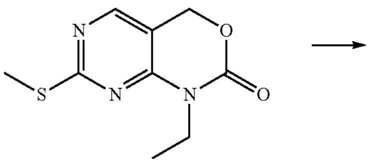

A-1

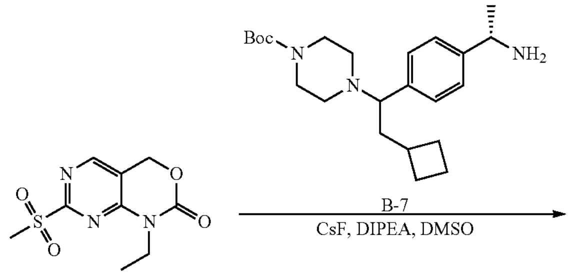

139-1

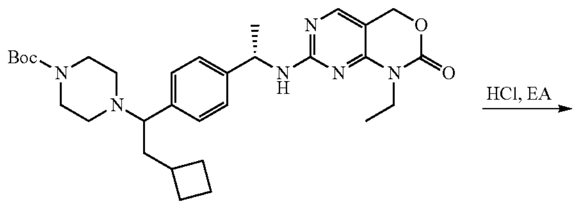

139-2

-continued

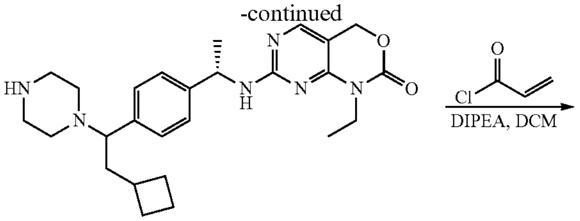

139-3

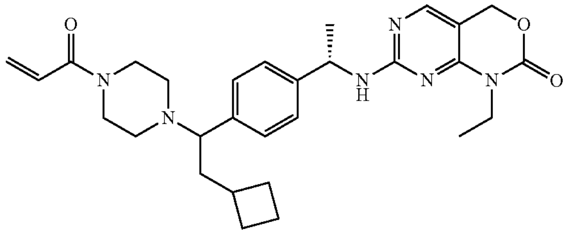

139

Step 1: Synthesis of Compound 139-1

Compound A-1 (2.85 g, 12.65 mmol) was dissolved in DCM (30 mL), m-CPBA (7.71 g, 37.95 mmol) was added in an ice bath, and the mixed solution was stirred at room temperature for 1 h. After the completion of the reaction as detected by LC-MS, the mixed solution was quenched with saturated $Na_2S_2O_3$ (40 mL) and sodium bicarbonate solution (20 mL). The mixed solution was stirred at room temperature for 30 min, followed by liquid separation, and then the aqueous phase was extracted with DCM (40 mL×2). The organic phases were combined, washed with saturated sodium chloride solution (40 mL), dried over anhydrous $Na_2SO_4$, filtered, and concentrated at reduced pressure to give a white solid product 139-1 (3.21 g, 99% yield). ESI-MS m/z: 258 $[M+H]^+$.

Step 2: Synthesis of Compound 139-2

Compound 139-1 (40 mg, 0.16 mmol) and compound B-7 (80 mg, crude, 0.16 mmol) were dissolved in dimethyl sulfoxide (10 mL), CsF (71 mg, 0.47 mmol) and DIPEA (30 mg, 0.23 mmol) were added, and the mixed solution was incubated at 60° C. for about 1 h for reaction. After the completion of the reaction as detected by LC-MS, water (10 mL) and EA (20 mL) were added to the mixed solution, followed by stirring and liquid separation, and then the aqueous phase was extracted with EA (10 mL). The organic phases were combined, washed with saturated sodium chloride solution (10 mL), dried over anhydrous $Na_2SO_4$, filtered and concentrated at reduced pressure to give a crude compound 139-2 as a yellow bubble solid (100 mg, 100% yield). ESI-MS m/z: 565 $[M+H]^+$.

Step 3: Synthesis of Compound 139-3

Compound 139-2 (100 mg, crude, 0.16 mmol) was dissolved in EA (5 mL), 4 M HCl/Diox (3 mL, 12 mmol) was added, and the mixed solution was stirred at room temperature for about 1 h. After the completion of the reaction as detected by LC-MS, the mixed solution was concentrated at reduced pressure to give a crude product as a brown solid (80 mg, 100% yield). ESI-MS m/z: 465 $[M+H]^+$.

Step 4: Synthesis of Compound 139

Compound 139-3 (74 mg, 0.16 mmol) was dissolved in DCM (5 mL), DIPEA (103 mg, 0.80 mmol) was added, and acryloyl chloride (14 mg, 0.16 mmol) was then added dropwise. The mixed solution was incubated at room temperature for about 10 min for reaction. After the completion of the reaction as detected by LC-MS, water (10 mL) was added. The mixed solution was extracted with DCM (10 mL×2), the organic phases were combined and concentrated to dryness by rotary evaporation, and the residue was purified by pre-TLC to give a compound 139 as a light yellow solid (12 mg, 14% yield).

$^1H$ NMR (400 MHz, $CDCl_3$) δ: 7.88 (s, 1H), 7.25 (d, J=7.1 Hz, 2H), 7.08 (d, J=7.8 Hz, 2H), 6.46 (dd, J=16.8, 10.5 Hz, 1H), 6.20 (dd, J=16.9, 2.0 Hz, 1H), 5.61 (dd, J=10.5, 2.0 Hz, 1H), 5.05 (s, 2H), 3.92 (td, J=19.2, 16.3, 9.5 Hz, 2H), 3.68-3.46 (m, 4H), 3.46 (s, 1H), 3.20 (dd, J=9.3, 4.7 Hz, 1H), 2.33 (s, 4H), 2.04-1.64 (m, 9H), 1.53 (d, J=6.9 Hz, 3H), 1.07 (s, 3H); ESI-MS m/z: 519 $[M+H]^+$.

Examples 2-105. Synthesis of Compounds 1-84, 140-159

By the procedures similar to those in the synthesis of compound 139, the target compounds 1-84 and 140-159 in Table 4 may be obtained with different intermediates as starting materials.

TABLE 4

Compounds 1-84 and 140-159

| Compound | Structural formula | MS: $[M+H]^+$ |
|---|---|---|
| 1 | 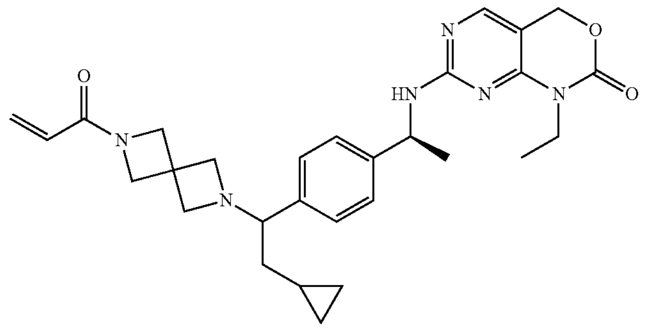 [SMILES: C=CC(=O)N1CC2(C1)CN(C(CC1CC1)c1ccc([C@H](C)Nc3ncc4c(n3)N(CC)C(=O)OC4)cc1)C2] | 517 |
| 2 | 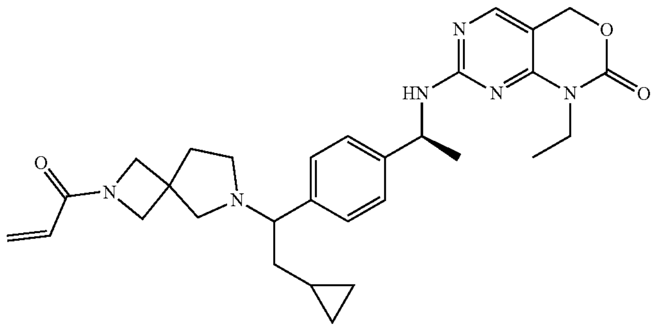 [SMILES: C=CC(=O)N1CC2(CCN(C(CC3CC3)c3ccc([C@H](C)Nc4ncc5c(n4)N(CC)C(=O)OC5)cc3)C2)C1] | 531 |

TABLE 4-continued
| Compounds 1-84 and 140-159 | | |
|---|---|---|
| Compound | Structural formula | MS: [M + H]+ |
| 3 | 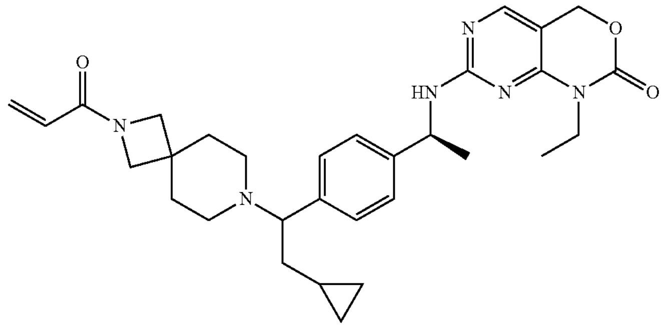 [SMILES: C=CC(=O)N1CC2(CCN(C(CC3CC3)c3ccc([C@H](C)Nc4ncc5c(n4)N(CC)C(=O)OC5)cc3)CC2)C1] | 545 |
| 4 | 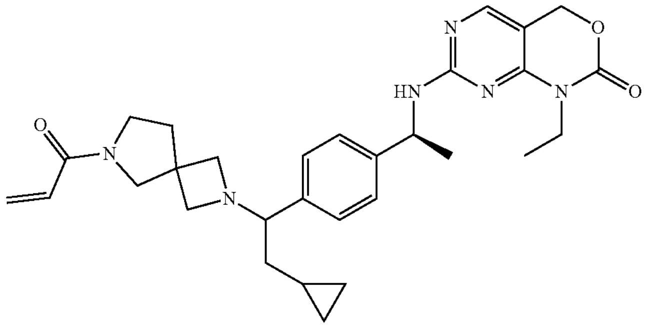 [SMILES: C=CC(=O)N1CCC2(C1)CN(C(CC1CC1)c1ccc([C@H](C)Nc3ncc4c(n3)N(CC)C(=O)OC4)cc1)C2] | 531 |
| 5 | 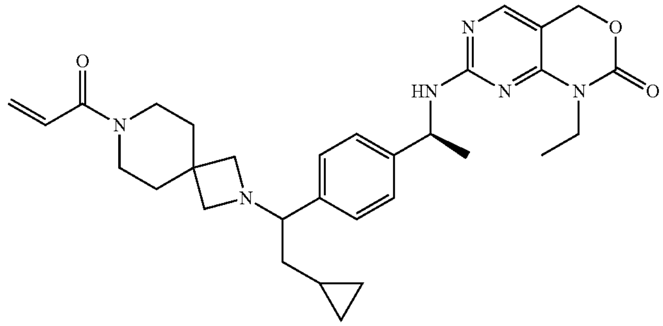 [SMILES: C=CC(=O)N1CCC2(CC1)CN(C(CC1CC1)c1ccc([C@H](C)Nc3ncc4c(n3)N(CC)C(=O)OC4)cc1)C2] | 545 |
| 6 | 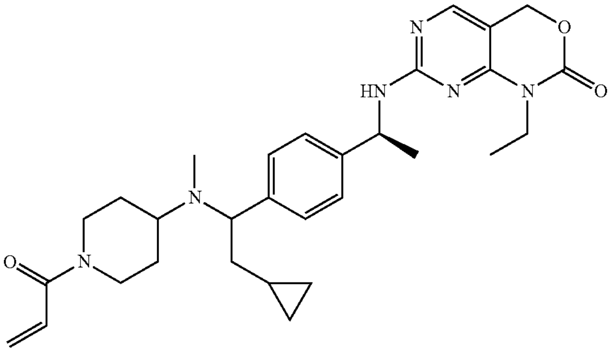 [SMILES: C=CC(=O)N1CCC(N(C)C(CC2CC2)c2ccc([C@H](C)Nc3ncc4c(n3)N(CC)C(=O)OC4)cc2)CC1] | 533 |

TABLE 4-continued
| Compounds 1-84 and 140-159 | | |
|---|---|---|
| Compound | Structural formula | MS: [M + H]$^+$ |
| 7 | 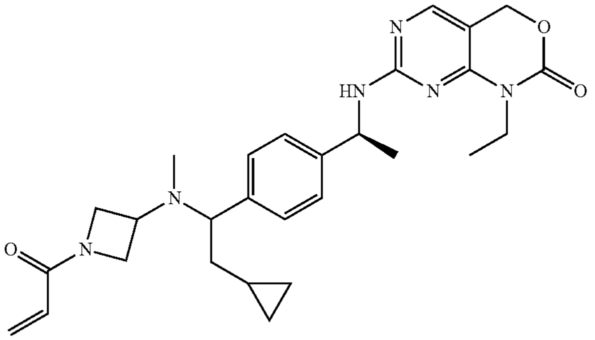 [SMILES: C=CC(=O)N1CC(N(C)C(CC2CC2)c2ccc([C@H](C)Nc3ncc4c(n3)N(CC)C(=O)OC4)cc2)C1] | 505 |
| 8 | 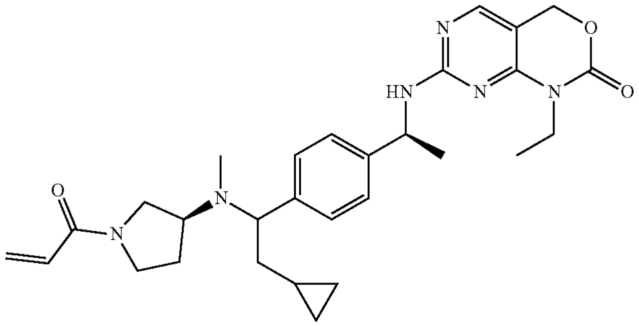 [SMILES: C=CC(=O)N1CC[C@H](N(C)C(CC2CC2)c2ccc([C@H](C)Nc3ncc4c(n3)N(CC)C(=O)OC4)cc2)C1] | 519 |
| 9 | 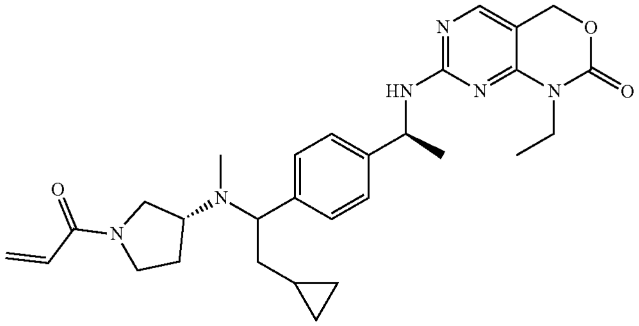 [SMILES: C=CC(=O)N1CC[C@@H](N(C)C(CC2CC2)c2ccc([C@H](C)Nc3ncc4c(n3)N(CC)C(=O)OC4)cc2)C1] | 519 |
| 10 | 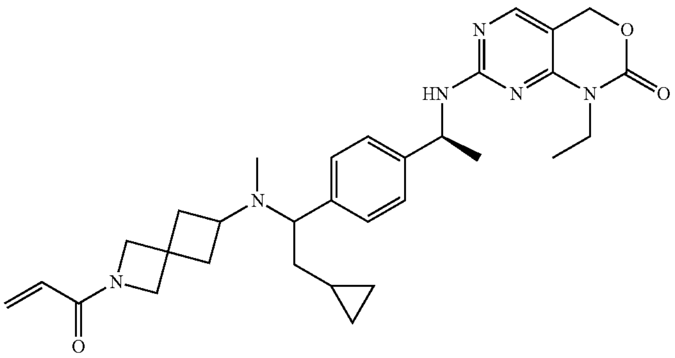 [SMILES: C=CC(=O)N1CC2(CC(N(C)C(CC3CC3)c3ccc([C@H](C)Nc4ncc5c(n4)N(CC)C(=O)OC5)cc3)C2)C1] | 545 |

TABLE 4-continued
| Compounds 1-84 and 140-159 | | |
|---|---|---|
| Compound | Structural formula | MS: [M + H]+ |
| 11 | 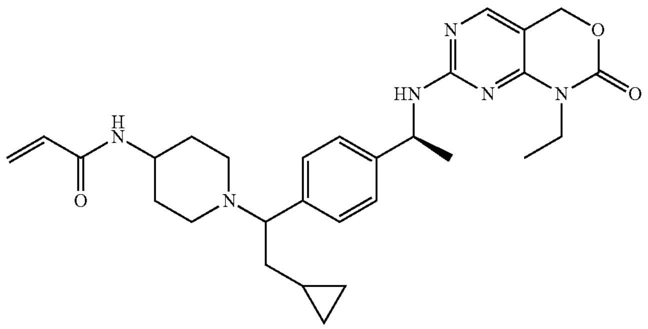 | 519 |
| 12 | 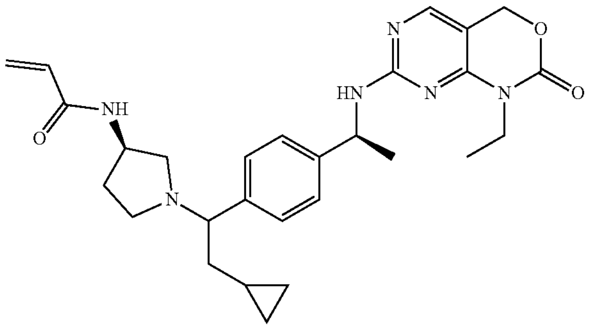 [SMILES: C=CC(=O)N[C@@H]1CCN(C(CC2CC2)c2ccc([C@H](C)Nc3ncc4c(n3)N(CC)C(=O)OC4)cc2)C1] | 505 |
| 13 | 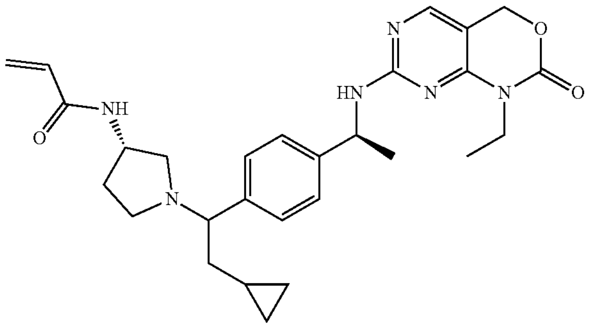 [SMILES: C=CC(=O)N[C@H]1CCN(C(CC2CC2)c2ccc([C@H](C)Nc3ncc4c(n3)N(CC)C(=O)OC4)cc2)C1] | 505 |
| 14 | 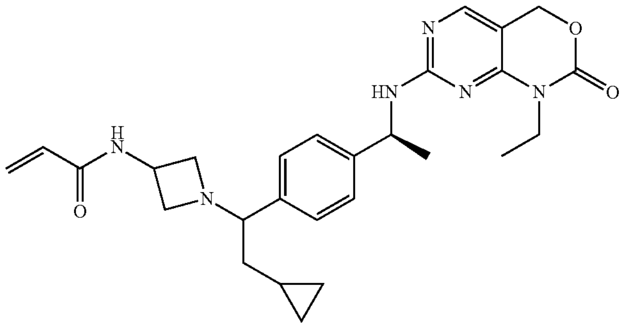 [SMILES: C=CC(=O)NC1CN(C(CC2CC2)c2ccc([C@H](C)Nc3ncc4c(n3)N(CC)C(=O)OC4)cc2)C1] | 491 |

TABLE 4-continued
| Compounds 1-84 and 140-159 | | |
|---|---|---|
| Compound | Structural formula | MS: [M + H]+ |
| 15 | 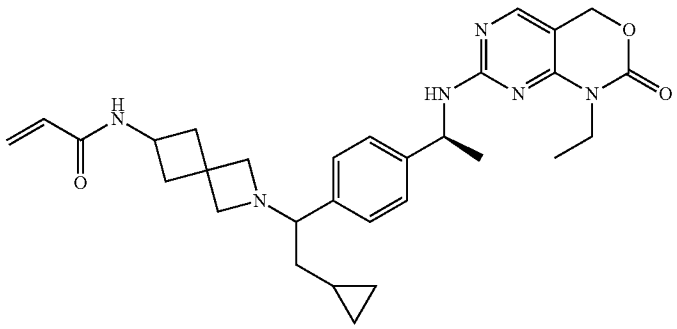 [SMILES: C=CC(=O)NC1CC2(C1)CN(C(CC1CC1)c1ccc([C@H](C)Nc3ncc4c(n3)N(CC)C(=O)OC4)cc1)C2] | 531 |
| 16 | 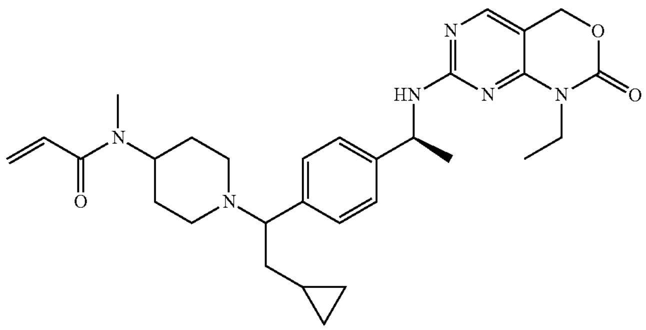 [SMILES: C=CC(=O)N(C)C1CCN(C(CC2CC2)c2ccc([C@H](C)Nc3ncc4c(n3)N(CC)C(=O)OC4)cc2)CC1] | 533 |
| 17 | 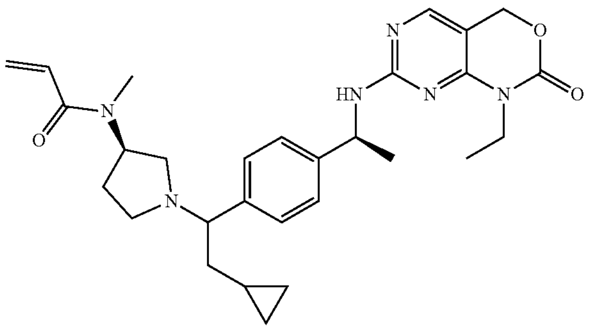 [SMILES: C=CC(=O)N(C)[C@@H]1CCN(C(CC2CC2)c2ccc([C@H](C)Nc3ncc4c(n3)N(CC)C(=O)OC4)cc2)C1] | 519 |
| 18 | 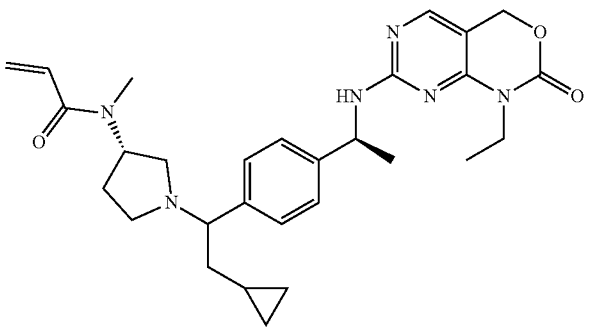 [SMILES: C=CC(=O)N(C)[C@H]1CCN(C(CC2CC2)c2ccc([C@H](C)Nc3ncc4c(n3)N(CC)C(=O)OC4)cc2)C1] | 519 |

TABLE 4-continued
| Compound | Structural formula | MS: [M + H]+ |
| --- | --- | --- |
| Compounds 1-84 and 140-159 | | |
| 19 | 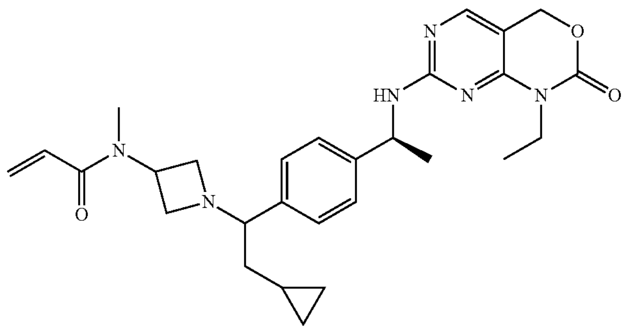 [SMILES: C=CC(=O)N(C)C1CN(C(CC2CC2)c2ccc([C@H](C)Nc3ncc4c(n3)N(CC)C(=O)OC4)cc2)C1] | 505 |
| 20 | 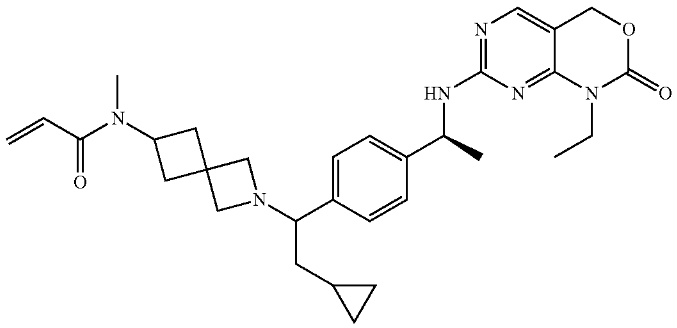 [SMILES: C=CC(=O)N(C)C1CC2(C1)CN(C(CC1CC1)c1ccc([C@H](C)Nc3ncc4c(n3)N(CC)C(=O)OC4)cc1)C2] | 545 |
| 21 | 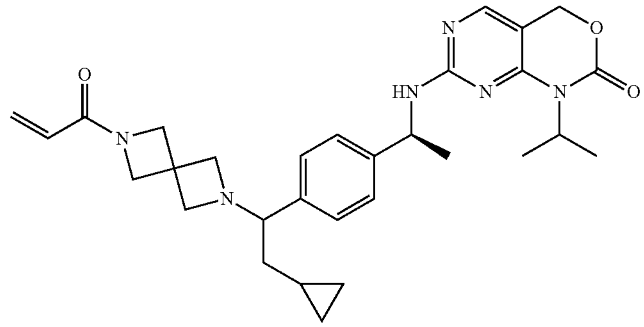 [SMILES: C=CC(=O)N1CC2(C1)CN(C(CC1CC1)c1ccc([C@H](C)Nc3ncc4c(n3)N(C(C)C)C(=O)OC4)cc1)C2] | 531 |
| 22 | 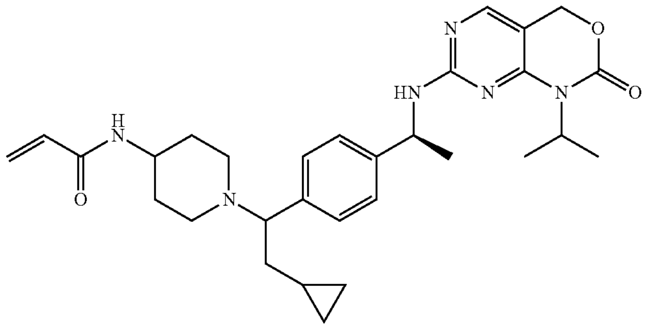 [SMILES: C=CC(=O)NC1CCN(C(CC2CC2)c2ccc([C@H](C)Nc3ncc4c(n3)N(C(C)C)C(=O)OC4)cc2)CC1] | 533 |

TABLE 4-continued
| Compounds 1-84 and 140-159 | | |
|---|---|---|
| Compound | Structural formula | MS: $[M + H]^+$ |
| 23 | 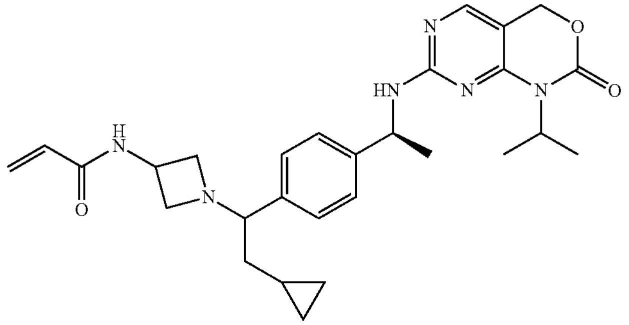 [SMILES: C=CC(=O)NC1CN(C(CC2CC2)c2ccc([C@H](C)Nc3ncc4c(n3)N(C(C)C)C(=O)OC4)cc2)C1] | 505 |
| 24 | 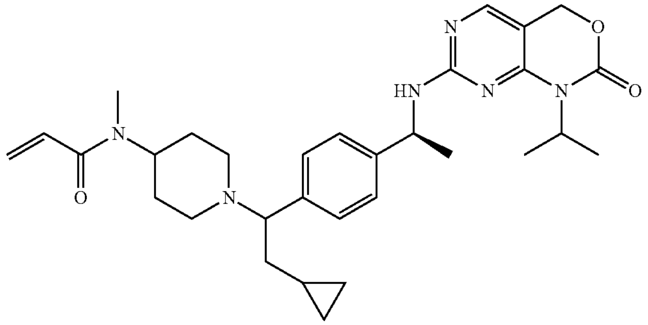 [SMILES: C=CC(=O)N(C)C1CCN(C(CC2CC2)c2ccc([C@H](C)Nc3ncc4c(n3)N(C(C)C)C(=O)OC4)cc2)CC1] | 547 |
| 25 | 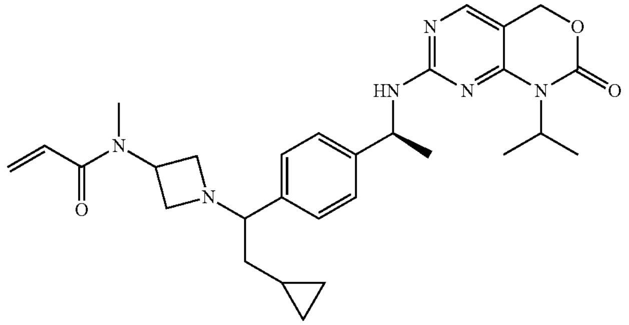 [SMILES: C=CC(=O)N(C)C1CN(C(CC2CC2)c2ccc([C@H](C)Nc3ncc4c(n3)N(C(C)C)C(=O)OC4)cc2)C1] | 519 |
| 26 | 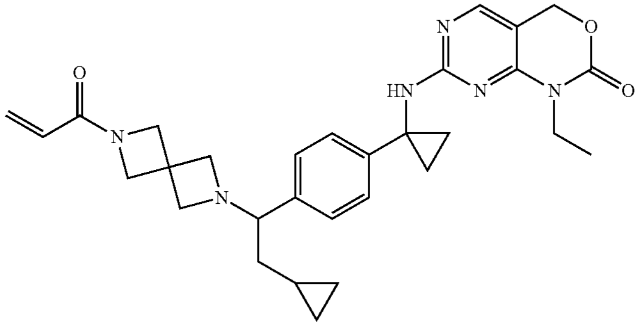 [SMILES: C=CC(=O)N1CC2(C1)CN(C(CC1CC1)c1ccc(C3(Nc4ncc5c(n4)N(CC)C(=O)OC5)CC3)cc1)C2] | 529 |

TABLE 4-continued
| Compounds 1-84 and 140-159 | | |
|---|---|---|
| Compound | Structural formula | MS: [M + H]$^+$ |
| 27 | 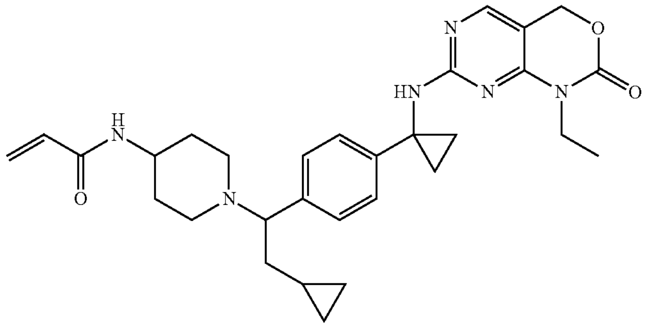 [SMILES: C=CC(=O)NC1CCN(C(CC2CC2)c2ccc(C3(Nc4ncc5c(n4)N(CC)C(=O)OC5)CC3)cc2)CC1] | 531 |
| 28 | 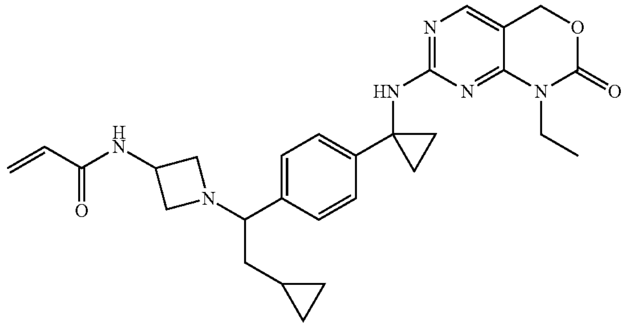 [SMILES: C=CC(=O)NC1CN(C(CC2CC2)c2ccc(C3(Nc4ncc5c(n4)N(CC)C(=O)OC5)CC3)cc2)C1] | 503 |
| 29 | 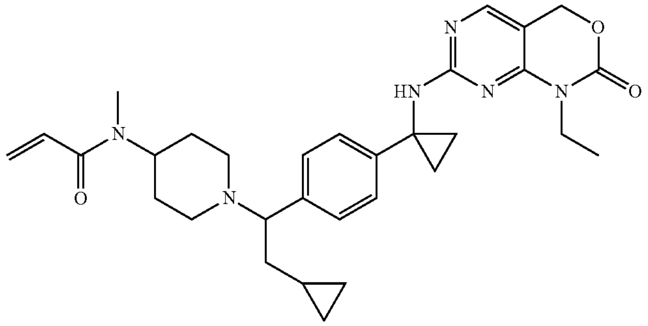 [SMILES: C=CC(=O)N(C)C1CCN(C(CC2CC2)c2ccc(C3(Nc4ncc5c(n4)N(CC)C(=O)OC5)CC3)cc2)CC1] | 545 |
| 30 | 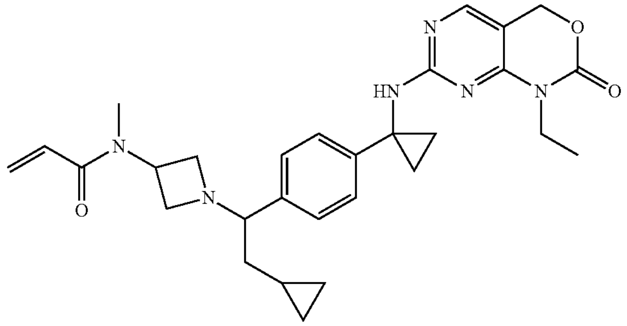 [SMILES: C=CC(=O)N(C)C1CN(C(CC2CC2)c2ccc(C3(Nc4ncc5c(n4)N(CC)C(=O)OC5)CC3)cc2)C1] | 517 |

TABLE 4-continued
| Compounds 1-84 and 140-159 | | |
|---|---|---|
| Compound | Structural formula | MS: [M + H]$^+$ |
| 31 | 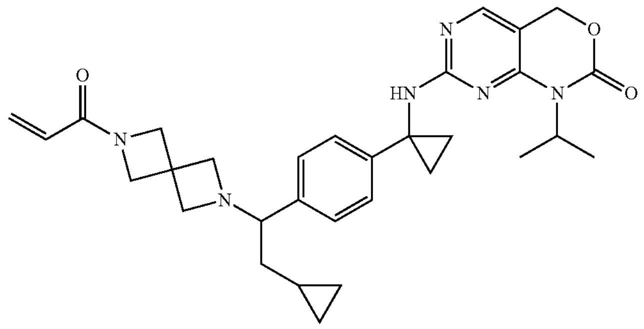 [SMILES: C=CC(=O)N1CC2(C1)CN(C(CC1CC1)c1ccc(C3(Nc4ncc5c(n4)N(C(C)C)C(=O)OC5)CC3)cc1)C2] | 543 |
| 32 | 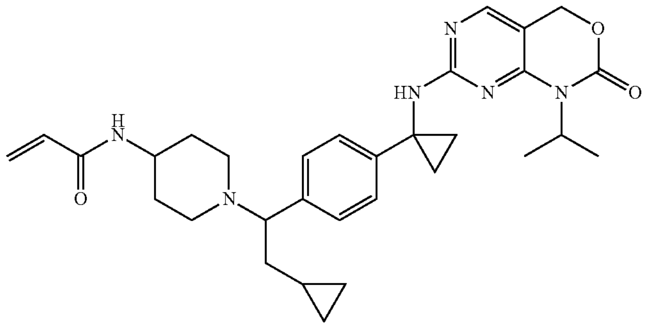 [SMILES: C=CC(=O)NC1CCN(C(CC2CC2)c2ccc(C3(Nc4ncc5c(n4)N(C(C)C)C(=O)OC5)CC3)cc2)CC1] | 545 |
| 33 | 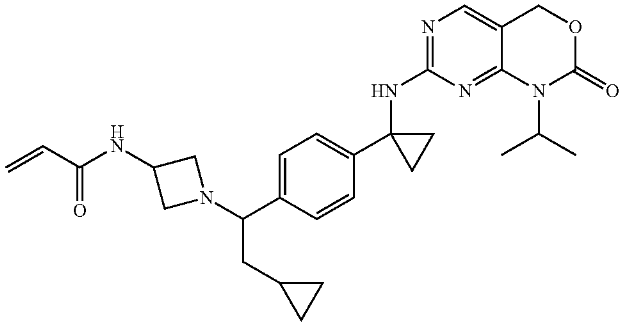 [SMILES: C=CC(=O)NC1CN(C(CC2CC2)c2ccc(C3(Nc4ncc5c(n4)N(C(C)C)C(=O)OC5)CC3)cc2)C1] | 517 |
| 34 | 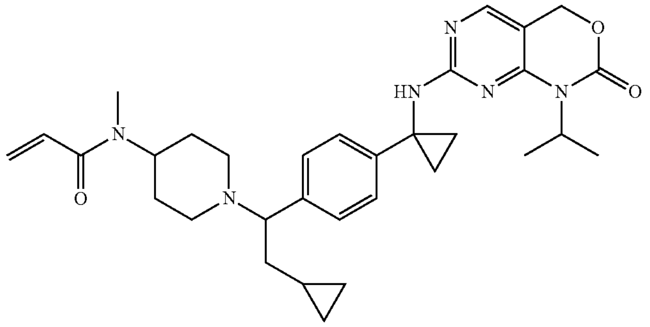 [SMILES: C=CC(=O)N(C)C1CCN(C(CC2CC2)c2ccc(C3(Nc4ncc5c(n4)N(C(C)C)C(=O)OC5)CC3)cc2)CC1] | 559 |

TABLE 4-continued
| Compounds 1-84 and 140-159 | | |
|---|---|---|
| Compound | Structural formula | MS: $[M + H]^+$ |
| 35 | 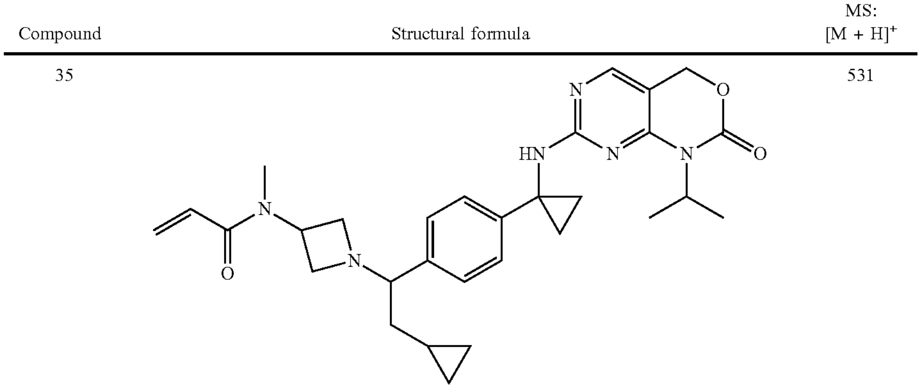 | 531 |
| 36 | 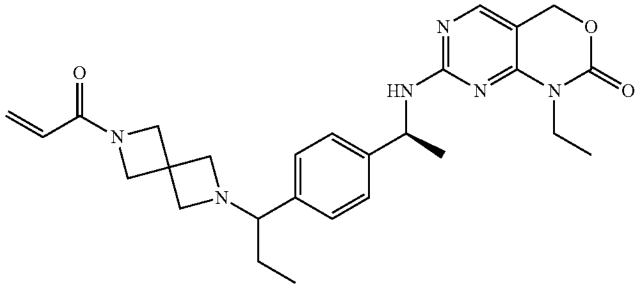 [SMILES: C=CC(=O)N1CC2(C1)CN(C(CC)c1ccc([C@H](C)Nc3ncc4c(n3)N(CC)C(=O)OC4)cc1)C2] | 491 |
| 37 | 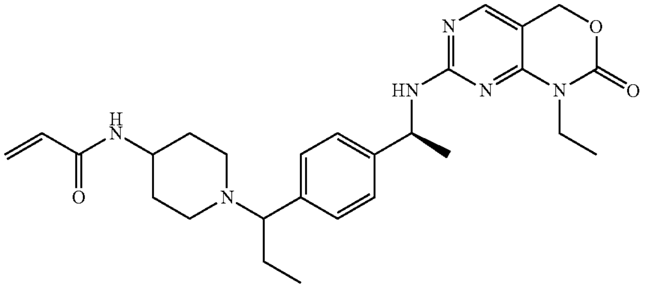 [SMILES: C=CC(=O)NC1CCN(C(CC)c2ccc([C@H](C)Nc3ncc4c(n3)N(CC)C(=O)OC4)cc2)CC1] | 493 |
| 38 | 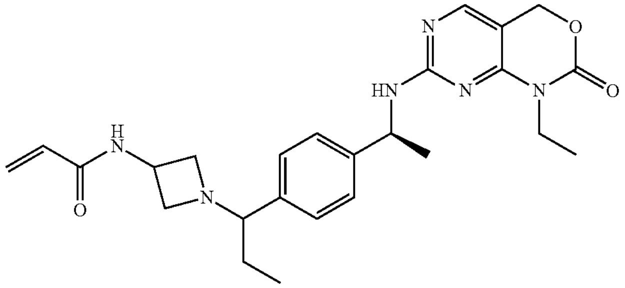 [SMILES: C=CC(=O)NC1CN(C(CC)c2ccc([C@H](C)Nc3ncc4c(n3)N(CC)C(=O)OC4)cc2)C1] | 465 |
| 39 | 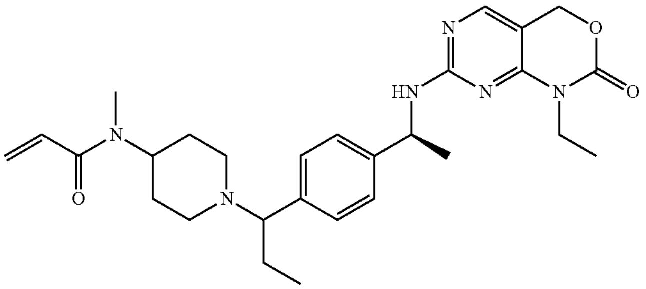 [SMILES: C=CC(=O)N(C)C1CCN(C(CC)c2ccc([C@H](C)Nc3ncc4c(n3)N(CC)C(=O)OC4)cc2)CC1] | 507 |

TABLE 4-continued
| Compounds 1-84 and 140-159 | | |
|---|---|---|
| Compound | Structural formula | MS: [M + H]+ |
| 40 | 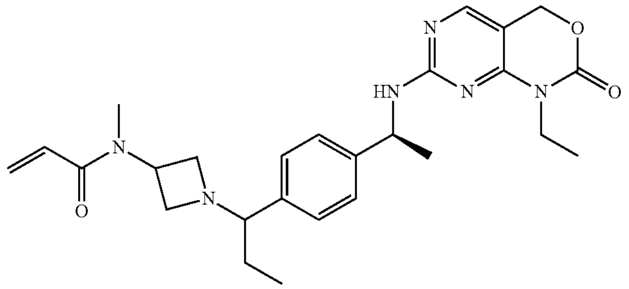 [SMILES: C=CC(=O)N(C)C1CN(C(CC)c2ccc([C@H](C)Nc3ncc4c(n3)N(CC)C(=O)OC4)cc2)C1] | 479 |
| 41 | 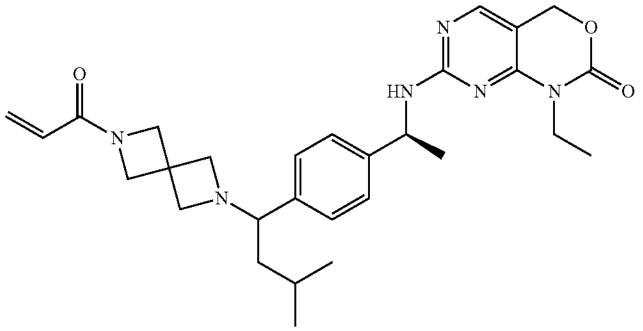 [SMILES: C=CC(=O)N1CC2(C1)CN(C(CC(C)C)c1ccc([C@H](C)Nc3ncc4c(n3)N(CC)C(=O)OC4)cc1)C2] | 519 |
| 42 | 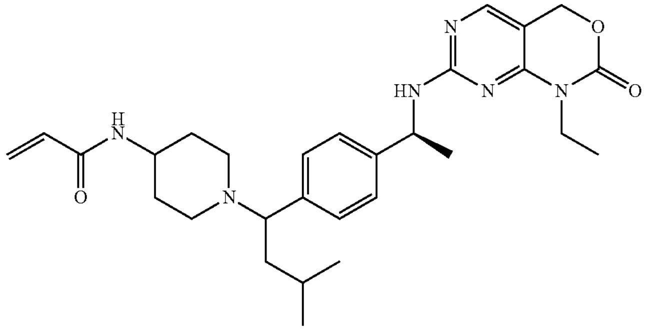 [SMILES: C=CC(=O)NC1CCN(C(CC(C)C)c2ccc([C@H](C)Nc3ncc4c(n3)N(CC)C(=O)OC4)cc2)CC1] | 521 |
| 43 | 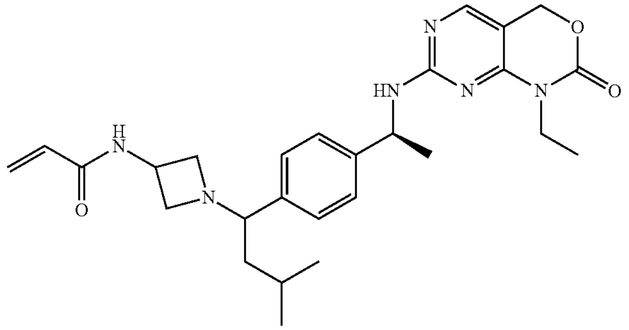 [SMILES: C=CC(=O)NC1CN(C(CC(C)C)c2ccc([C@H](C)Nc3ncc4c(n3)N(CC)C(=O)OC4)cc2)C1] | 493 |

TABLE 4-continued
| Compound | Structural formula | MS: [M + H]+ |
|---|---|---|
| | Compounds 1-84 and 140-159 | |
| 44 | 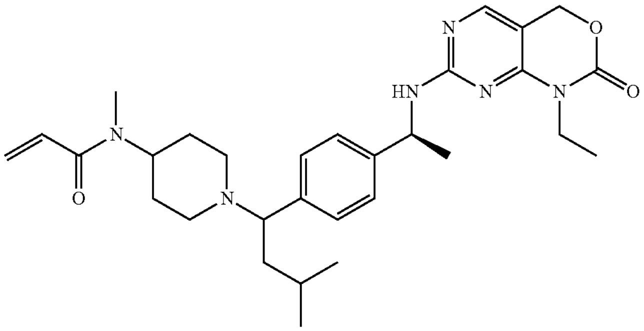 [SMILES: C=CC(=O)N(C)C1CCN(C(CC(C)C)c2ccc([C@H](C)Nc3ncc4c(n3)N(CC)C(=O)OC4)cc2)CC1] | 535 |
| 45 | 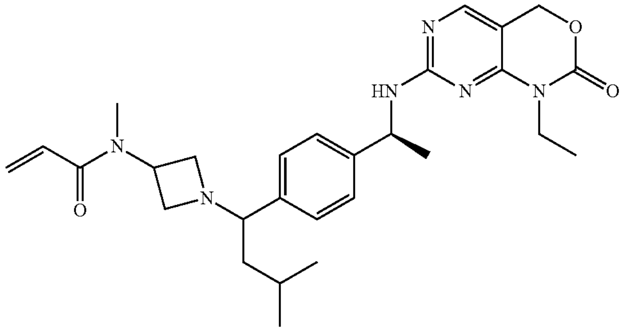 [SMILES: C=CC(=O)N(C)C1CN(C(CC(C)C)c2ccc([C@H](C)Nc3ncc4c(n3)N(CC)C(=O)OC4)cc2)C1] | 507 |
| 46 | 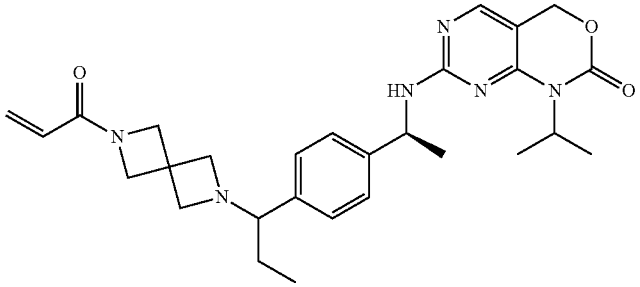 [SMILES: C=CC(=O)N1CC2(C1)CN(C(CC)c1ccc([C@H](C)Nc3ncc4c(n3)N(C(C)C)C(=O)OC4)cc1)C2] | 505 |
| 47 | 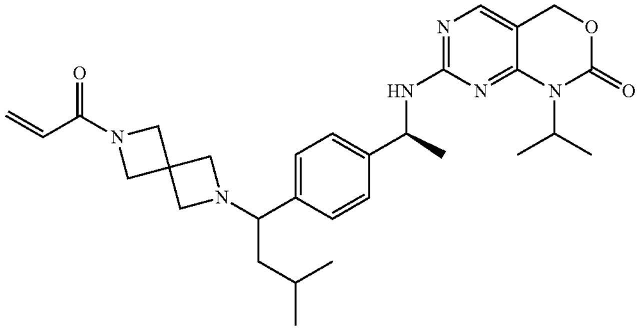 [SMILES: C=CC(=O)N1CC2(C1)CN(C(CC(C)C)c1ccc([C@H](C)Nc3ncc4c(n3)N(C(C)C)C(=O)OC4)cc1)C2] | 533 |

TABLE 4-continued
| Compounds 1-84 and 140-159 | | |
|---|---|---|
| Compound | Structural formula | MS: [M + H]+ |
| 48 | 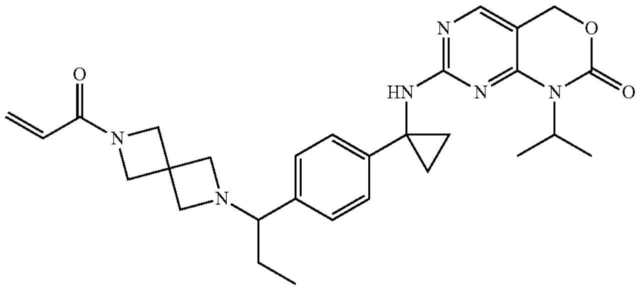 [SMILES: C=CC(=O)N1CC2(C1)CN(C(CC)c1ccc(C3(Nc4ncc5c(n4)N(C(C)C)C(=O)OC5)CC3)cc1)C2] | 517 |
| 49 | 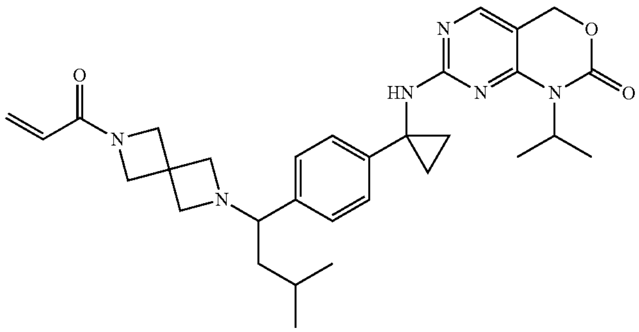 [SMILES: C=CC(=O)N1CC2(C1)CN(C(CC(C)C)c1ccc(C3(Nc4ncc5c(n4)N(C(C)C)C(=O)OC5)CC3)cc1)C2] | 545 |
| 50 | 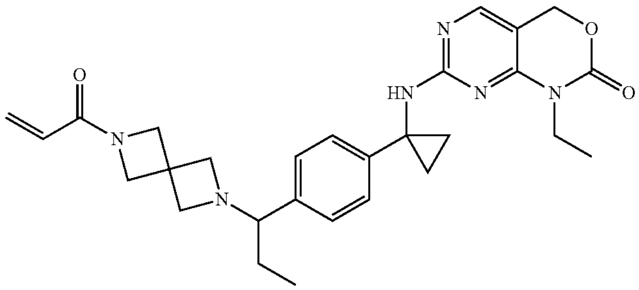 [SMILES: C=CC(=O)N1CC2(C1)CN(C(CC)c1ccc(C3(Nc4ncc5c(n4)N(CC)C(=O)OC5)CC3)cc1)C2] | 503 |
| 51 | 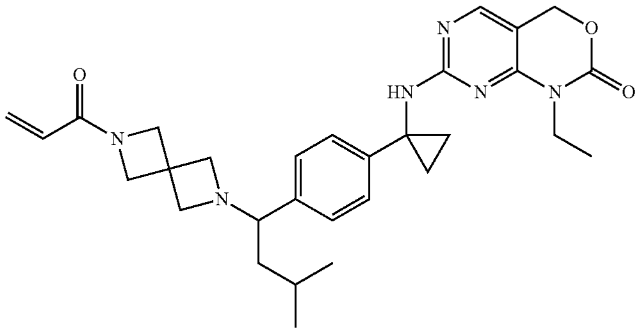 [SMILES: C=CC(=O)N1CC2(C1)CN(C(CC(C)C)c1ccc(C3(Nc4ncc5c(n4)N(CC)C(=O)OC5)CC3)cc1)C2] | 531 |

TABLE 4-continued
| Compound | Structural formula | MS: [M + H]+ |
| --- | --- | --- |
| Compounds 1-84 and 140-159 | | |
| 52 | 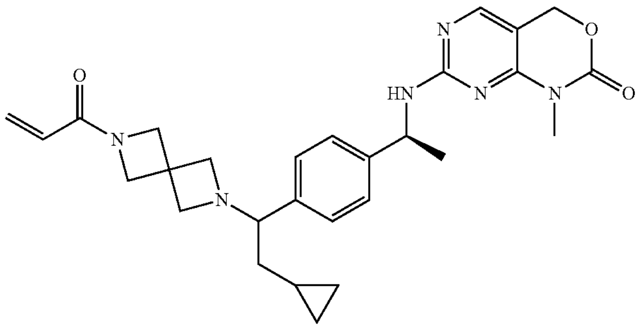 [SMILES: C=CC(=O)N1CC2(C1)CN(C(CC1CC1)c1ccc([C@H](C)Nc3ncc4c(n3)N(C)C(=O)OC4)cc1)C2] | 503 |
| 53 | 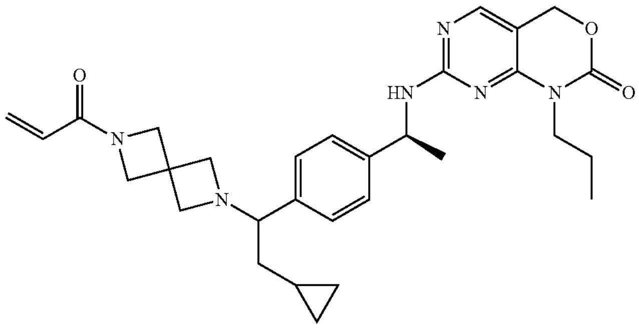 [SMILES: C=CC(=O)N1CC2(C1)CN(C(CC1CC1)c1ccc([C@H](C)Nc3ncc4c(n3)N(CCC)C(=O)OC4)cc1)C2] | 531 |
| 54 | 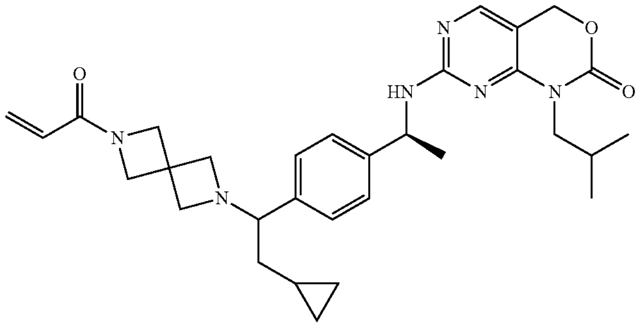 [SMILES: C=CC(=O)N1CC2(C1)CN(C(CC1CC1)c1ccc([C@H](C)Nc3ncc4c(n3)N(CC(C)C)C(=O)OC4)cc1)C2] | 545 |
| 55 | 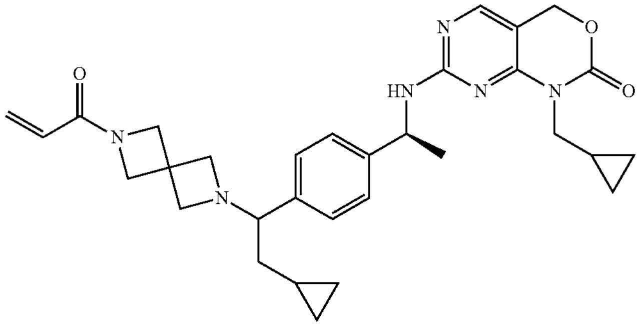 [SMILES: C=CC(=O)N1CC2(C1)CN(C(CC1CC1)c1ccc([C@H](C)Nc3ncc4c(n3)N(CC3CC3)C(=O)OC4)cc1)C2] | 543 |

TABLE 4-continued
| Compound | Structural formula | MS: [M + H]+ |
|---|---|---|
| Compounds 1-84 and 140-159 | | |
| 56 | 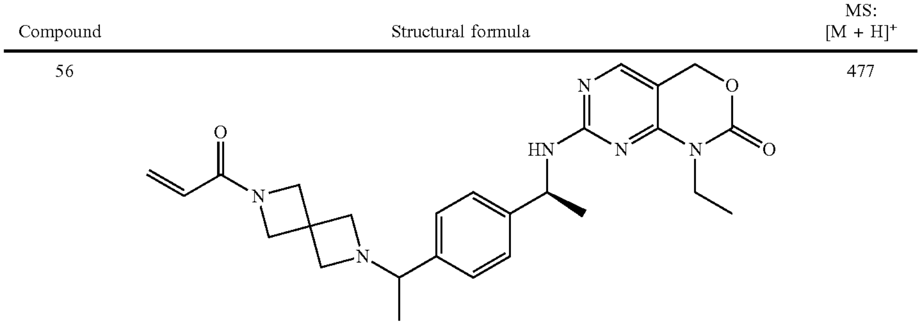 | 477 |
| 57 | 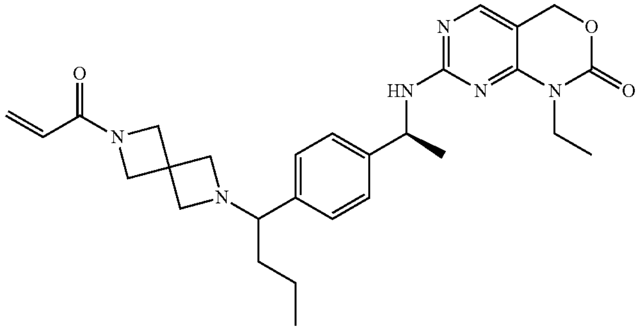 [SMILES: C=CC(=O)N1CC2(C1)CN(C(CCC)c1ccc([C@H](C)Nc3ncc4c(n3)N(CC)C(=O)OC4)cc1)C2] | 505 |
| 58 | 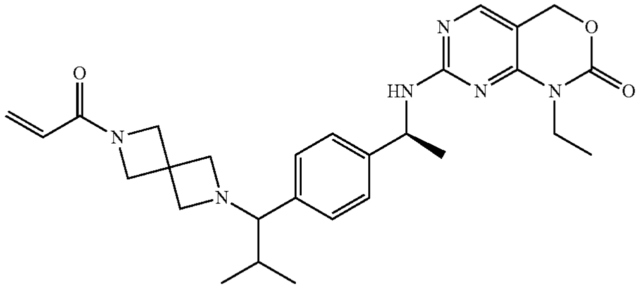 [SMILES: C=CC(=O)N1CC2(C1)CN(C(c1ccc([C@H](C)Nc3ncc4c(n3)N(CC)C(=O)OC4)cc1)C(C)C)C2] | 505 |
| 59 | 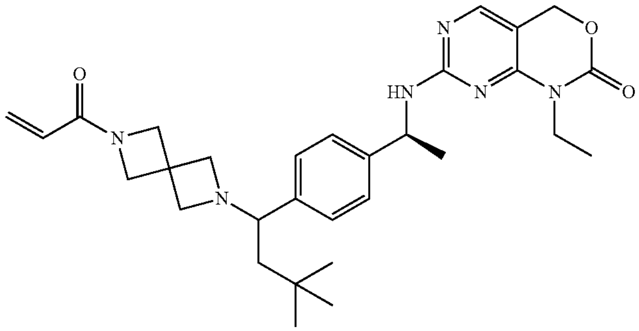 [SMILES: C=CC(=O)N1CC2(C1)CN(C(CC(C)(C)C)c1ccc([C@H](C)Nc3ncc4c(n3)N(CC)C(=O)OC4)cc1)C2] | 533 |
| 60 | 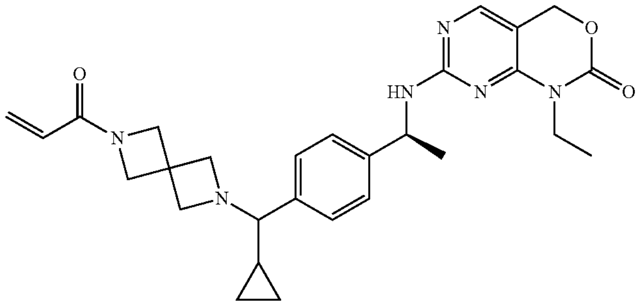 [SMILES: C=CC(=O)N1CC2(C1)CN(C(c1ccc([C@H](C)Nc3ncc4c(n3)N(CC)C(=O)OC4)cc1)C1CC1)C2] | 503 |

TABLE 4-continued
| Compounds 1-84 and 140-159 | | |
|---|---|---|
| Compound | Structural formula | MS: [M + H]+ |
| 61 | 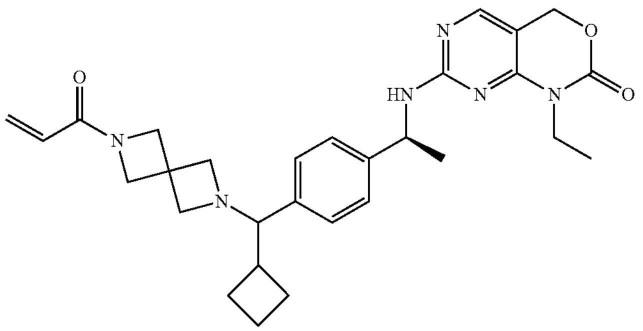 [SMILES: C=CC(=O)N1CC2(C1)CN(C(c1ccc([C@H](C)Nc3ncc4c(n3)N(CC)C(=O)OC4)cc1)C1CCC1)C2] | 517 |
| 62 | 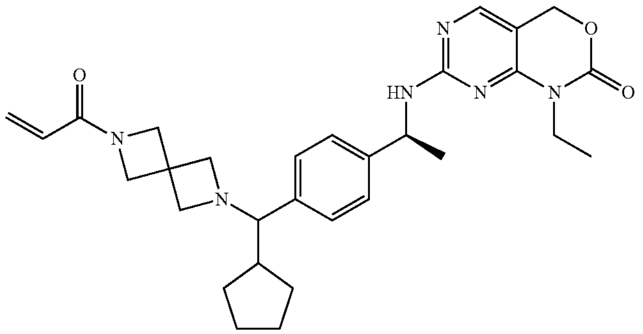 [SMILES: C=CC(=O)N1CC2(C1)CN(C(c1ccc([C@H](C)Nc3ncc4c(n3)N(CC)C(=O)OC4)cc1)C1CCCC1)C2] | 531 |
| 63 | 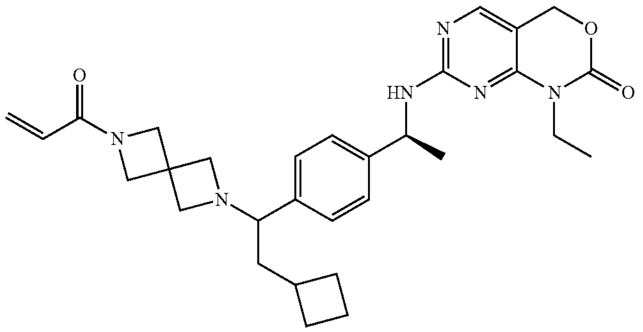 [SMILES: C=CC(=O)N1CC2(C1)CN(C(CC1CCC1)c1ccc([C@H](C)Nc3ncc4c(n3)N(CC)C(=O)OC4)cc1)C2] | 531 |
| 64 | 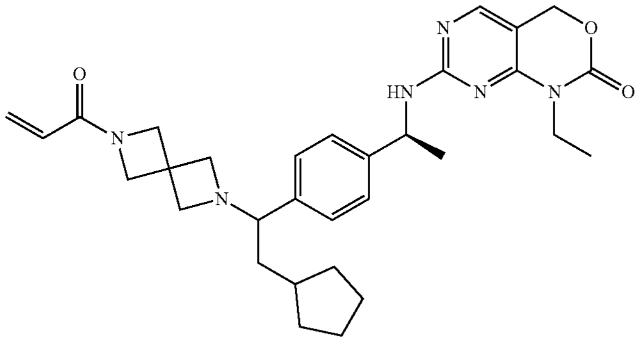 [SMILES: C=CC(=O)N1CC2(C1)CN(C(CC1CCCC1)c1ccc([C@H](C)Nc3ncc4c(n3)N(CC)C(=O)OC4)cc1)C2] | 545 |

TABLE 4-continued
| Compounds 1-84 and 140-159 | | |
|---|---|---|
| Compound | Structural formula | MS: [M + H]+ |
| 65 | 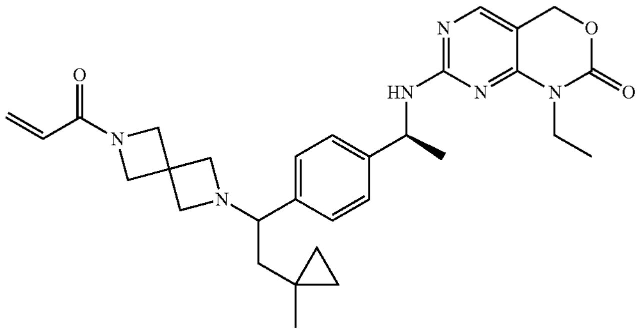 [SMILES: C=CC(=O)N1CC2(C1)CN(C(CC1(C)CC1)c1ccc([C@H](C)Nc3ncc4c(n3)N(CC)C(=O)OC4)cc1)C2] | 531 |
| 66 | 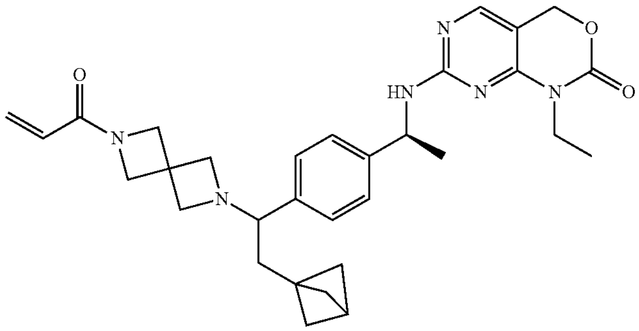 [SMILES: C=CC(=O)N1CC2(C1)CN(C(CC13CC(C1)C3)c1ccc([C@H](C)Nc3ncc4c(n3)N(CC)C(=O)OC4)cc1)C2] | 543 |
| 67 | 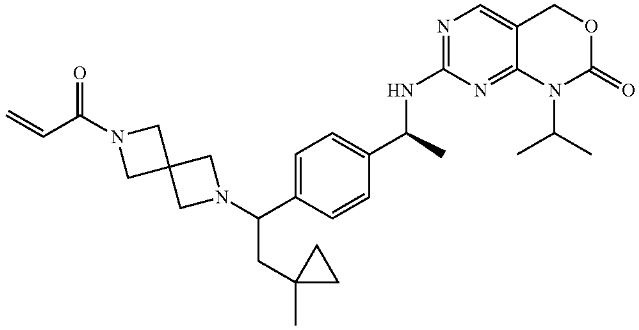 [SMILES: C=CC(=O)N1CC2(C1)CN(C(CC1(C)CC1)c1ccc([C@H](C)Nc3ncc4c(n3)N(C(C)C)C(=O)OC4)cc1)C2] | 545 |
| 68 | 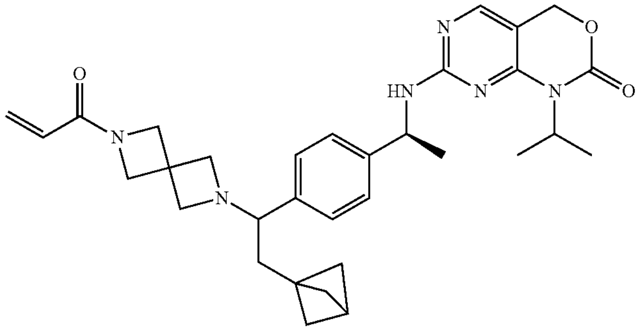 [SMILES: C=CC(=O)N1CC2(C1)CN(C(CC13CC(C1)C3)c1ccc([C@H](C)Nc3ncc4c(n3)N(C(C)C)C(=O)OC4)cc1)C2] | 557 |

TABLE 4-continued
| Compounds 1-84 and 140-159 | | |
|---|---|---|
| Compound | Structural formula | MS: $[M + H]^+$ |
| 69 | 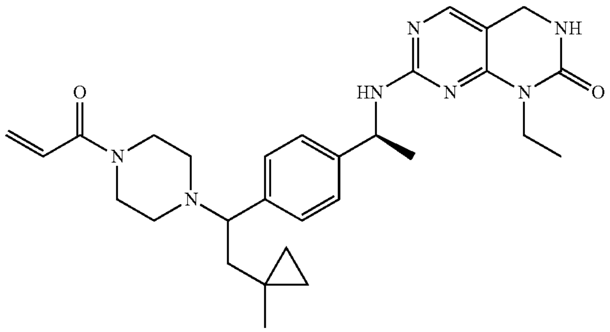 [SMILES: C=CC(=O)N1CCN(C(CC2(C)CC2)c2ccc([C@H](C)Nc3ncc4c(n3)N(CC)C(=O)NC4)cc2)CC1] | 518 |
| 70 | 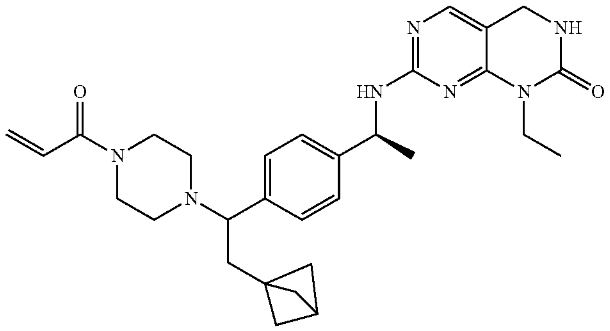 [SMILES: C=CC(=O)N1CCN(C(CC23CC(C2)C3)c2ccc([C@H](C)Nc3ncc4c(n3)N(CC)C(=O)NC4)cc2)CC1] | 530 |
| 71 | 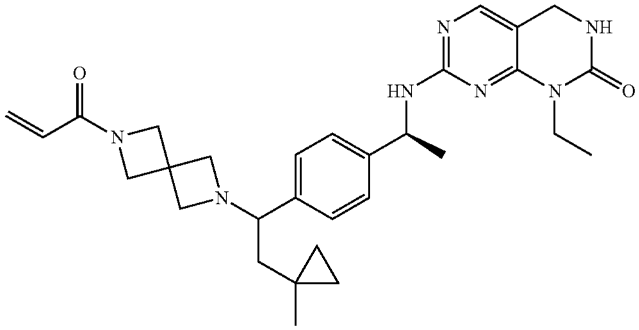 [SMILES: C=CC(=O)N1CC2(C1)CN(C(CC1(C)CC1)c1ccc([C@H](C)Nc3ncc4c(n3)N(CC)C(=O)NC4)cc1)C2] | 530 |
| 72 | 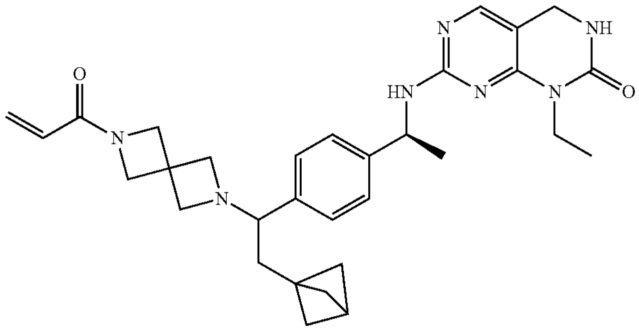 [SMILES: C=CC(=O)N1CC2(C1)CN(C(CC13CC(C1)C3)c1ccc([C@H](C)Nc3ncc4c(n3)N(CC)C(=O)NC4)cc1)C2] | 542 |

TABLE 4-continued
| Compounds 1-84 and 140-159 | | |
| --- | --- | --- |
| Compound | Structural formula | MS: [M + H]+ |
| 73 | 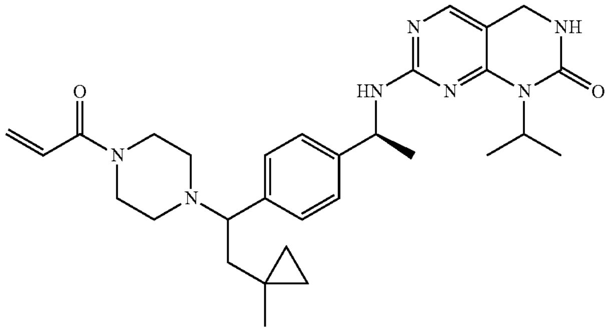 [SMILES: C=CC(=O)N1CCN(C(CC2(C)CC2)c2ccc([C@H](C)Nc3ncc4c(n3)N(C(C)C)C(=O)NC4)cc2)CC1] | 532 |
| 74 | 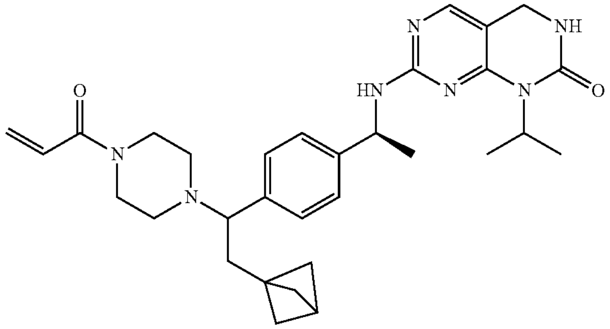 [SMILES: C=CC(=O)N1CCN(C(CC23CC(C2)C3)c2ccc([C@H](C)Nc3ncc4c(n3)N(C(C)C)C(=O)NC4)cc2)CC1] | 544 |
| 75 | 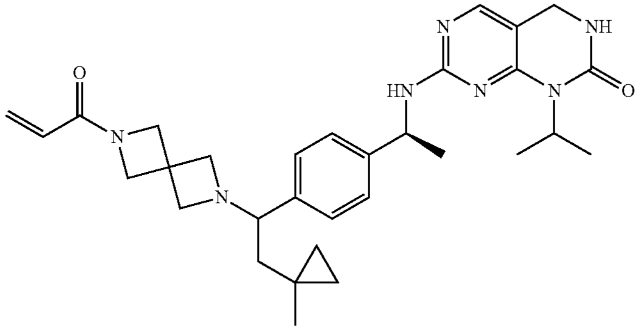 [SMILES: C=CC(=O)N1CC2(C1)CN(C(CC1(C)CC1)c1ccc([C@H](C)Nc3ncc4c(n3)N(C(C)C)C(=O)NC4)cc1)C2] | 544 |
| 76 | 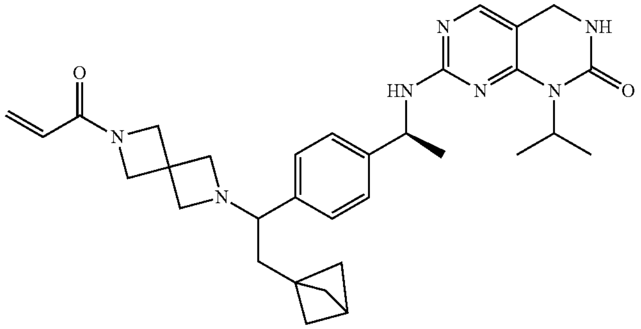 [SMILES: C=CC(=O)N1CC2(C1)CN(C(CC13CC(C1)C3)c1ccc([C@H](C)Nc3ncc4c(n3)N(C(C)C)C(=O)NC4)cc1)C2] | 556 |

TABLE 4-continued
| Compounds 1-84 and 140-159 | | |
|---|---|---|
| Compound | Structural formula | MS: [M + H]+ |
| 77 | 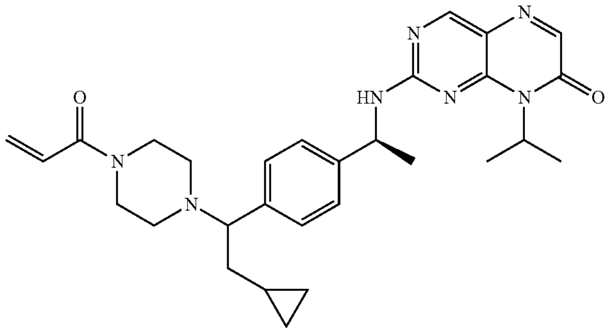 [SMILES: C=CC(=O)N1CCN(C(CC2CC2)c2ccc([C@H](C)Nc3ncc4ncc(=O)n(C(C)C)c4n3)cc2)CC1] | 516 |
| 78 | 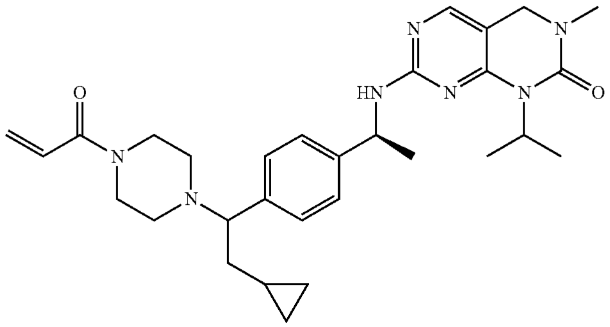 [SMILES: C=CC(=O)N1CCN(C(CC2CC2)c2ccc([C@H](C)Nc3ncc4c(n3)N(C(C)C)C(=O)N(C)C4)cc2)CC1] | 532 |
| 79 | 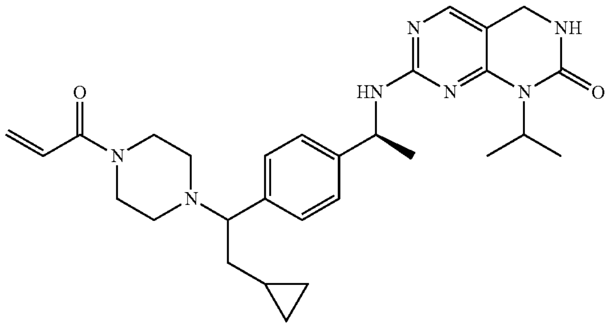 [SMILES: C=CC(=O)N1CCN(C(CC2CC2)c2ccc([C@H](C)Nc3ncc4c(n3)N(C(C)C)C(=O)NC4)cc2)CC1] | 518 |
| 80 | 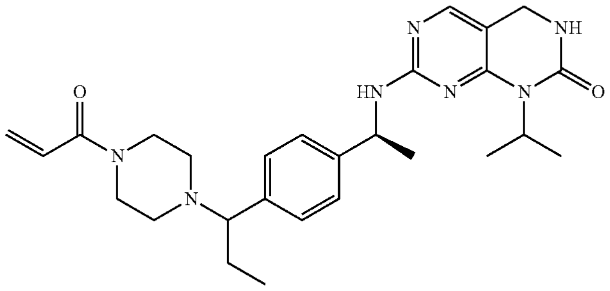 [SMILES: C=CC(=O)N1CCN(C(CC)c2ccc([C@H](C)Nc3ncc4c(n3)N(C(C)C)C(=O)NC4)cc2)CC1] | 492 |

TABLE 4-continued
| Compounds 1-84 and 140-159 | | |
|---|---|---|
| Compound | Structural formula | MS: [M + H]+ |
| 81 | 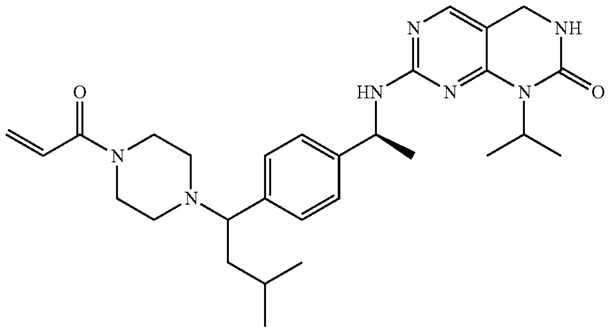 [SMILES: C=CC(=O)N1CCN(C(CC(C)C)c2ccc([C@H](C)Nc3ncc4c(n3)N(C(C)C)C(=O)NC4)cc2)CC1] | 520 |
| 82 | 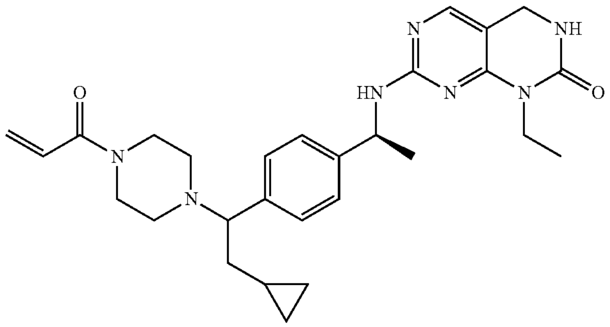 [SMILES: C=CC(=O)N1CCN(C(CC2CC2)c2ccc([C@H](C)Nc3ncc4c(n3)N(CC)C(=O)NC4)cc2)CC1] | 504 |
| 83 | 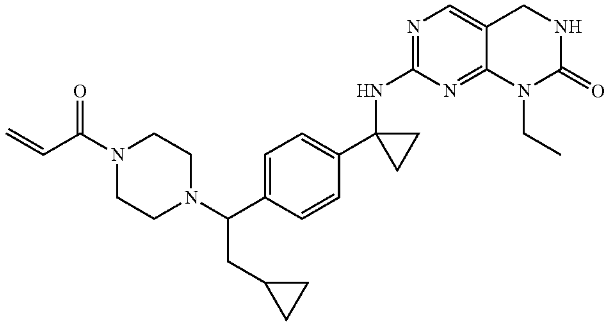 [SMILES: C=CC(=O)N1CCN(C(CC2CC2)c2ccc(C3(Nc4ncc5c(n4)N(CC)C(=O)NC5)CC3)cc2)CC1] | 516 |
| 84 | 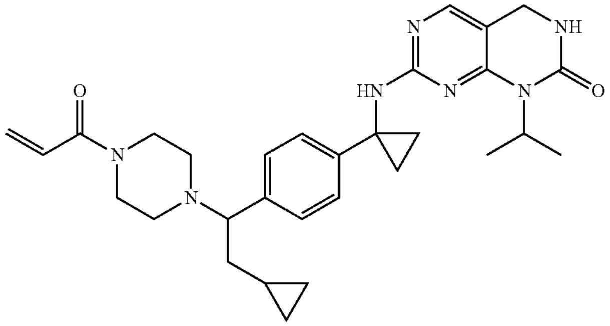 [SMILES: C=CC(=O)N1CCN(C(CC2CC2)c2ccc(C3(Nc4ncc5c(n4)N(C(C)C)C(=O)NC5)CC3)cc2)CC1] | 530 |

TABLE 4-continued
| Compounds 1-84 and 140-159 | | |
|---|---|---|
| Compound | Structural formula | MS: [M + H]+ |
| 140 | 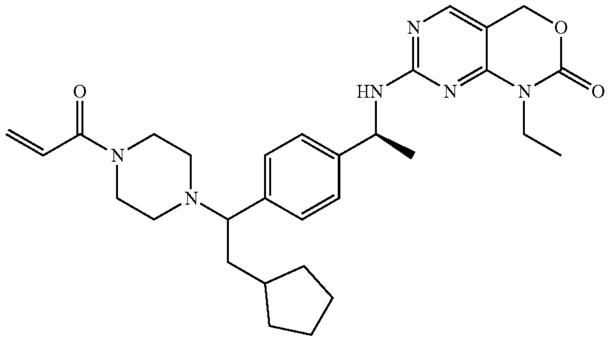 [SMILES: C=CC(=O)N1CCN(C(CC2CCCC2)c2ccc([C@H](C)Nc3ncc4c(n3)N(CC)C(=O)OC4)cc2)CC1] | 533 |
| 141 | 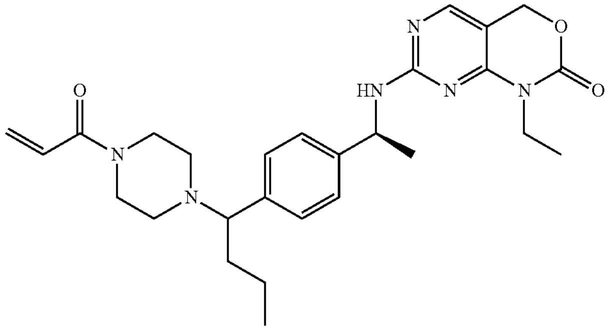 [SMILES: C=CC(=O)N1CCN(C(CCC)c2ccc([C@H](C)Nc3ncc4c(n3)N(CC)C(=O)OC4)cc2)CC1] | 493 |
| 142 | 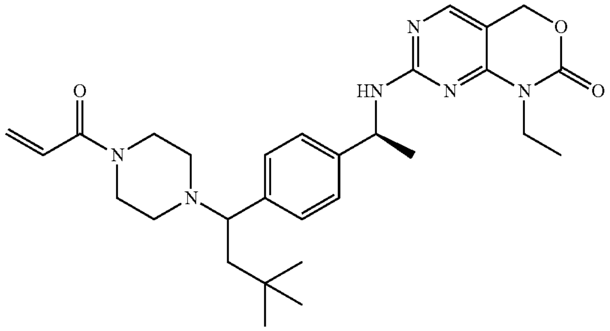 [SMILES: C=CC(=O)N1CCN(C(CC(C)(C)C)c2ccc([C@H](C)Nc3ncc4c(n3)N(CC)C(=O)OC4)cc2)CC1] | 521 |
| 143 | 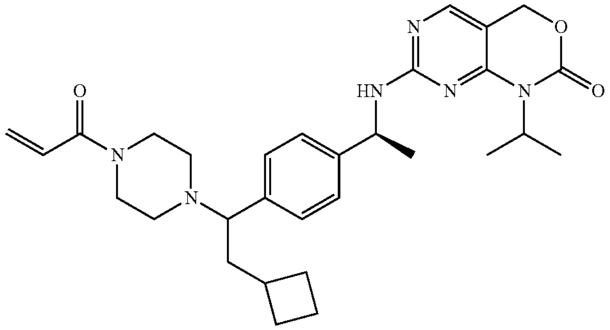 [SMILES: C=CC(=O)N1CCN(C(CC2CCC2)c2ccc([C@H](C)Nc3ncc4c(n3)N(C(C)C)C(=O)OC4)cc2)CC1] | 533 |

TABLE 4-continued
| Compounds 1-84 and 140-159 | | |
|---|---|---|
| Compound | Structural formula | MS: [M + H]+ |
| 144 | 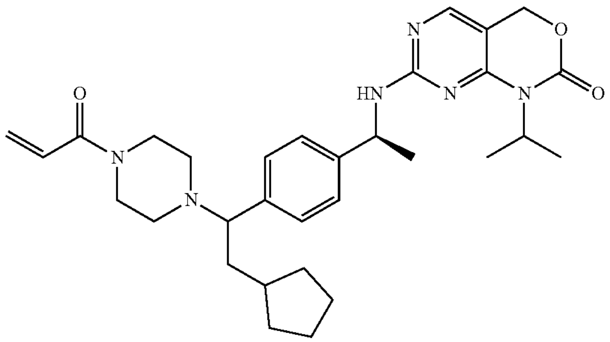 [SMILES: C=CC(=O)N1CCN(C(CC2CCCC2)c2ccc([C@H](C)Nc3ncc4c(n3)N(C(C)C)C(=O)OC4)cc2)CC1] | 547 |
| 145 | 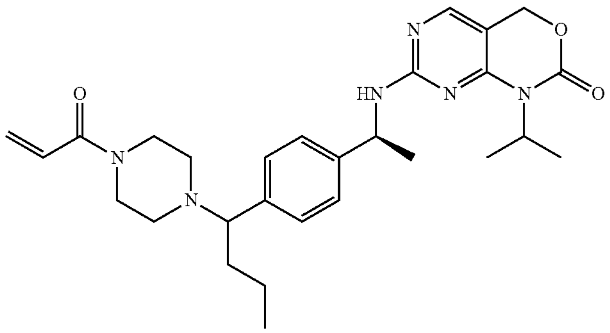 [SMILES: C=CC(=O)N1CCN(C(CCC)c2ccc([C@H](C)Nc3ncc4c(n3)N(C(C)C)C(=O)OC4)cc2)CC1] | 507 |
| 146 | 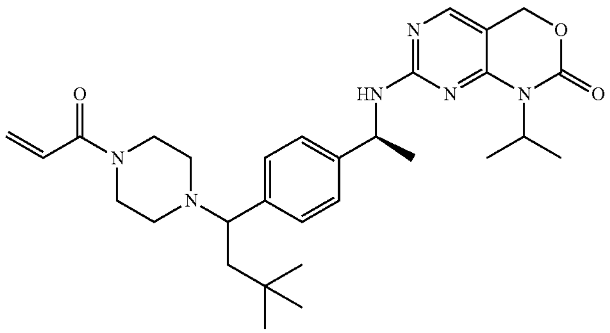 [SMILES: C=CC(=O)N1CCN(C(CC(C)(C)C)c2ccc([C@H](C)Nc3ncc4c(n3)N(C(C)C)C(=O)OC4)cc2)CC1] | 535 |
| 147 | 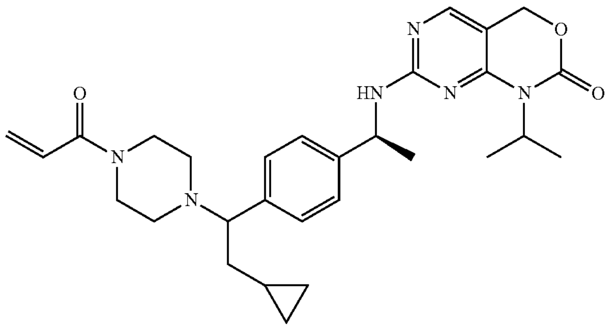 [SMILES: C=CC(=O)N1CCN(C(CC2CC2)c2ccc([C@H](C)Nc3ncc4c(n3)N(C(C)C)C(=O)OC4)cc2)CC1] | 519 |

TABLE 4-continued
| Compounds 1-84 and 140-159 | | |
|---|---|---|
| Compound | Structural formula | MS: [M + H]+ |
| 148 | 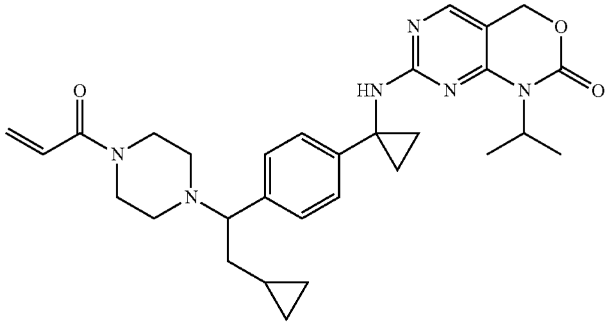 [SMILES: C=CC(=O)N1CCN(C(CC2CC2)c2ccc(C3(Nc4ncc5c(n4)N(C(C)C)C(=O)OC5)CC3)cc2)CC1] | 531 |
| 149 | 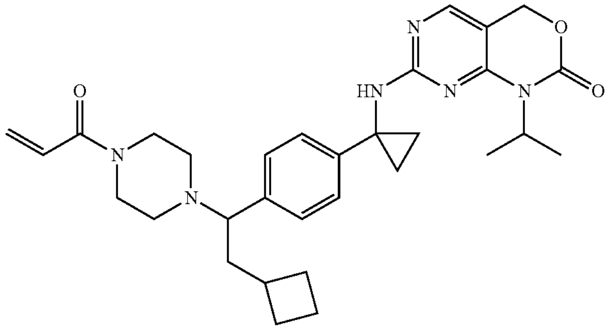 [SMILES: C=CC(=O)N1CCN(C(CC2CCC2)c2ccc(C3(Nc4ncc5c(n4)N(C(C)C)C(=O)OC5)CC3)cc2)CC1] | 545 |
| 150 | 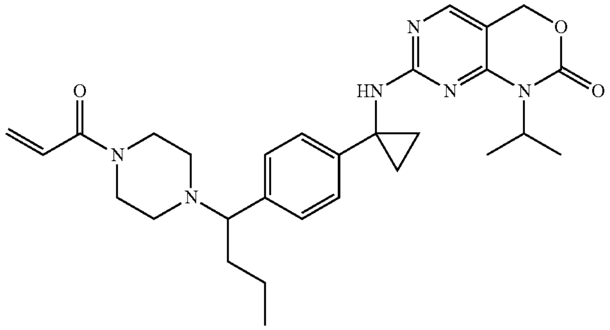 [SMILES: C=CC(=O)N1CCN(C(CCC)c2ccc(C3(Nc4ncc5c(n4)N(C(C)C)C(=O)OC5)CC3)cc2)CC1] | 519 |
| 151 | 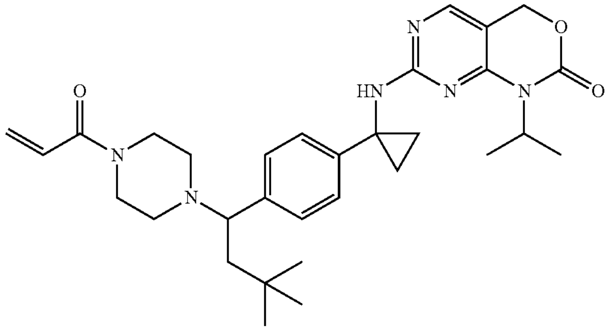 [SMILES: C=CC(=O)N1CCN(C(CC(C)(C)C)c2ccc(C3(Nc4ncc5c(n4)N(C(C)C)C(=O)OC5)CC3)cc2)CC1] | 547 |

TABLE 4-continued
| Compound | Structural formula | MS: [M + H]+ |
|---|---|---|
| | Compounds 1-84 and 140-159 | |
| 152 | 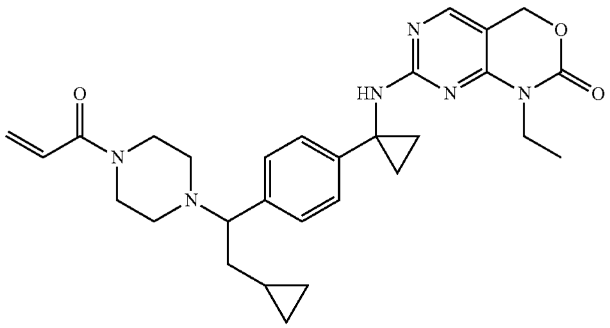 [SMILES: C=CC(=O)N1CCN(C(CC2CC2)c2ccc(C3(Nc4ncc5c(n4)N(CC)C(=O)OC5)CC3)cc2)CC1] | 517 |
| 153 | 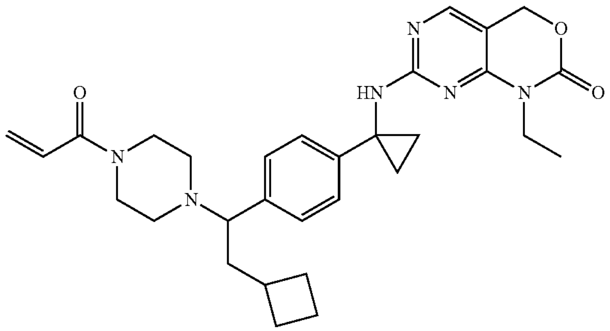 [SMILES: C=CC(=O)N1CCN(C(CC2CCC2)c2ccc(C3(Nc4ncc5c(n4)N(CC)C(=O)OC5)CC3)cc2)CC1] | 531 |
| 154 | 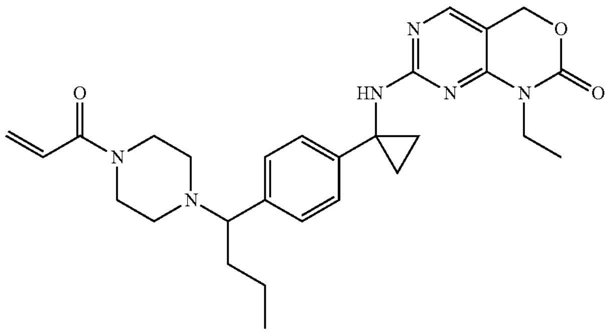 [SMILES: C=CC(=O)N1CCN(C(CCC)c2ccc(C3(Nc4ncc5c(n4)N(CC)C(=O)OC5)CC3)cc2)CC1] | 505 |
| 155 | 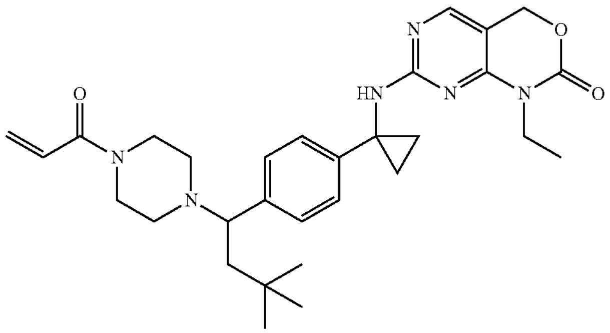 [SMILES: C=CC(=O)N1CCN(C(CC(C)(C)C)c2ccc(C3(Nc4ncc5c(n4)N(CC)C(=O)OC5)CC3)cc2)CC1] | 533 |

TABLE 4-continued
| Compounds 1-84 and 140-159 | | |
|---|---|---|
| Compound | Structural formula | MS: [M + H]+ |
| 156 | 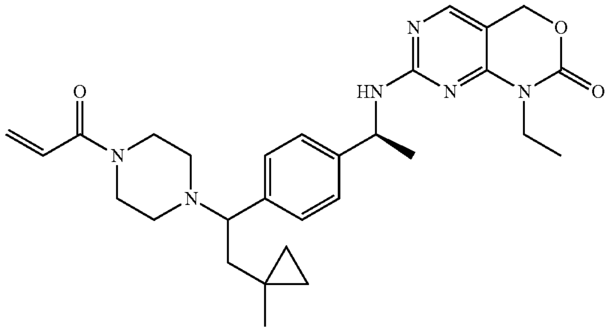 | 519 |
| 157 | 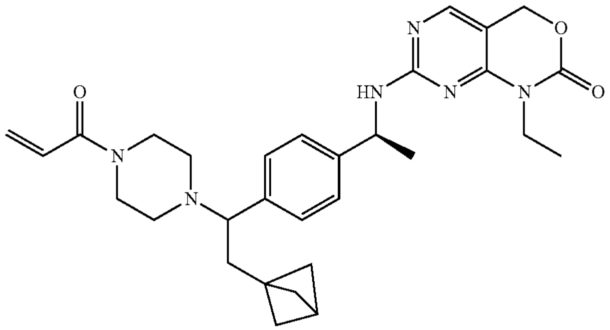 | 531 |
| 158 | 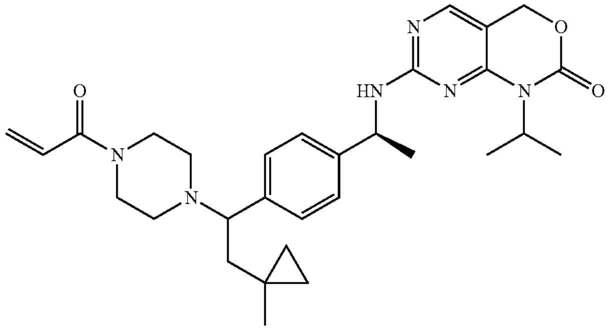 | 533 |
| 159 | 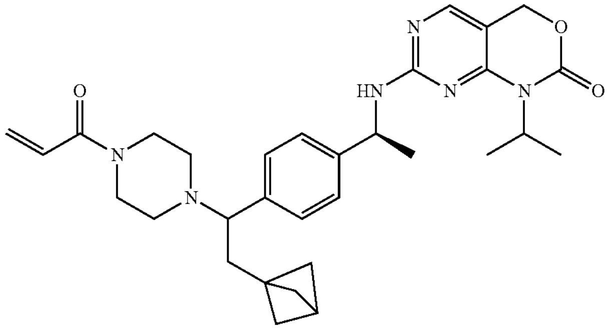 | 545 |

Example 106. Synthesis of 7-(((1S)-1-(4-(1-(4-acryloylpiperazin-1-yl)-2-cyclopropylethyl)phenyl)ethyl)amino)-1-isopropylpyrimidine[4,5-d]pyrimidine-2(1H)-one (Compound 85)

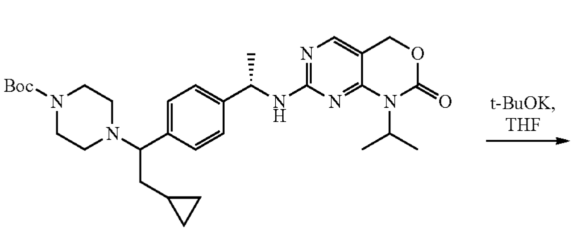

85-0

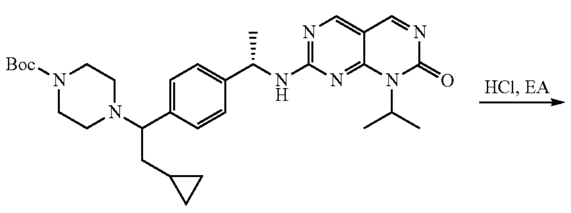

85-1

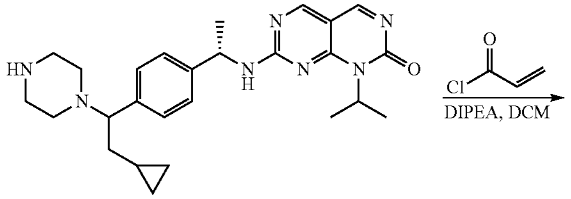

85-1

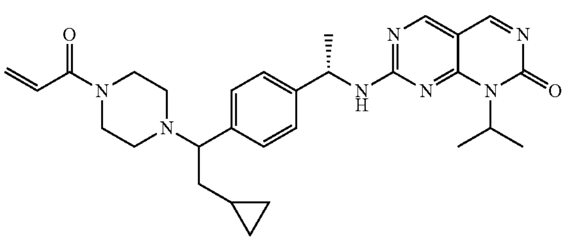

85

Step 1: Synthesis of Compound 85-1

Compound 85-0 (100 mg, 0.182 mmol, by the procedures similar to those in the synthesis of compound 119-2) was dissolved in THF (5 mL), t-BuOK (100 mg, 0.88 mmol) was added in argon atmosphere, and the mixed solution was stirred at room temperature for 20 h. The remaining starting materials was detected by LC-MS, and the system was quenched with saturated ammonium chloride solution (10 mL), and then extracted with EA (20 mL×2). The organic phases were combined, washed with saturated sodium chloride solution (10 mL), dried over anhydrous $Na_2SO_4$, filtered, and concentrated to give a crude compound 85-1 (180 mg, 100% yield). ESI-MS m/z: 562 $[M+H]^+$.

Step 2: Synthesis of Compound 85-2

Compound 85-1 (180 mg, 0.182 mmol) was dissolved in DCM (10 mL), TFA (3 mL) was added, and the mixed solution was stirred at room temperature for about 1 h. After the completion of the reaction as detected by LC-MS, the mixed solution was concentrated at reduced pressure to give a crude compound 85-2 as a brown solid (100 mg, 100% yield). ESI-MS m/z: 462 $[M+H]^+$.

Step 3: Synthesis of Compound 85

Compound 85-2 (100 mg, 0.182 mmol) was dissolved in DCM (10 mL), DIPEA (103 mg, 0.80 mmol) was added, acryloyl chloride (21 mg, 0.24 mmol) was then added dropwise, and the mixed solution was incubated at room temperature for about 10 min for reaction. After the completion of the reaction as detected by LC-MS, water (10 mL) was added. The mixed solution was extracted with DCM (10 mL×2), the organic phases were combined and concentrated to dryness by rotary evaporation, and the residue was purified by prep-HPLC to give a product 85 as a light yellow solid (22 mg, 23% yield).

$^1H$ NMR (400 MHz, $CDCl_3$) δ: 7.77 (s, 1H), 7.28 (d, J=7.9 Hz, 2H), 7.17 (d, J=7.8 Hz, 2H), 6.46 (dd, J=16.8, 10.5 Hz, 1H), 6.21 (dd, J=16.9, 1.9 Hz, 1H), 5.62 (dd, J=10.5, 1.9 Hz, 1H), 5.01 (s, 1H), 4.17 (s, 1H), 3.63 (s, 2H), 3.49 (s, 2H), 3.40 (s, 1H), 2.37 (s, 4H), 1.86 (d, J=11.8 Hz, 2H), 1.53 (d, J=6.9 Hz, 3H), 1.36 (t, J=6.2 Hz, 3H), 1.24 (s, 3H), 0.43-0.32 (m, 1H), 0.29 (s, 2H), −0.07 (d, J=15.0 Hz, 2H); ESI-MS m/z: 516 $[M+H]^+$.

Examples 107-159. Synthesis of Compounds 86-138

By the procedures similar to those in the synthesis of compound 85, the target compounds 86-138 in Table 5 may be obtained with different intermediates as starting materials.

TABLE 5
| Compounds 86-138 | | |
|---|---|---|
| Compound | Structural formula | MS: [M + H]+ |
| 86 | 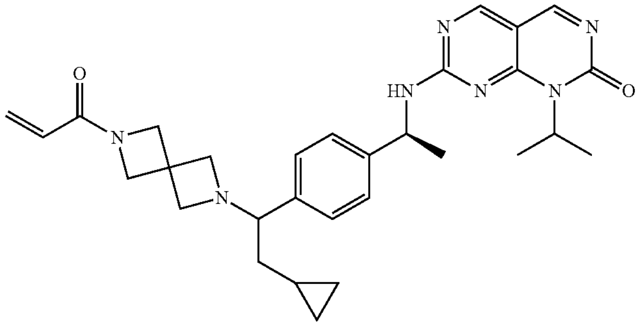 [SMILES: C=CC(=O)N1CC2(C1)CN(C(CC1CC1)c1ccc([C@H](C)Nc3ncc4cnc(=O)n(C(C)C)c4n3)cc1)C2] | 528 |
| 87 | 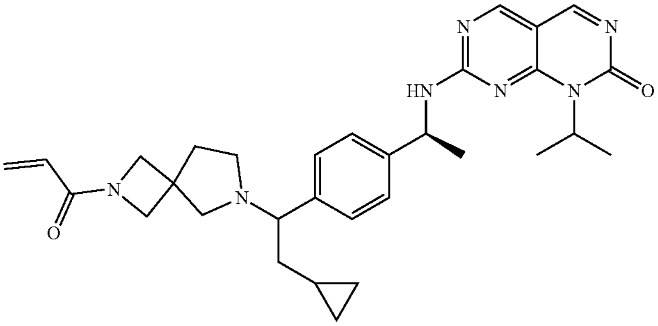 [SMILES: C=CC(=O)N1CC2(CCN(C(CC3CC3)c3ccc([C@H](C)Nc4ncc5cnc(=O)n(C(C)C)c5n4)cc3)C2)C1] | 542 |
| 88 | 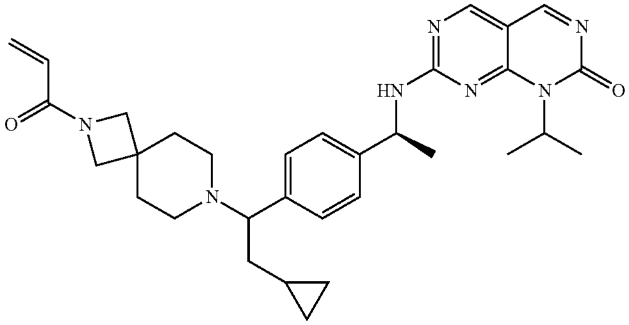 [SMILES: C=CC(=O)N1CC2(CCN(C(CC3CC3)c3ccc([C@H](C)Nc4ncc5cnc(=O)n(C(C)C)c5n4)cc3)CC2)C1] | 556 |
| 89 | 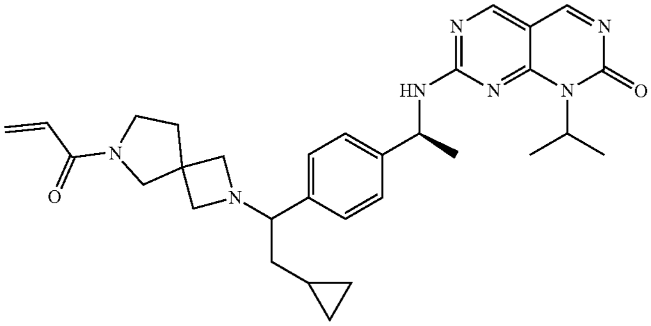 [SMILES: C=CC(=O)N1CCC2(C1)CN(C(CC1CC1)c1ccc([C@H](C)Nc3ncc4cnc(=O)n(C(C)C)c4n3)cc1)C2] | 542 |

TABLE 5-continued
| Compounds 86-138 | | |
|---|---|---|
| Compound | Structural formula | MS: [M + H]+ |
| 90 | 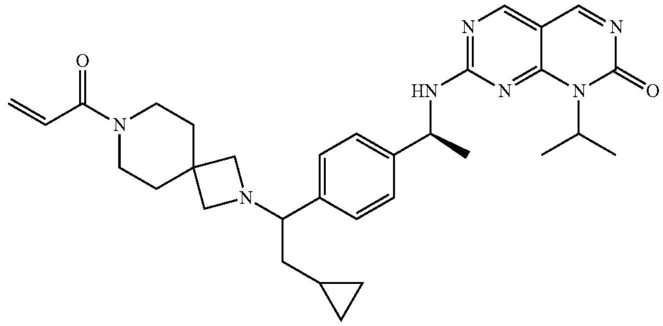 [SMILES: C=CC(=O)N1CCC2(CC1)CN(C(CC1CC1)c1ccc([C@H](C)Nc3ncc4cnc(=O)n(C(C)C)c4n3)cc1)C2] | 556 |
| 91 | 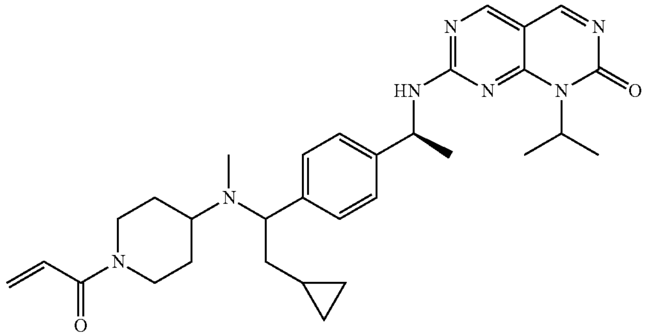 [SMILES: C=CC(=O)N1CCC(N(C)C(CC2CC2)c2ccc([C@H](C)Nc3ncc4cnc(=O)n(C(C)C)c4n3)cc2)CC1] | 544 |
| 92 | 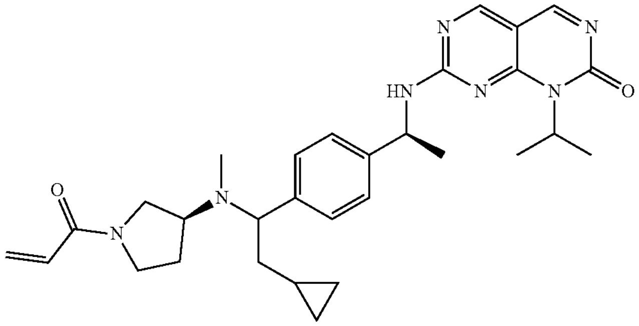 [SMILES: C=CC(=O)N1CC[C@H](N(C)C(CC2CC2)c2ccc([C@H](C)Nc3ncc4cnc(=O)n(C(C)C)c4n3)cc2)C1] | 530 |
| 93 | 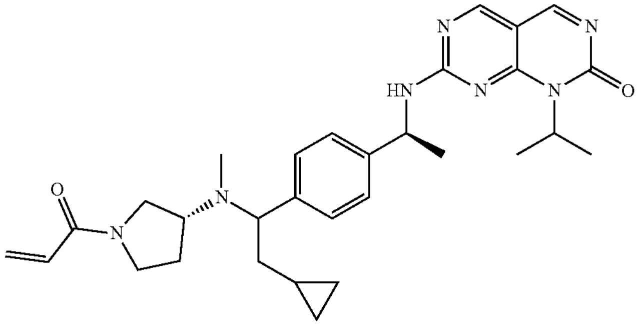 [SMILES: C=CC(=O)N1CC[C@@H](N(C)C(CC2CC2)c2ccc([C@H](C)Nc3ncc4cnc(=O)n(C(C)C)c4n3)cc2)C1] | 530 |

TABLE 5-continued
| Compounds 86-138 | | |
|---|---|---|
| Compound | Structural formula | MS: [M + H]+ |
| 94 | 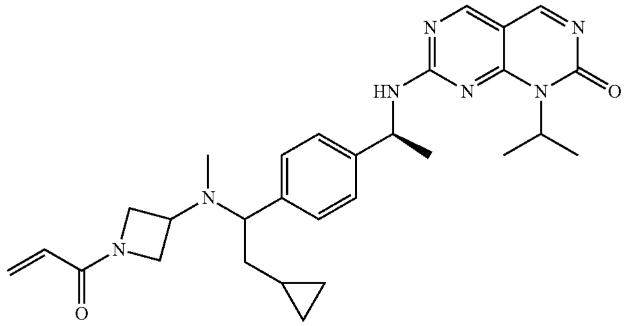 [SMILES: C=CC(=O)N1CC(N(C)C(CC2CC2)c2ccc([C@H](C)Nc3ncc4cnc(=O)n(C(C)C)c4n3)cc2)C1] | 516 |
| 95 | 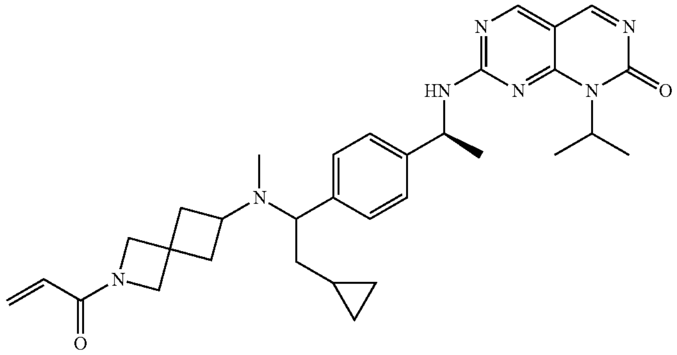 [SMILES: C=CC(=O)N1CC2(CC(N(C)C(CC3CC3)c3ccc([C@H](C)Nc4ncc5cnc(=O)n(C(C)C)c5n4)cc3)C2)C1] | 556 |
| 96 | 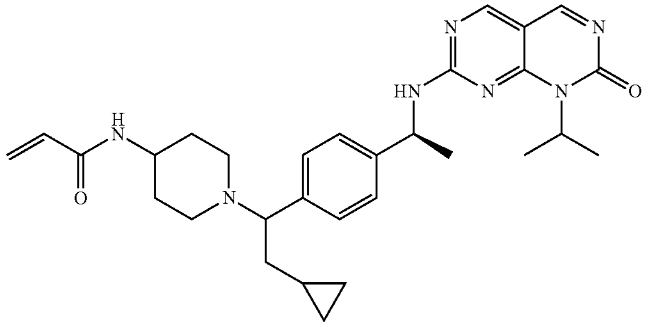 [SMILES: C=CC(=O)NC1CCN(C(CC2CC2)c2ccc([C@H](C)Nc3ncc4cnc(=O)n(C(C)C)c4n3)cc2)CC1] | 530 |
| 97 | 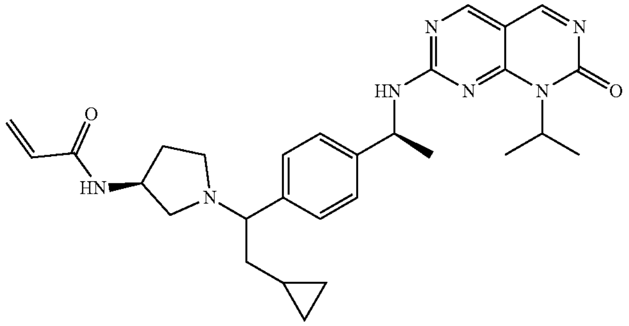 [SMILES: C=CC(=O)N[C@H]1CCN(C(CC2CC2)c2ccc([C@H](C)Nc3ncc4cnc(=O)n(C(C)C)c4n3)cc2)C1] | 516 |

TABLE 5-continued
| Compounds 86-138 | | |
|---|---|---|
| Compound | Structural formula | MS: [M + H]+ |
| 98 | 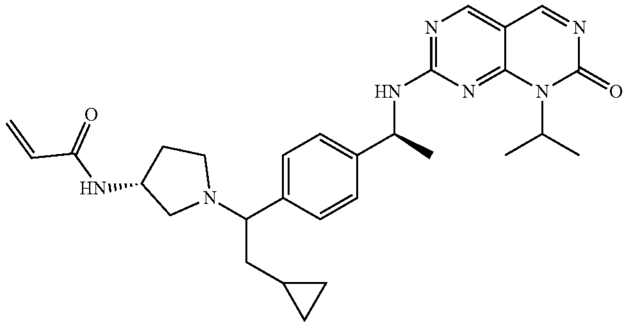 [SMILES: C=CC(=O)N[C@@H]1CCN(C(CC2CC2)c2ccc([C@H](C)Nc3ncc4cnc(=O)n(C(C)C)c4n3)cc2)C1] | 516 |
| 99 | 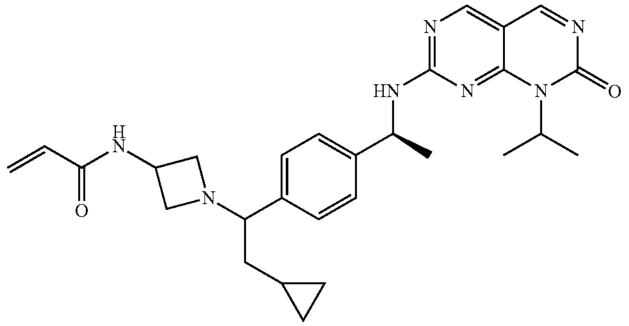 [SMILES: C=CC(=O)NC1CN(C(CC2CC2)c2ccc([C@H](C)Nc3ncc4cnc(=O)n(C(C)C)c4n3)cc2)C1] | 502 |
| 100 | 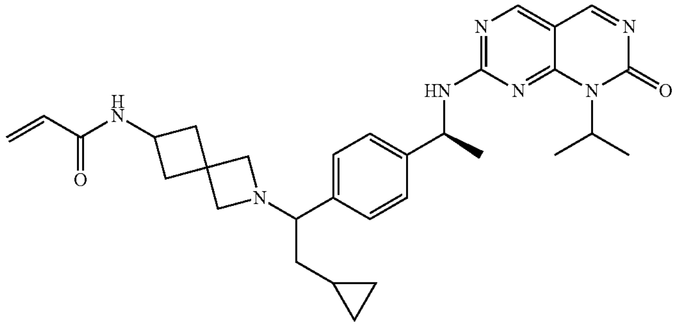 [SMILES: C=CC(=O)NC1CC2(C1)CN(C(CC1CC1)c1ccc([C@H](C)Nc3ncc4cnc(=O)n(C(C)C)c4n3)cc1)C2] | 542 |
| 101 | 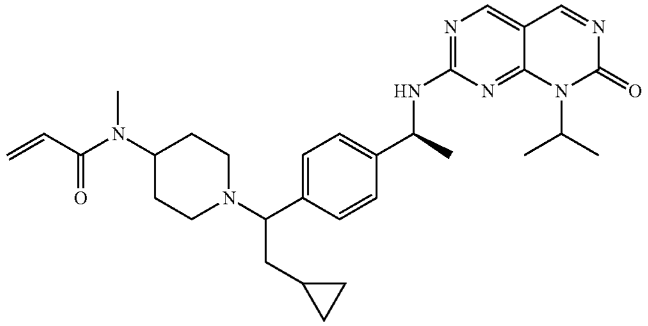 [SMILES: C=CC(=O)N(C)C1CCN(C(CC2CC2)c2ccc([C@H](C)Nc3ncc4cnc(=O)n(C(C)C)c4n3)cc2)CC1] | 544 |

TABLE 5-continued
| Compounds 86-138 | | |
|---|---|---|
| Compound | Structural formula | MS: $[M + H]^+$ |
| 102 | 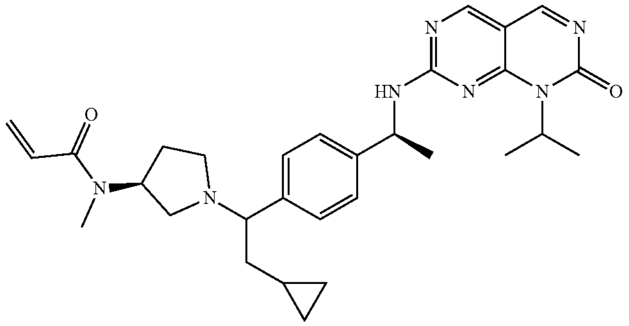 [SMILES: C=CC(=O)N(C)[C@H]1CCN(C(CC2CC2)c2ccc([C@H](C)Nc3ncc4cnc(=O)n(C(C)C)c4n3)cc2)C1] | 530 |
| 103 | 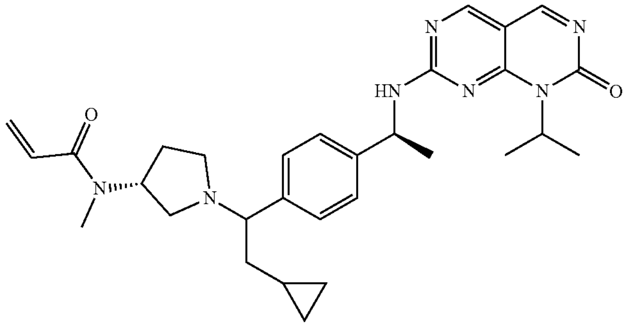 [SMILES: C=CC(=O)N(C)[C@@H]1CCN(C(CC2CC2)c2ccc([C@H](C)Nc3ncc4cnc(=O)n(C(C)C)c4n3)cc2)C1] | 530 |
| 104 | 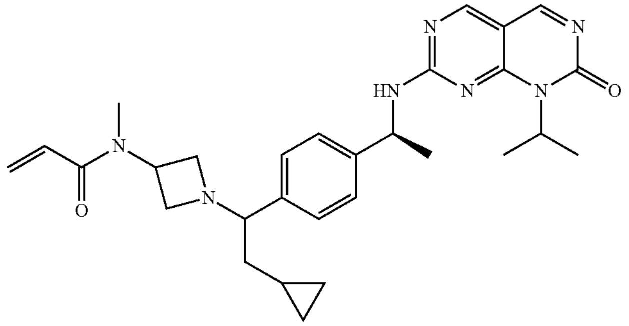 [SMILES: C=CC(=O)N(C)C1CN(C(CC2CC2)c2ccc([C@H](C)Nc3ncc4cnc(=O)n(C(C)C)c4n3)cc2)C1] | 516 |
| 105 | 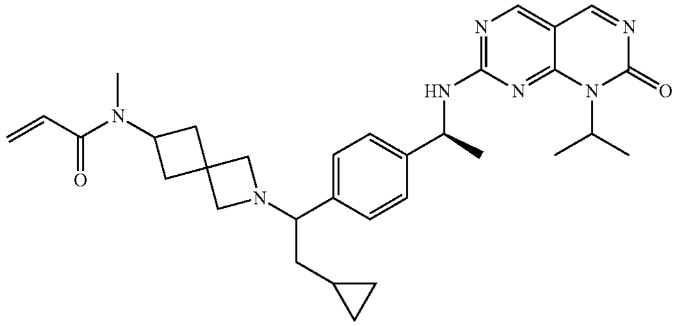 [SMILES: C=CC(=O)N(C)C1CC2(C1)CN(C(CC1CC1)c1ccc([C@H](C)Nc3ncc4cnc(=O)n(C(C)C)c4n3)cc1)C2] | 556 |

TABLE 5-continued
| Compounds 86-138 | | |
|---|---|---|
| Compound | Structural formula | MS: [M + H]$^+$ |
| 106 | 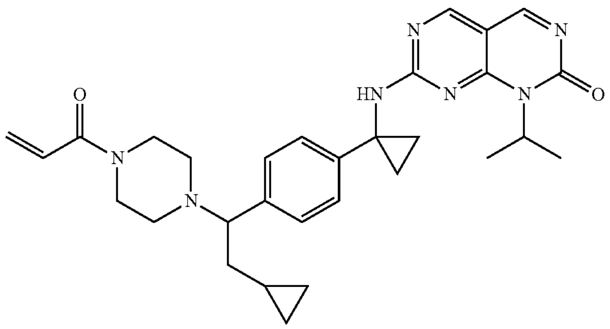 [SMILES: C=CC(=O)N1CCN(C(CC2CC2)c2ccc(C3(Nc4ncc5cnc(=O)n(C(C)C)c5n4)CC3)cc2)CC1] | 528 |
| 107 | 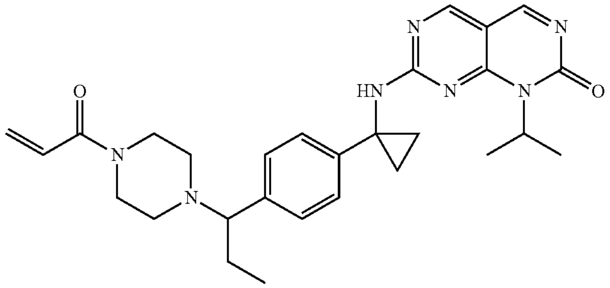 [SMILES: C=CC(=O)N1CCN(C(CC)c2ccc(C3(Nc4ncc5cnc(=O)n(C(C)C)c5n4)CC3)cc2)CC1] | 502 |
| 108 | 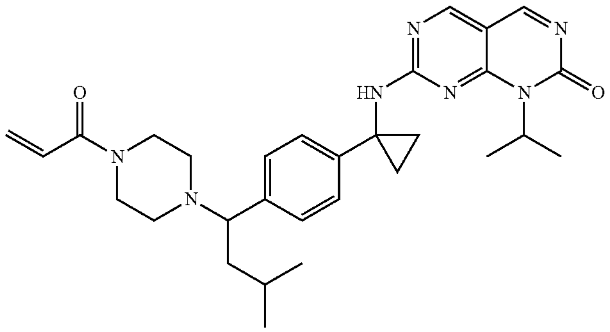 [SMILES: C=CC(=O)N1CCN(C(CC(C)C)c2ccc(C3(Nc4ncc5cnc(=O)n(C(C)C)c5n4)CC3)cc2)CC1] | 530 |
| 109 | 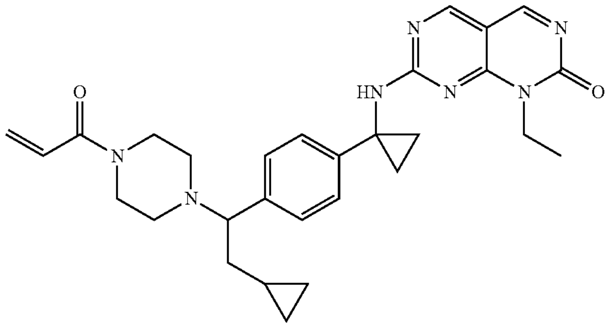 [SMILES: C=CC(=O)N1CCN(C(CC2CC2)c2ccc(C3(Nc4ncc5cnc(=O)n(CC)c5n4)CC3)cc2)CC1] | 514 |

TABLE 5-continued
| Compound | Structural formula | MS: [M + H]+ |
| --- | --- | --- |
| Compounds 86-138 | | |
| 110 | 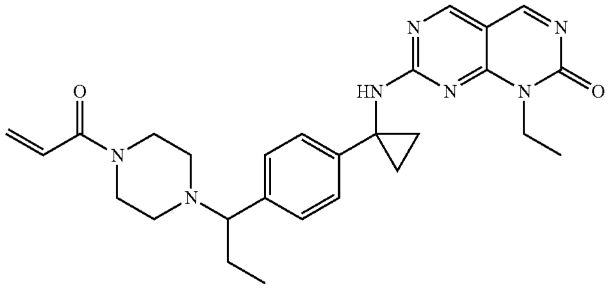 [SMILES: C=CC(=O)N1CCN(C(CC)c2ccc(C3(Nc4ncc5cnc(=O)n(CC)c5n4)CC3)cc2)CC1] | 488 |
| 111 | 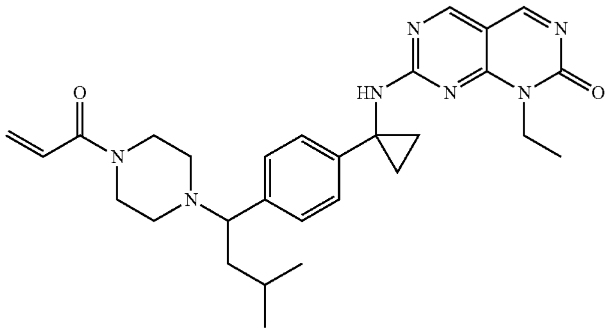 [SMILES: C=CC(=O)N1CCN(C(CC(C)C)c2ccc(C3(Nc4ncc5cnc(=O)n(CC)c5n4)CC3)cc2)CC1] | 516 |
| 112 | 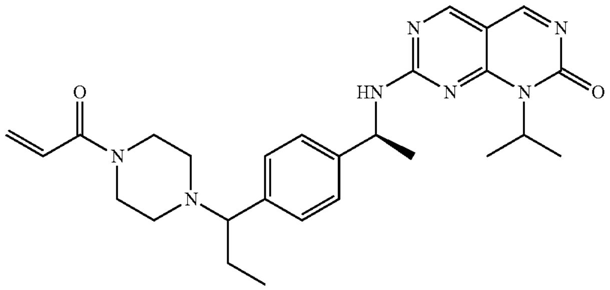 [SMILES: C=CC(=O)N1CCN(C(CC)c2ccc([C@H](C)Nc3ncc4cnc(=O)n(C(C)C)c4n3)cc2)CC1] | 490 |
| 113 | 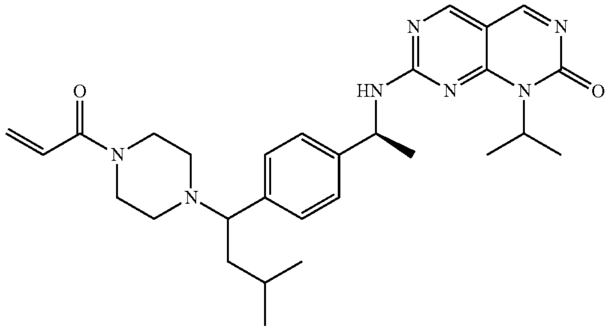 [SMILES: C=CC(=O)N1CCN(C(CC(C)C)c2ccc([C@H](C)Nc3ncc4cnc(=O)n(C(C)C)c4n3)cc2)CC1] | 518 |

TABLE 5-continued
| Compound | Structural formula | MS: [M + H]+ |
| --- | --- | --- |
| | Compounds 86-138 | |
| 114 | 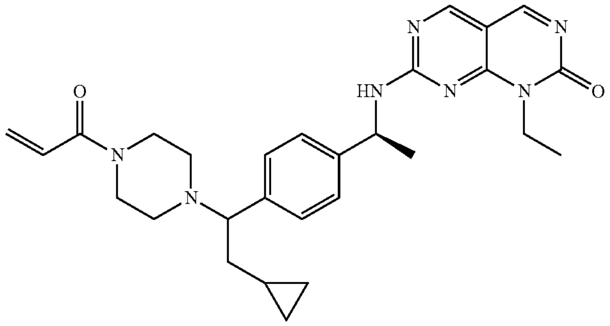 [SMILES: C=CC(=O)N1CCN(C(CC2CC2)c2ccc([C@H](C)Nc3ncc4cnc(=O)n(CC)c4n3)cc2)CC1] | 502 |
| 115 | 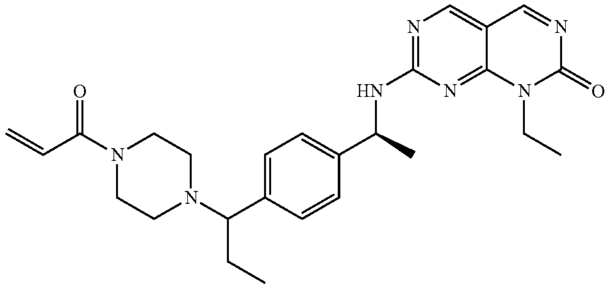 [SMILES: C=CC(=O)N1CCN(C(CC)c2ccc([C@H](C)Nc3ncc4cnc(=O)n(CC)c4n3)cc2)CC1] | 476 |
| 116 | 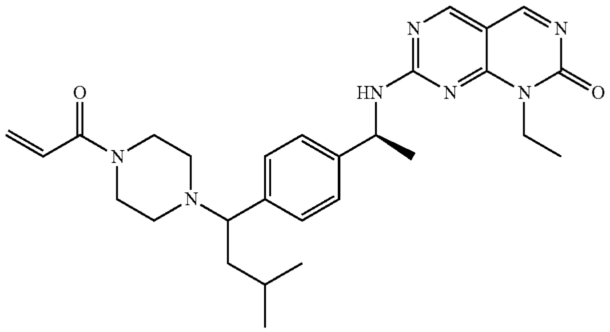 [SMILES: C=CC(=O)N1CCN(C(CC(C)C)c2ccc([C@H](C)Nc3ncc4cnc(=O)n(CC)c4n3)cc2)CC1] | 504 |
| 117 | 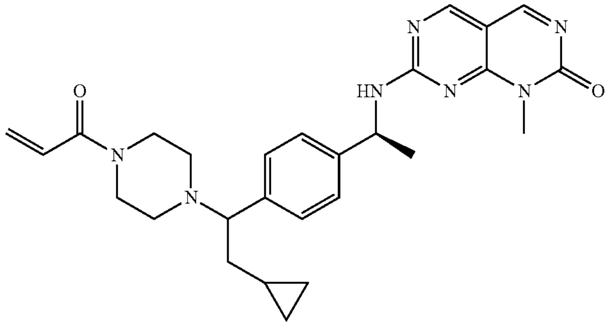 [SMILES: C=CC(=O)N1CCN(C(CC2CC2)c2ccc([C@H](C)Nc3ncc4cnc(=O)n(C)c4n3)cc2)CC1] | 488 |

TABLE 5-continued
| Compounds 86-138 | | |
|---|---|---|
| Compound | Structural formula | MS: $[M + H]^+$ |
| 118 | 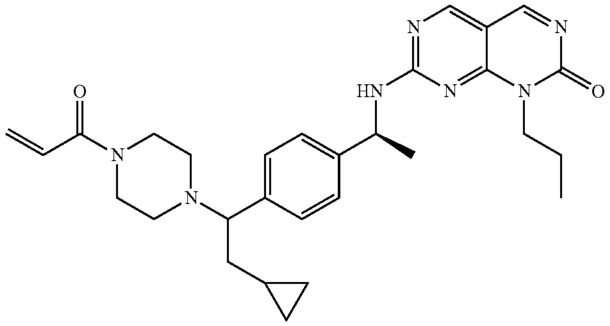 [SMILES: C=CC(=O)N1CCN(C(CC2CC2)c2ccc([C@H](C)Nc3ncc4cnc(=O)n(CCC)c4n3)cc2)CC1] | 516 |
| 119 | 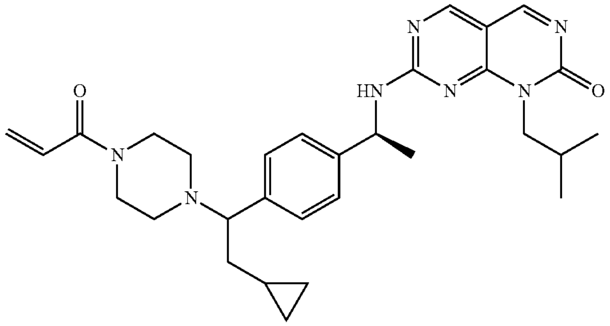 [SMILES: C=CC(=O)N1CCN(C(CC2CC2)c2ccc([C@H](C)Nc3ncc4cnc(=O)n(CC(C)C)c4n3)cc2)CC1] | 530 |
| 120 | 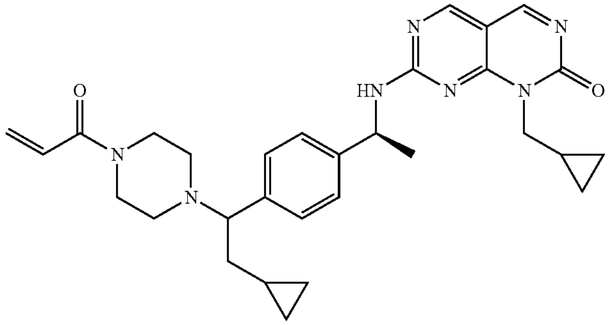 [SMILES: C=CC(=O)N1CCN(C(CC2CC2)c2ccc([C@H](C)Nc3ncc4cnc(=O)n(CC5CC5)c4n3)cc2)CC1] | 528 |
| 121 | 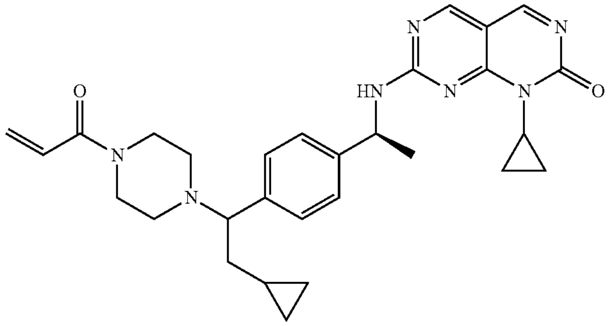 [SMILES: C=CC(=O)N1CCN(C(CC2CC2)c2ccc([C@H](C)Nc3ncc4cnc(=O)n(C5CC5)c4n3)cc2)CC1] | 514 |

TABLE 5-continued
| Compounds 86-138 | | |
|---|---|---|
| Compound | Structural formula | MS: [M + H]$^+$ |
| 122 | 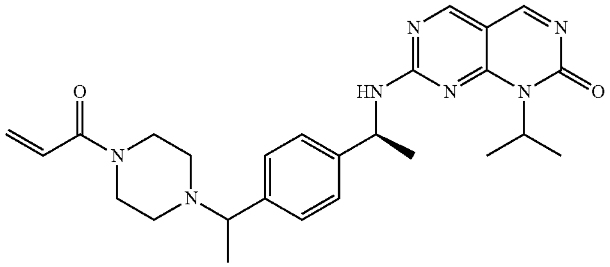 [SMILES: C=CC(=O)N1CCN(C(C)c2ccc([C@H](C)Nc3ncc4cnc(=O)n(C(C)C)c4n3)cc2)CC1] | 476 |
| 123 | 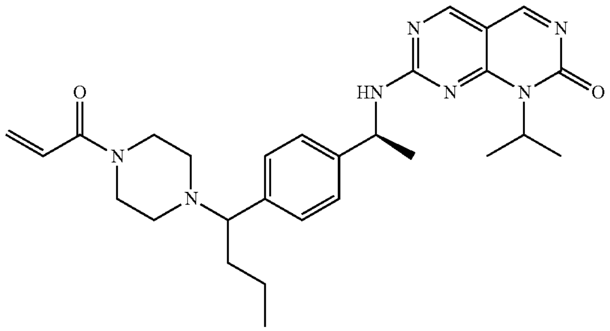 [SMILES: C=CC(=O)N1CCN(C(CCC)c2ccc([C@H](C)Nc3ncc4cnc(=O)n(C(C)C)c4n3)cc2)CC1] | 504 |
| 124 | 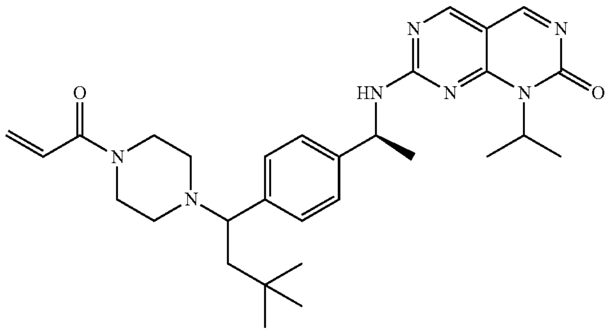 [SMILES: C=CC(=O)N1CCN(C(CC(C)(C)C)c2ccc([C@H](C)Nc3ncc4cnc(=O)n(C(C)C)c4n3)cc2)CC1] | 532 |
| 125 | 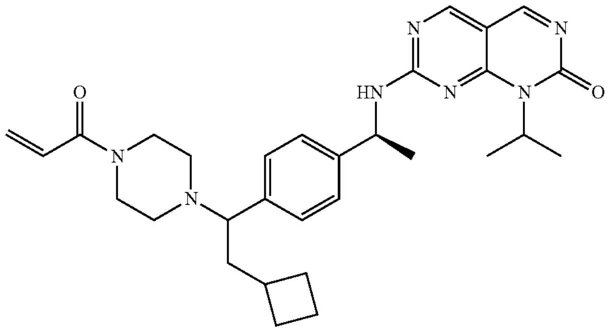 [SMILES: C=CC(=O)N1CCN(C(CC2CCC2)c2ccc([C@H](C)Nc3ncc4cnc(=O)n(C(C)C)c4n3)cc2)CC1] | 530 |

TABLE 5-continued
| Compounds 86-138 | | |
|---|---|---|
| Compound | Structural formula | MS: [M + H]+ |
| 126 | 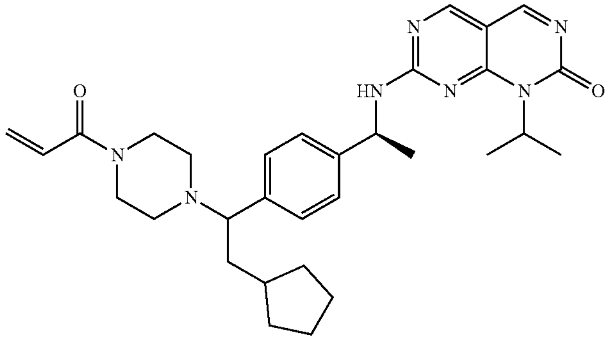 [SMILES: C=CC(=O)N1CCN(C(CC2CCCC2)c2ccc([C@H](C)Nc3ncc4cnc(=O)n(C(C)C)c4n3)cc2)CC1] | 544 |
| 127 | 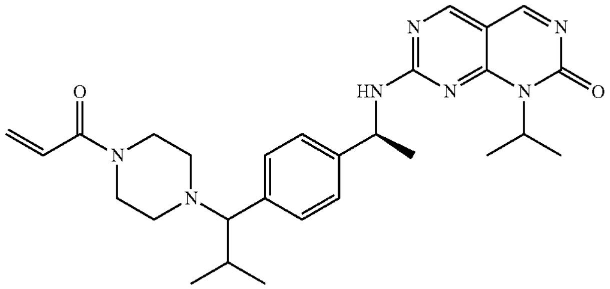 [SMILES: C=CC(=O)N1CCN(C(c2ccc([C@H](C)Nc3ncc4cnc(=O)n(C(C)C)c4n3)cc2)C(C)C)CC1] | 504 |
| 128 | 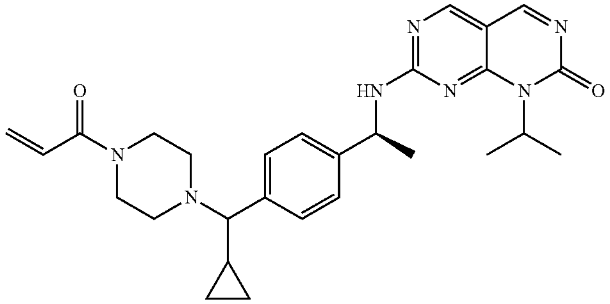 [SMILES: C=CC(=O)N1CCN(C(c2ccc([C@H](C)Nc3ncc4cnc(=O)n(C(C)C)c4n3)cc2)C2CC2)CC1] | 502 |
| 129 | 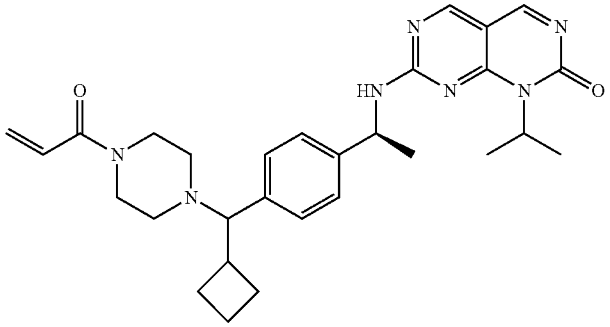 [SMILES: C=CC(=O)N1CCN(C(c2ccc([C@H](C)Nc3ncc4cnc(=O)n(C(C)C)c4n3)cc2)C2CCC2)CC1] | 516 |

TABLE 5-continued
| Compounds 86-138 | | |
|---|---|---|
| Compound | Structural formula | MS: [M + H]+ |
| 130 | 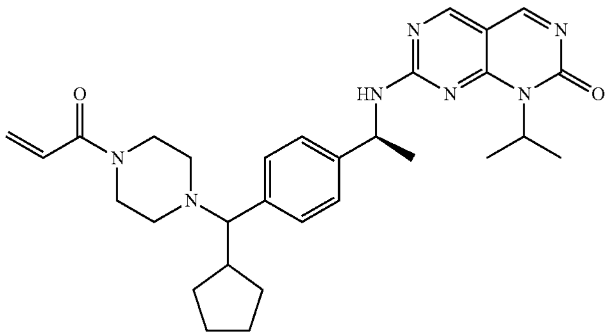 [SMILES: C=CC(=O)N1CCN(C(c2ccc([C@H](C)Nc3ncc4cnc(=O)n(C(C)C)c4n3)cc2)C2CCCC2)CC1] | 530 |
| 131 | 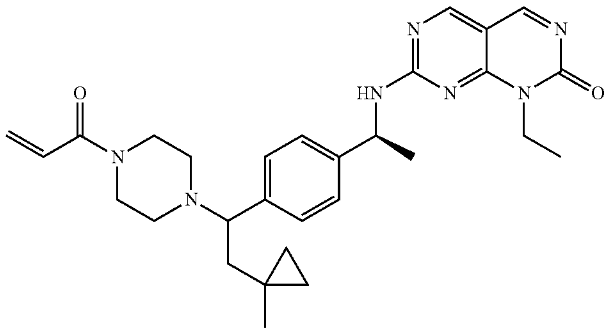 [SMILES: C=CC(=O)N1CCN(C(CC2(C)CC2)c2ccc([C@H](C)Nc3ncc4cnc(=O)n(CC)c4n3)cc2)CC1] | 516 |
| 132 | 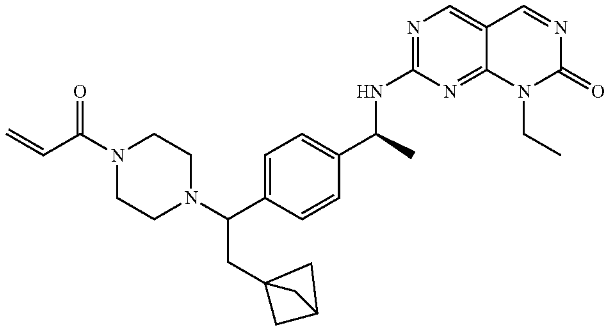 [SMILES: C=CC(=O)N1CCN(C(CC23CC(C2)C3)c2ccc([C@H](C)Nc3ncc4cnc(=O)n(CC)c4n3)cc2)CC1] | 528 |
| 133 | 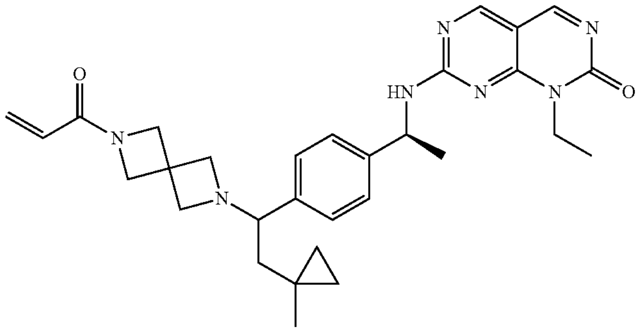 [SMILES: C=CC(=O)N1CC2(C1)CN(C(CC1(C)CC1)c1ccc([C@H](C)Nc3ncc4cnc(=O)n(CC)c4n3)cc1)C2] | 528 |

TABLE 5-continued
| Compound | Structural formula | MS: [M + H]+ |
|---|---|---|
| Compounds 86-138 | | |
| 134 | 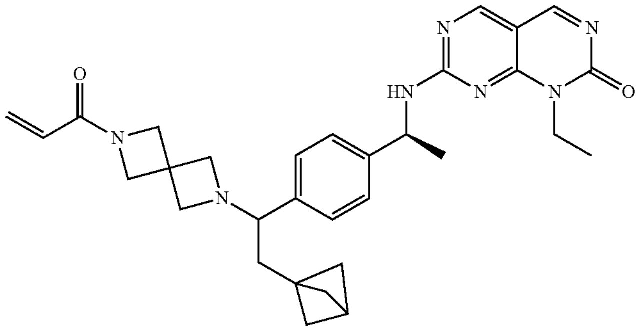 [SMILES: C=CC(=O)N1CC2(C1)CN(C(CC13CC(C1)C3)c1ccc([C@H](C)Nc3ncc4cnc(=O)n(CC)c4n3)cc1)C2] | 540 |
| 135 | 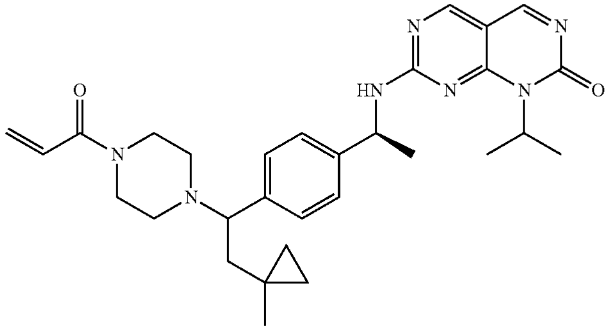 [SMILES: C=CC(=O)N1CCN(C(CC2(C)CC2)c2ccc([C@H](C)Nc3ncc4cnc(=O)n(C(C)C)c4n3)cc2)CC1] | 530 |
| 136 | 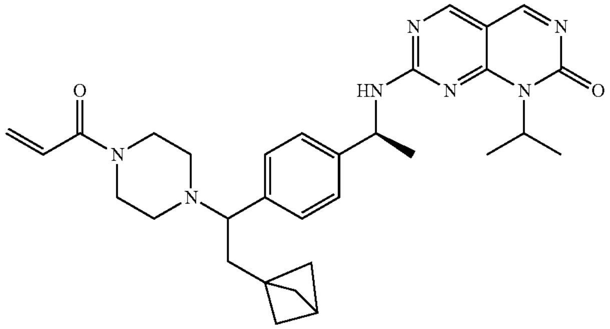 [SMILES: C=CC(=O)N1CCN(C(CC23CC(C2)C3)c2ccc([C@H](C)Nc3ncc4cnc(=O)n(C(C)C)c4n3)cc2)CC1] | 542 |
| 137 | 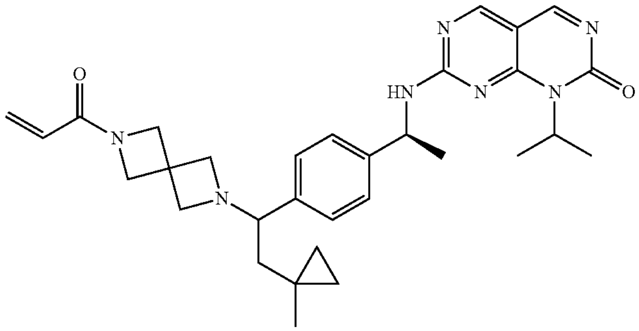 [SMILES: C=CC(=O)N1CC2(C1)CN(C(CC1(C)CC1)c1ccc([C@H](C)Nc3ncc4cnc(=O)n(C(C)C)c4n3)cc1)C2] | 542 |

TABLE 5-continued

| Compounds 86-138 | | |
|---|---|---|
| Compound | Structural formula | MS: [M + H]+ |
| 138 | 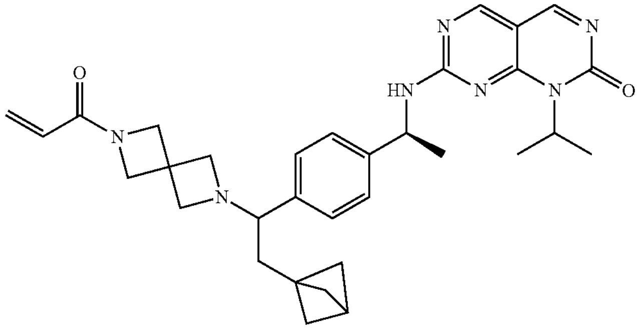 [SMILES: C=CC(=O)N1CC2(C1)CN(C(CC13CC(C1)C3)c1ccc([C@H](C)Nc3ncc4cnc(=O)n(C(C)C)c4n3)cc1)C2] | 554 |

Example 160. Preparation of Chiral Isomers of the Compounds Disclosed Herein

The compound of the present invention comprises one or more chiral centers, and various optically pure isomers of the compound disclosed herein may be prepared by using optically pure intermediates B1-B64 and different A1-A15 fragments as starting materials. Alternatively, optically pure isomers of the compound disclosed herein may be prepared by using chiral HPLC or achiral HPLC.

Compound 1 disclosed herein may be obtained as two optically pure isomers 1-1 and 1-2 of the compound 1 by using the above-described method:

1-1

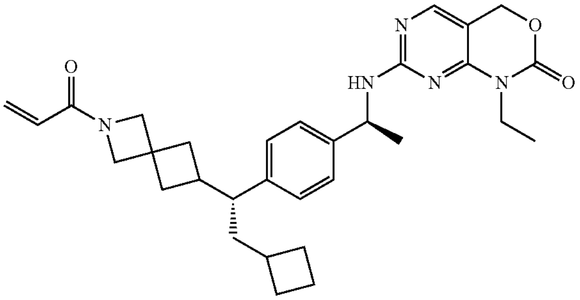

1-2

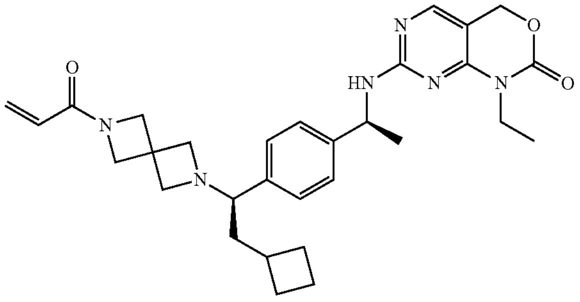

Compounds 36, 66, 70, 72, 85, 114, 116, 139, 147 and 157 were chirally resolved by the same synthesis or preparation method to give chiral isomer pairs 36-1/36-2, 66-1/66-2, 70-1/70-2, 72-1/72-2, 85-1/85-2, 114-1/114-2, 116-1/116-2, 139-1/139-2, 147-1/147-2 and 157-1/157-2, respectively:

36-1

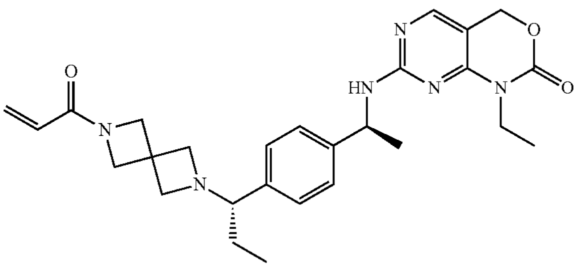

36-2

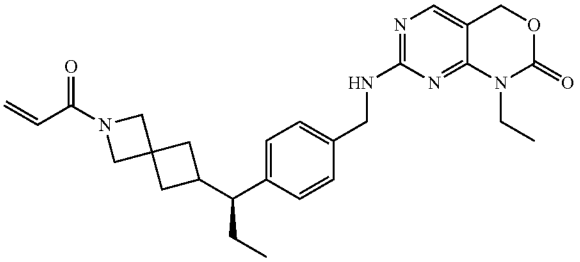

66-1

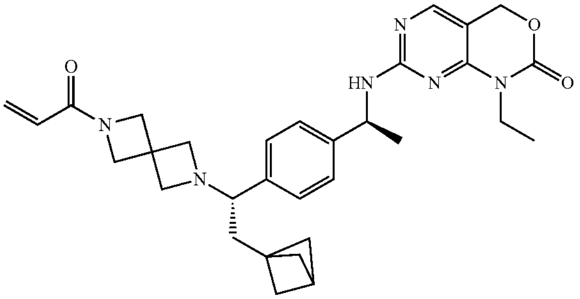

66-2
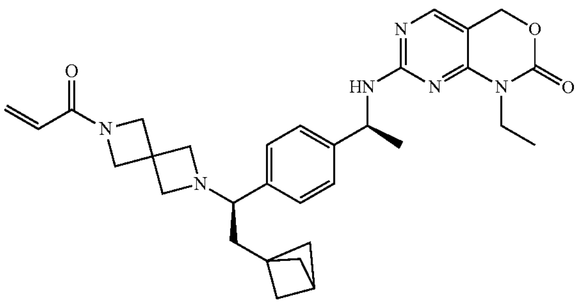
70-1
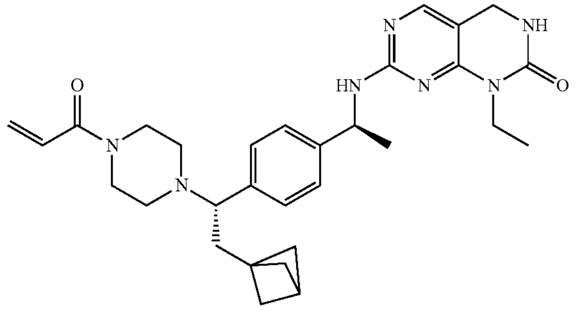
70-2
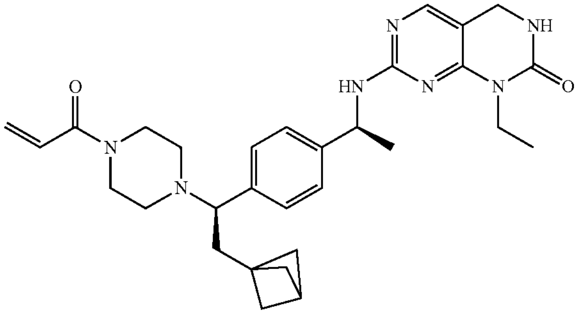
72-1
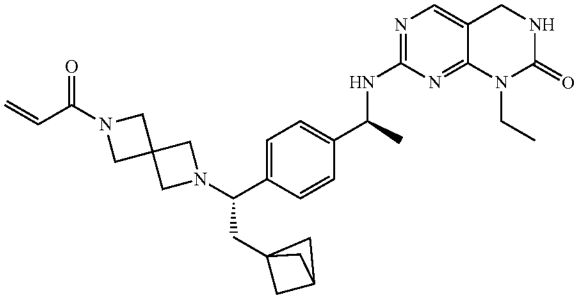
72-2
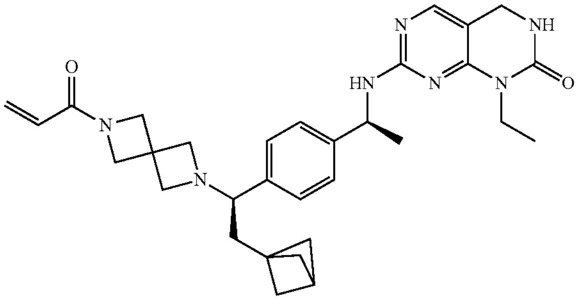
85-1
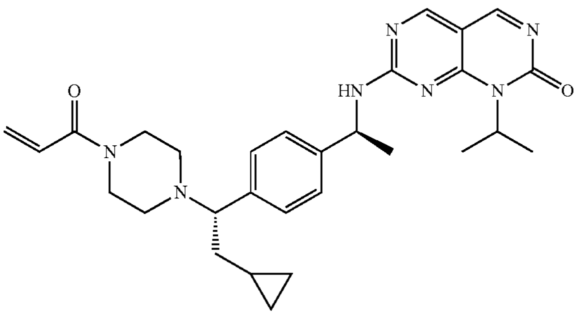
85-2
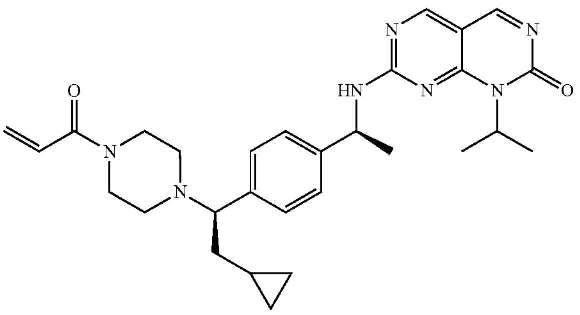
114-1
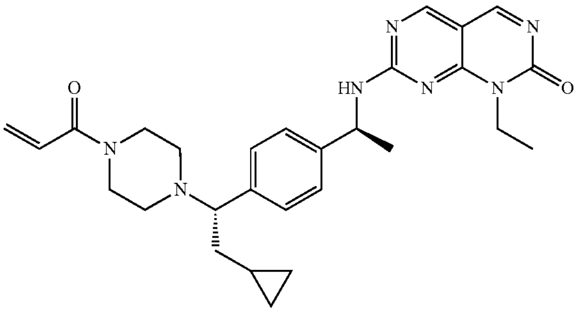
114-2
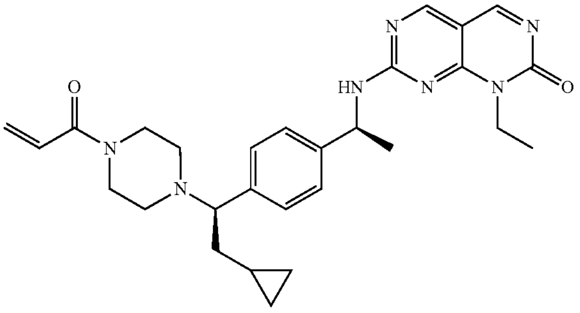
116-1
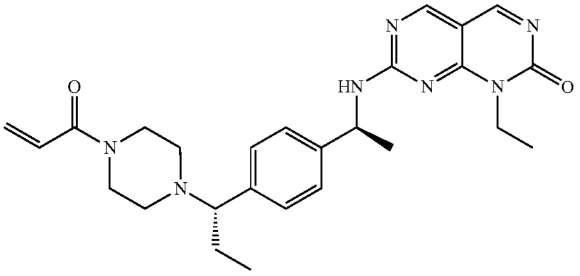

-continued 116-2

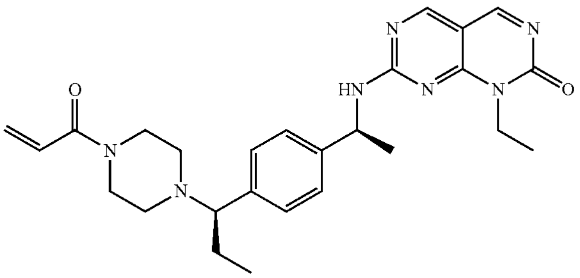

139-1

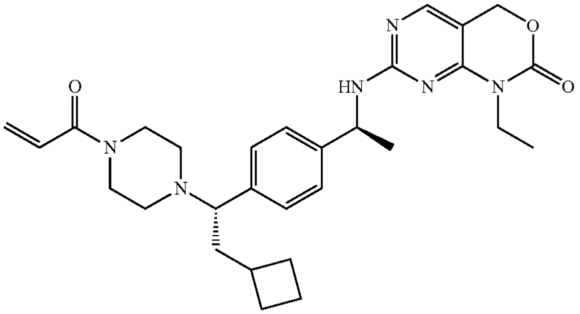

139-2

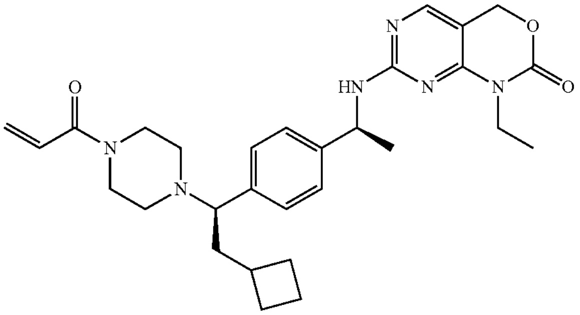

147-1

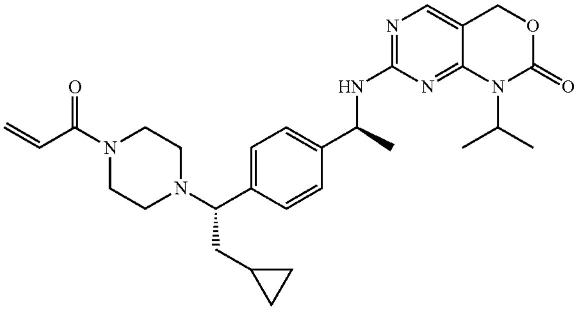

147-2

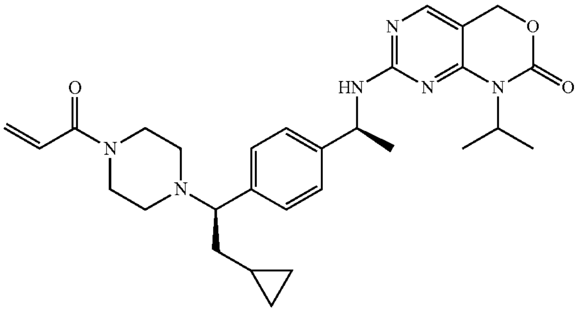

-continued 157-1

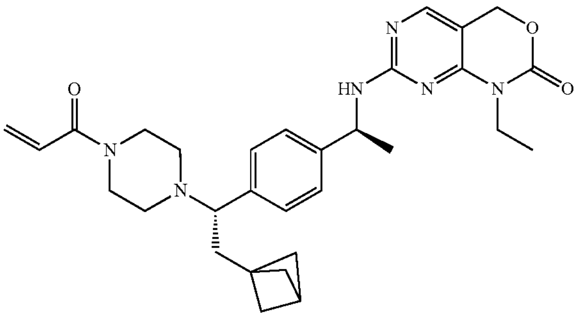

157-2

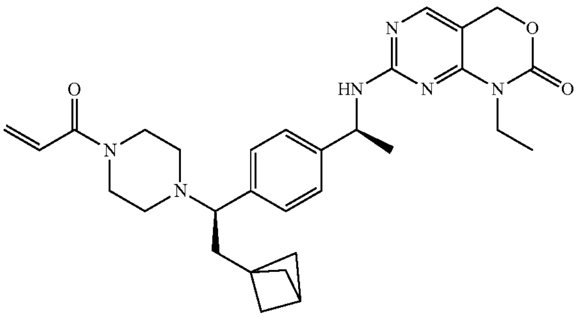

Other compounds of the present invention may also be prepared by similar synthesis or preparation methods to give their corresponding chiral isomers.

Example 161. Detection of 2-HG in Supernatant of U87-IDH R132C Cells

U87 cells overexpressing the IDH R132C mutation were seeded in a 48-well plate at 50,000 cells/well. After the cells were incubated overnight for adhesion, the supernatant was removed. The cell culture media containing serially diluted compounds were added, and the cells were incubated for 72 h. After 72 h, the cultures were collected and diluted 10-fold with water, and acetonitrile was added to extract the metabolites. The 2-HG content in the cultures was analyzed by LC-MS-MS, and the percentage inhibition of compounds on 2-HG in the supernatant was calculated as compared with the control.

TABLE 6

Inhibition rate of compounds on 2-HG in the supernatant of U87-IDH R132C cells

| Compound | Inhibition rate | | | Compound | Inhibition rate | | |
|---|---|---|---|---|---|---|---|
| | 100 nM | 10 nM | 1 nM | | 100 nM | 10 nM | 1 nM |
| 1 | A | A | C | 11 | A | A | C |
| 14 | A | A | C | 16 | A | B | C |
| 19 | A | A | C | 22 | A | B | D |
| 23 | A | B | C | 24 | A | A | C |
| 25 | A | A | C | 26 | A | B | C |
| 27 | A | B | C | 28 | A | B | D |
| 29 | A | B | D | 30 | A | B | C |
| 31 | A | B | D | 32 | A | C | C |
| 36 | A | A | B | 41 | A | A | C |
| 46 | A | A | B | 47 | A | A | B |
| 53 | A | B | C | 54 | A | B | B |
| 59 | A | B | C | 63 | A | A | C |
| 65 | A | A | C | 66 | A | A | B |

TABLE 6-continued

Inhibition rate of compounds on 2-HG in the supernatant of U87-IDH R132C cells

| Compound | Inhibition rate 100 nM | 10 nM | 1 nM | Compound | Inhibition rate 100 nM | 10 nM | 1 nM |
|---|---|---|---|---|---|---|---|
| 69 | A | A | C | 70 | A | A | B |
| 71 | A | A | C | 72 | A | A | B |
| 79 | A | B | C | 80 | A | B | C |
| 81 | A | B | C | 82 | A | B | C |
| 85 | A | A | B | 86 | A | B | B |
| 106 | A | B | C | 109 | A | B | B |
| 112 | A | A | B | 113 | A | A | B |
| 114 | A | A | B | 115 | A | A | C |
| 116 | A | A | B | 124 | A | B | C |
| 125 | A | B | C | 131 | A | A | B |
| 141 | A | B | C | 143 | A | B | C |
| 146 | A | B | C | 147 | A | A | B |
| 148 | A | B | D | 152 | A | A | C |
| 153 | A | B | C | 156 | A | A | B |
| 157 | A | A | B | 1-1 | A | A | C |
| 1-2 | A | B | C | 36-1 | A | A | B |
| 36-2 | A | B | B | 66-1 | A | A | B |
| 66-2 | A | B | C | 70-1 | A | A | B |
| 70-2 | A | B | B | 72-1 | A | A | B |
| 72-2 | A | B | C | 85-1 | A | A | B |
| 85-2 | A | B | C | 114-1 | A | A | B |
| 114-2 | A | A | C | 116-1 | A | A | B |
| 116-2 | A | B | C | 139-1 | A | A | B |
| 139-2 | A | B | C | 147-1 | A | A | B |
| 147-2 | A | B | C | 157-1 | A | A | B |
| 157-2 | A | B | C | Ivosidenib | B | D | D |
| LY-3410738 | A | A | C | | | | |

A represents an inhibition rate greater than 90%;
B represents an inhibition rate greater than 60% but less than or equal to 90%;
C represents an inhibition rate greater than 30% but less than or equal to 60%;
D represents an inhibition rate less than or equal to 30%.

Example 162. Detection of 2-HG in Tumor Tissues

Nude mice were inoculated subcutaneously with $1\times10^6$ HT1080 cells. When the tumor volume reached 100-150 $mm^3$, the mice were randomly grouped into solvent control group and compounds 1, 70, 79, 85, 96, 139, 157 and LY-3410738 20 mg/kg groups. The tumors were collected three days and seven days after continuous administration, weighed, digested with a digestion solution and then homogenized. The level of 2-HG in the tumor tissues were determined by LC-MS-MS. The percentage inhibition of compounds on 2-HG in tumor tissues was calculated as compared with the control.

TABLE 7

Inhibition rate of compounds on 2-HG in HT1080 tumor tissues

| Compound | 1 | 70 | 79 | 85 | 96 | 139 | 157 | LY-3410738 |
|---|---|---|---|---|---|---|---|---|
| 3 days | 54 ± 18% | 62 ± 8% | 50 ± 3% | 57 ± 6% | 29 ± 38% | 57 ± 1.8% | 60 ± 8% | 58 ± 11% |
| 7 days | 95 ± 0.5% | 92 ± 5% | 97 ± 1% | 94 ± 3% | 78 ± 4% | 99 ± 0.4% | 90 ± 7% | 88 ± 12% |

As can be seen from the activity data in the above table, the compounds of general formula (1a) disclosed herein have a novel structure with La group. Compared with the marketed IDH inhibitor ivosidenib, the compounds have stronger activity for inhibiting the level of 2-HG in the supernatant of U87-IDH R132C cells and tumor tissues, indicating that the compounds have stronger ability to inhibit IDH R132C mutant protein. Meanwhile, these compounds have similar or stronger activity compared with LY-3410738 (compound 2 in Patent No. WO2018111707).

The compounds of general formula (1b) of the present invention have a novel parent structure, and compared with the marketed IDH inhibitor ivosidenib, these compounds have stronger activity for reducing the level of the catalytic product 2-HG of IDH R132C mutant protein in the supernatant of U87-IDH R132C cells and tumor tissues, and they also have similar or stronger activity compared with LY-3410738.

Although specific embodiments of the present invention have been described above, it will be appreciated by those skilled in the art that these embodiments are merely illustrative and that many changes or modifications can be made to these embodiments without departing from the principles and spirit of the present invention. The scope of protection of the present invention is therefore defined by the appended claims.

The invention claimed is:

1. A compound of general formula (1a) or a stereoisomer, a crystalline form, a pharmaceutically acceptable salt, a hydrate or a solvate thereof:

(1a)

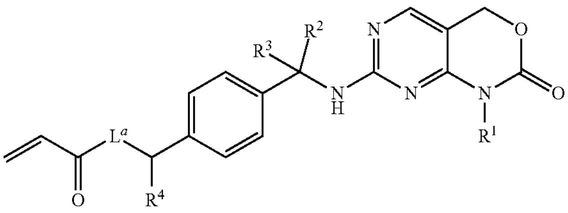

wherein in the general formula (1a):

$L^a$ is the following group:

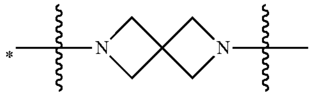

,

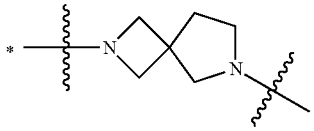

,

-continued

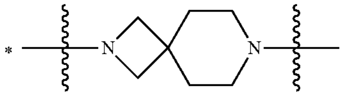

,

-continued
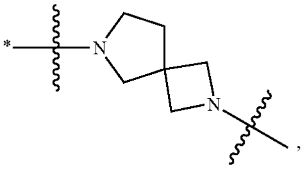
,
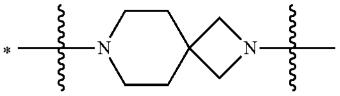
,
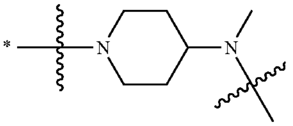
,
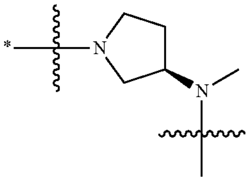
,
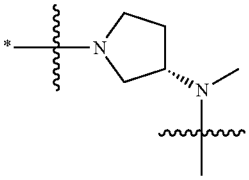
,
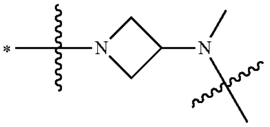
,
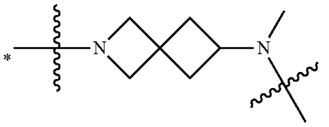
,
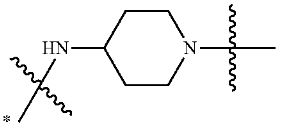
,
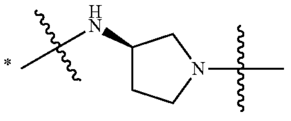
,
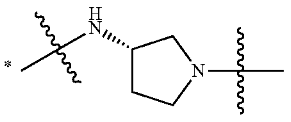
,
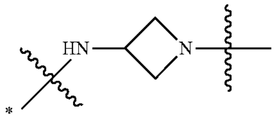
,
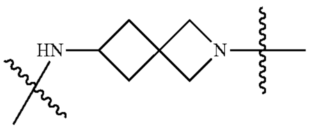
,
-continued
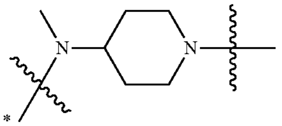
,
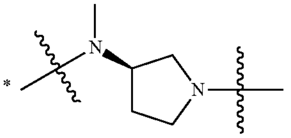
,
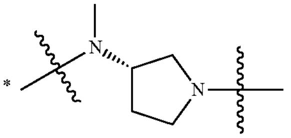
,
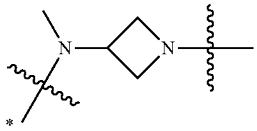
or
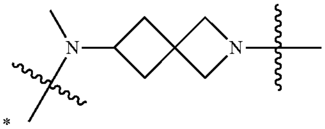
,
wherein "*" denotes a site linked to a carbonyl group;
$R^1$ is Me, Et, —$CH_2CH_2CH_3$, —$CH(CH_3)_2$,
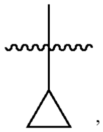
,
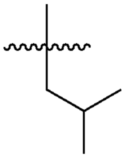
or
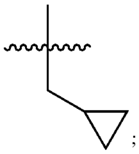
;
$R^2$ and $R^3$ are independently H, Me or Et, or $R^2$ and $R^3$, together with a carbon atom to which $R^2$ and $R^3$ are connected, form
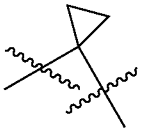
or
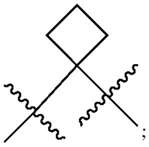
;
and
$R^4$ is Me, Et, —$CH_2CH_2CH_3$, —$CH(CH_3)_2$, —$CH_2CH(CH_3)_2$,
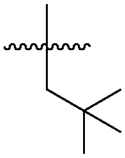
,
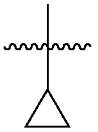
,
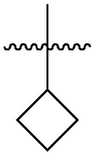
, -continued
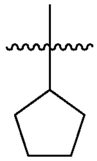,
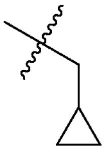,
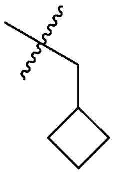,
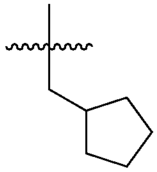,
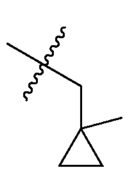,
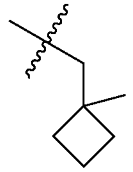,
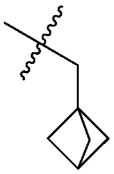,
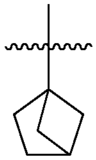,
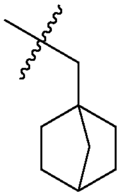 or
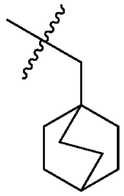.
2. The compound, or the stereoisomer, the crystalline form, the pharmaceutically acceptable salt, the hydrate or the solvate thereof according to claim 1, wherein the compound is selected from the group consisting of:
1
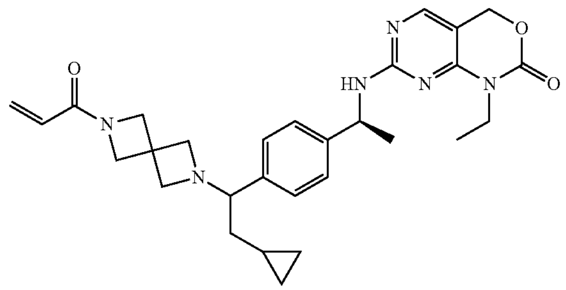
2
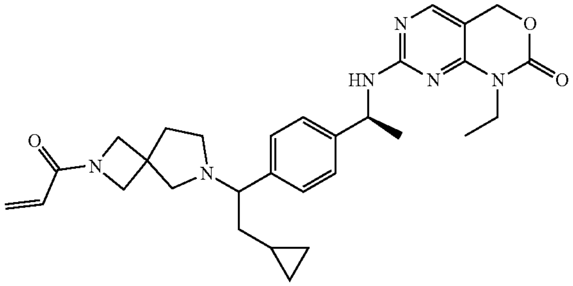
-continued
3
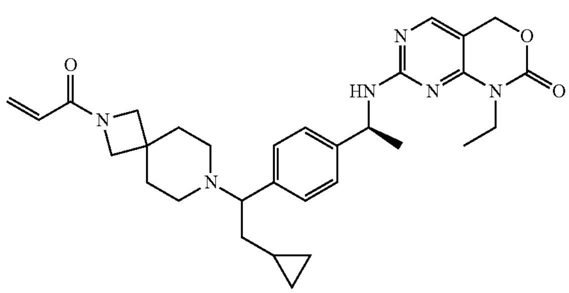
4
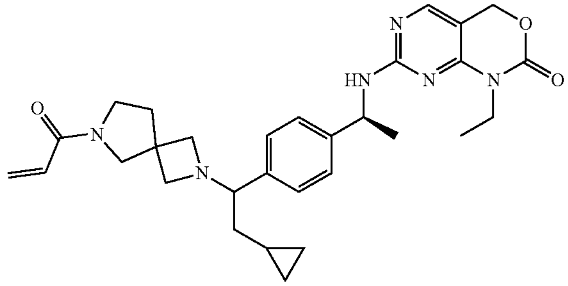
5
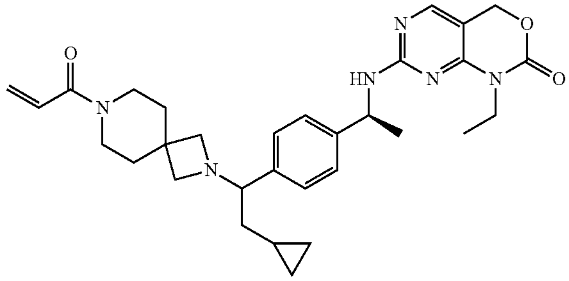
6
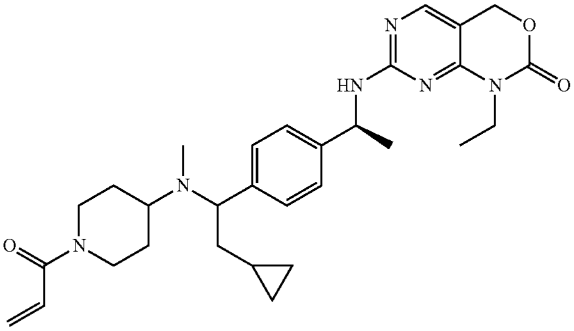
7
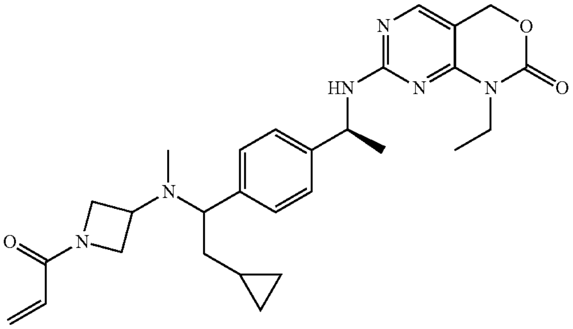

-continued
8
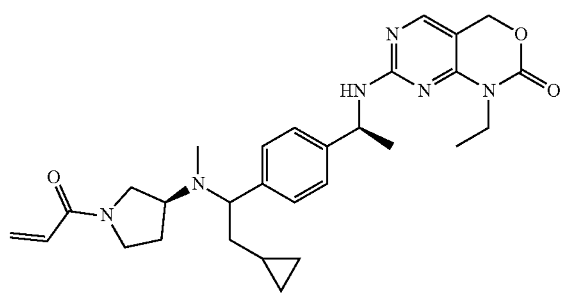
9
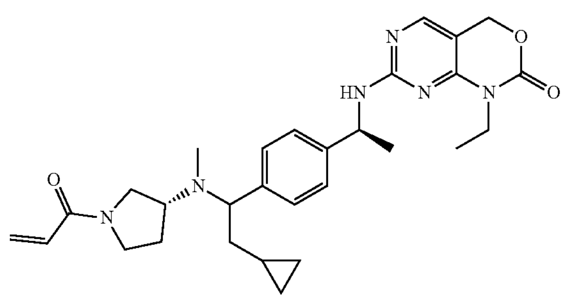
10
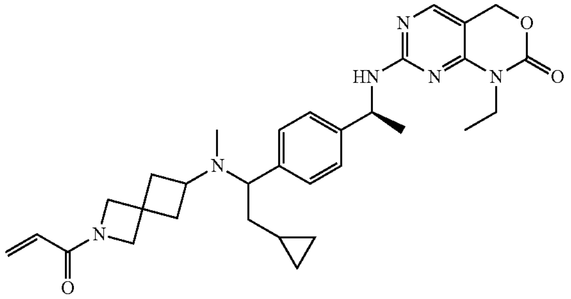
11
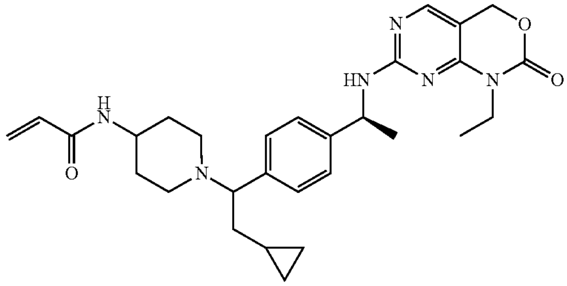
12
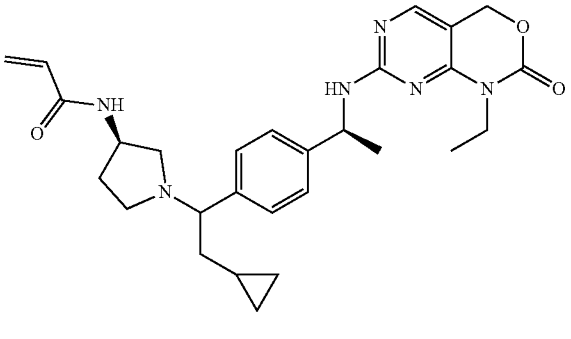
-continued
13
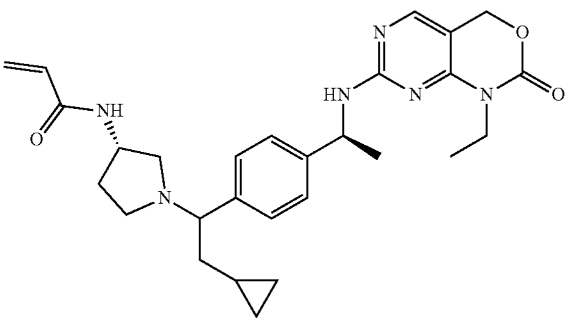
14
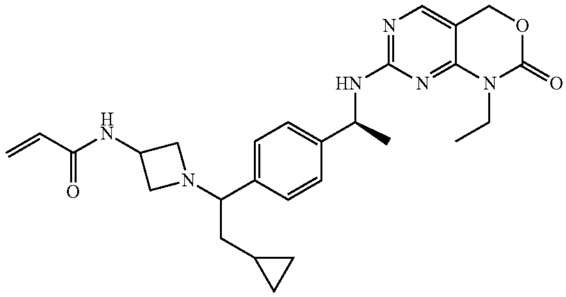
15
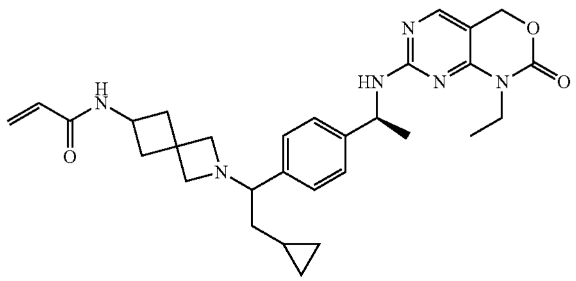
16
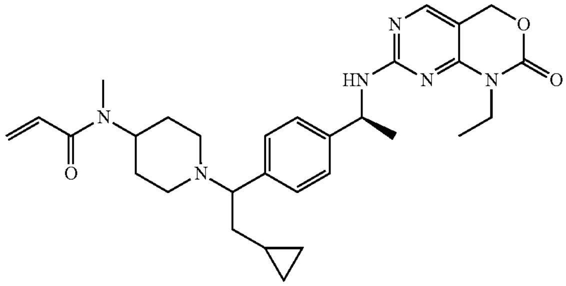
17
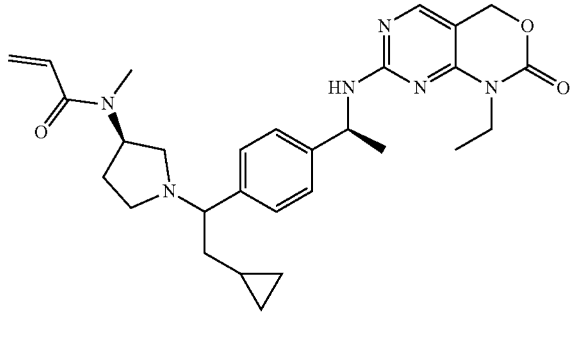

18
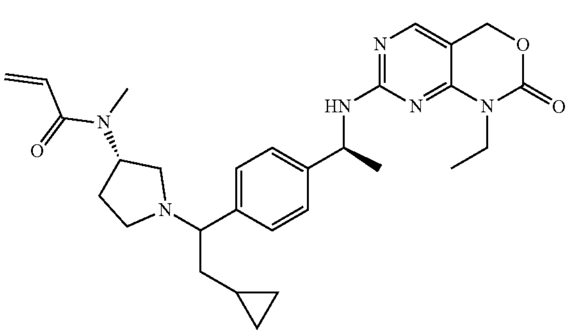
19
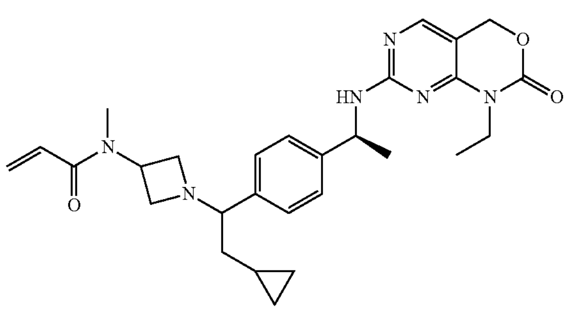
20
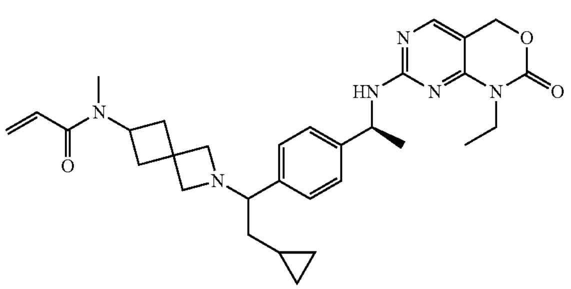
21
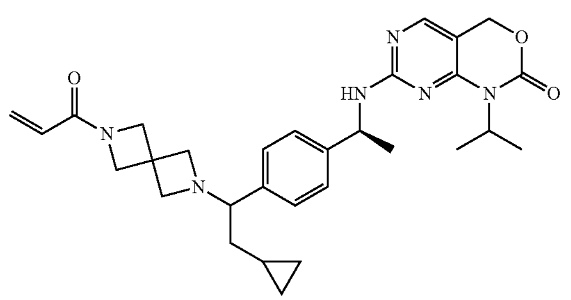
22
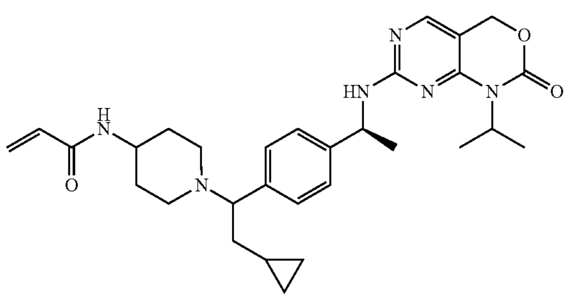
23
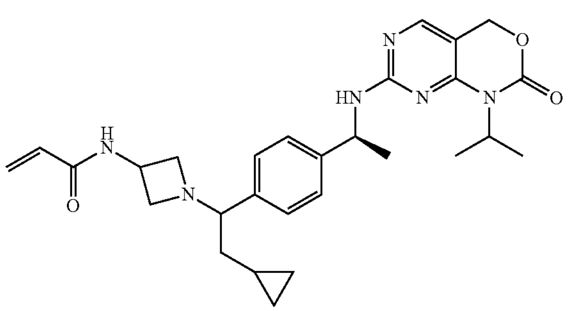
24
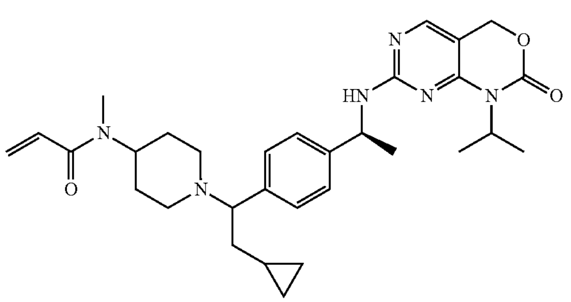
25
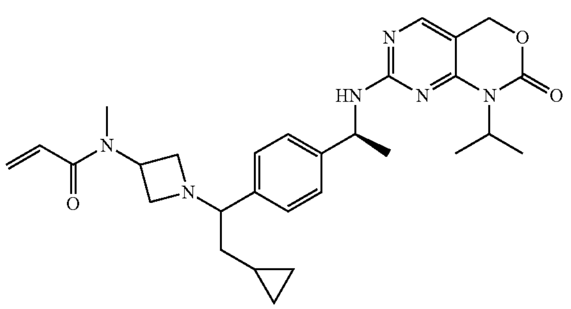
26
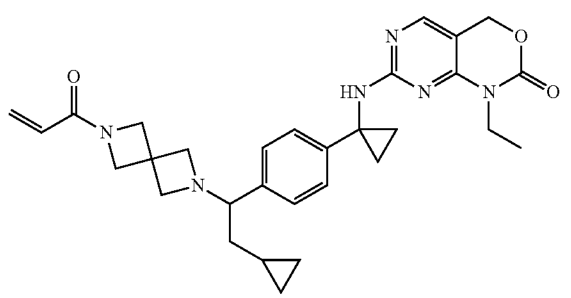
27
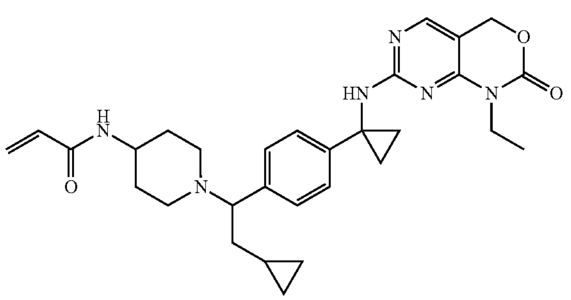

-continued
28
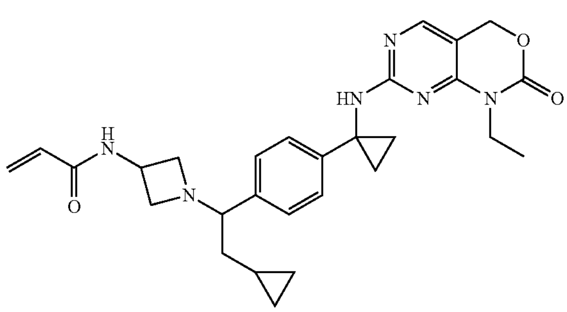
29
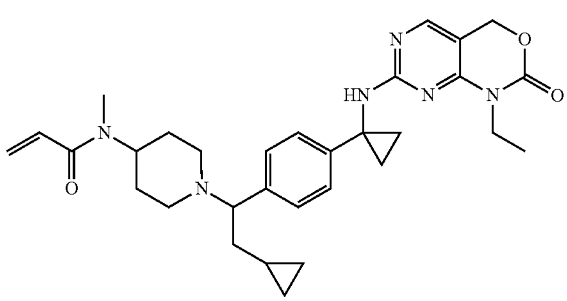
30
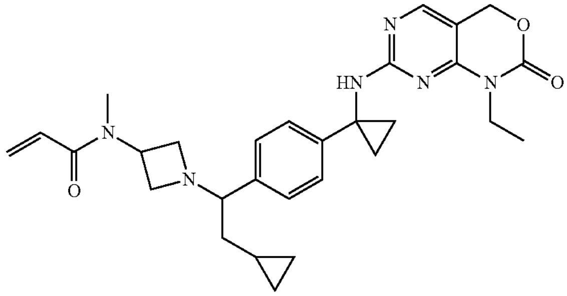
31
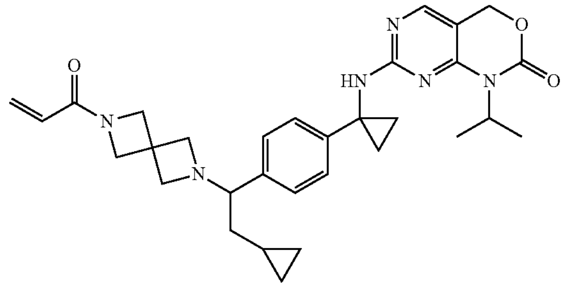
32
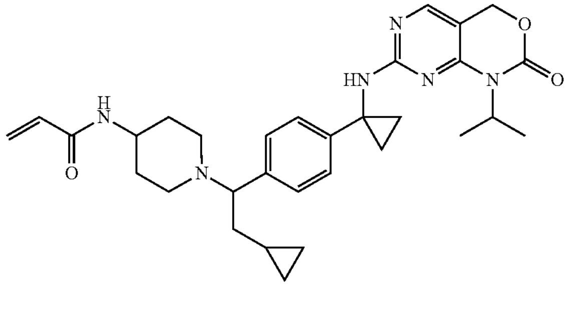
-continued
33
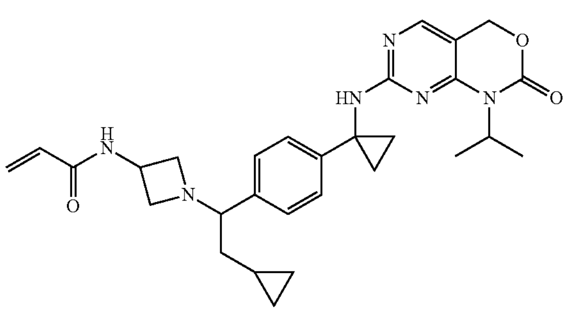
34
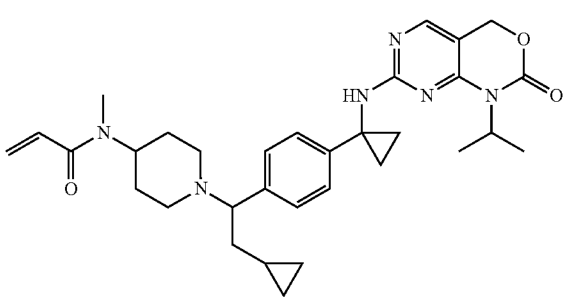
35
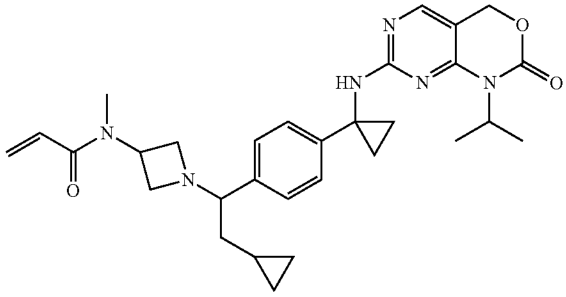
36
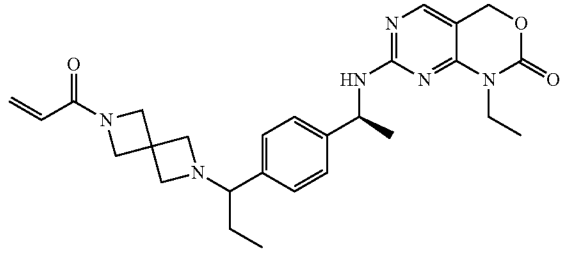
37
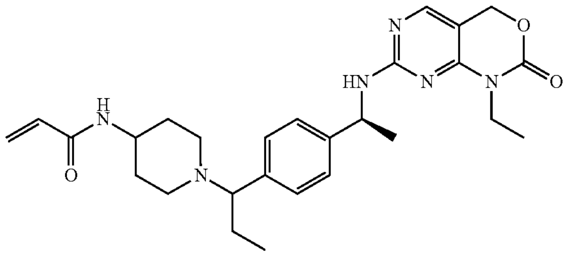

-continued
38
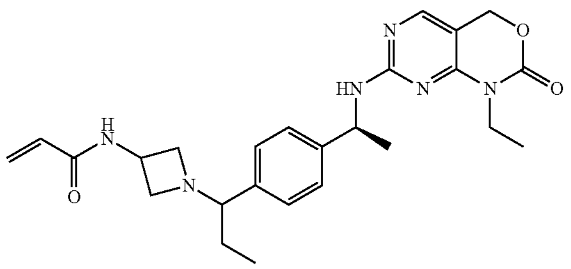
39
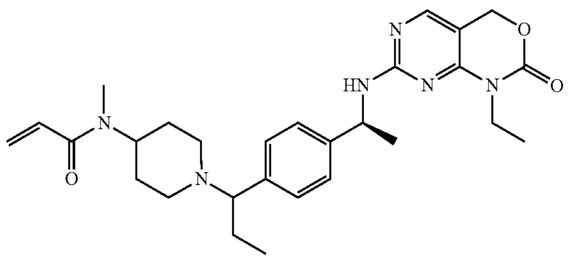
40
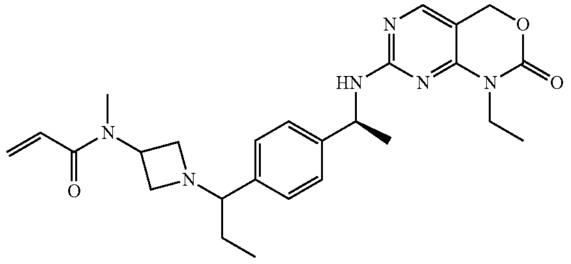
41
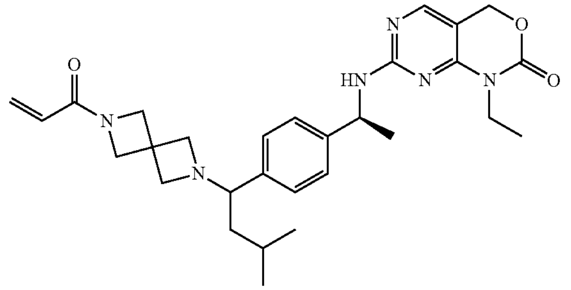
42
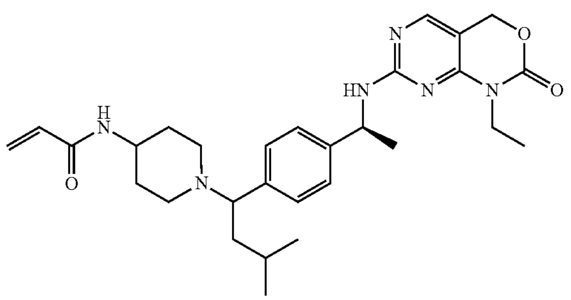
-continued
43
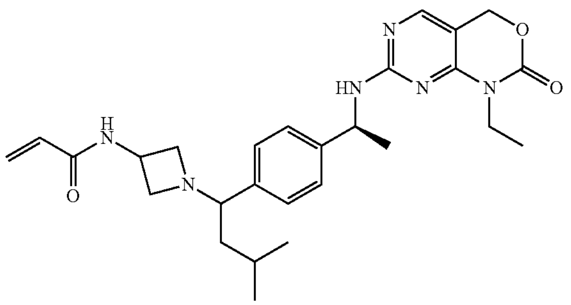
44
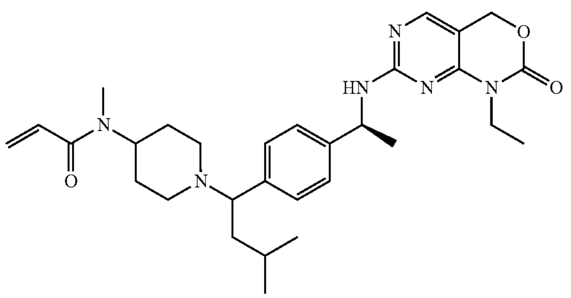
45
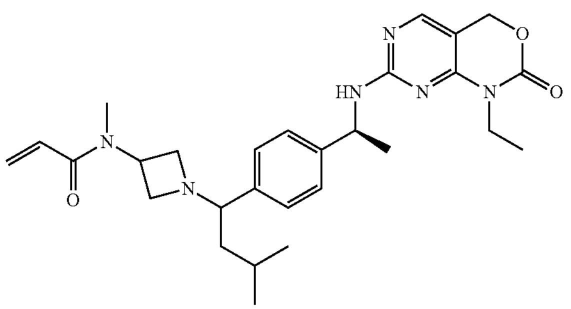
46
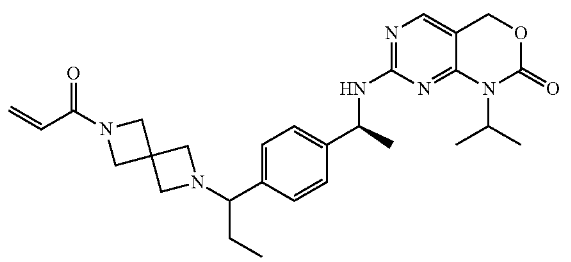
47
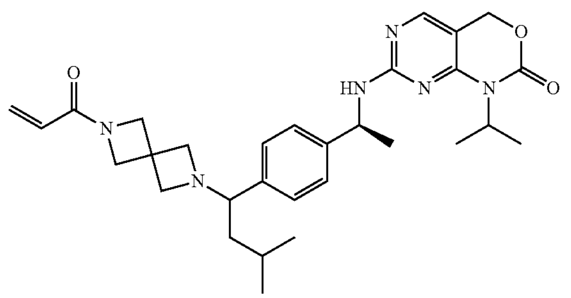

-continued
48
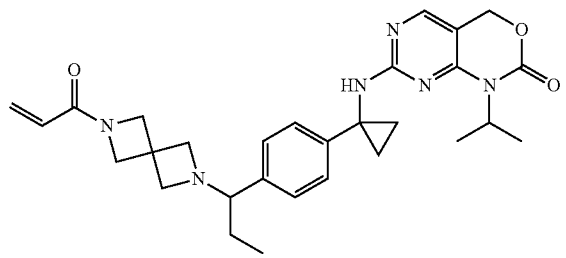
49
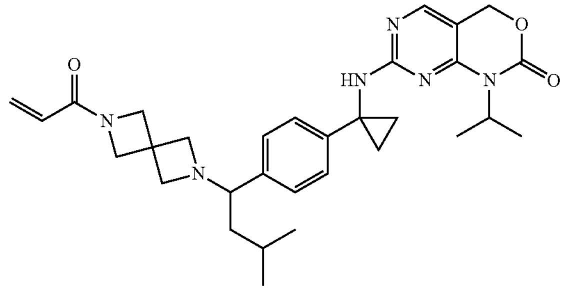
50
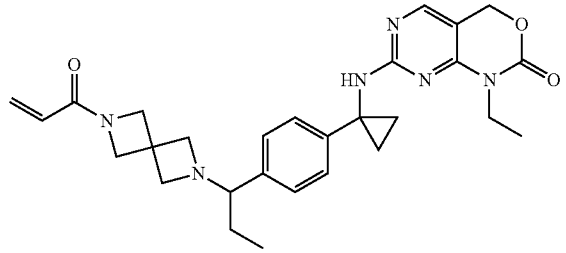
51
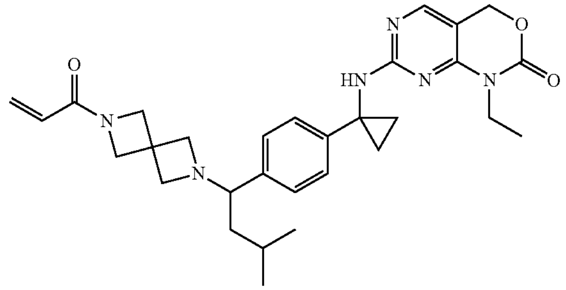
52
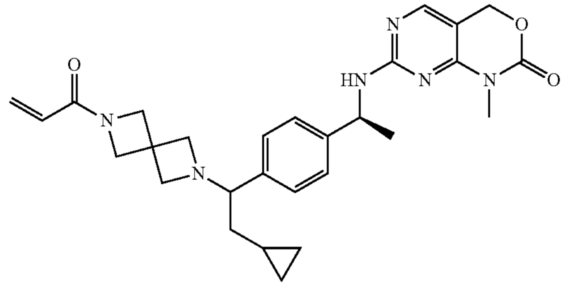
-continued
53
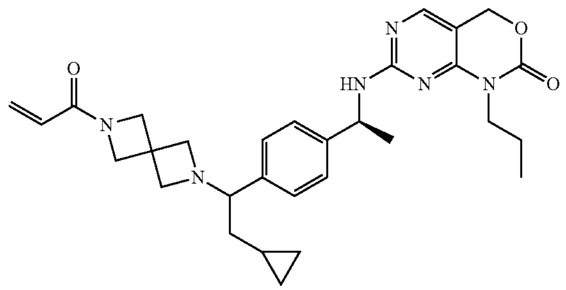
54
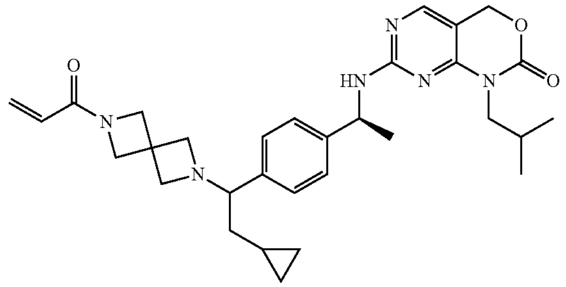
55
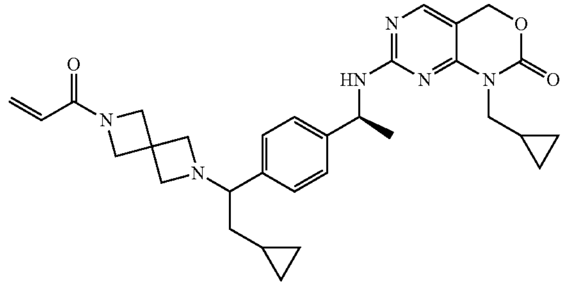
56
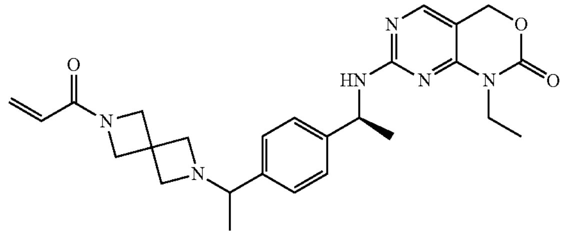
57
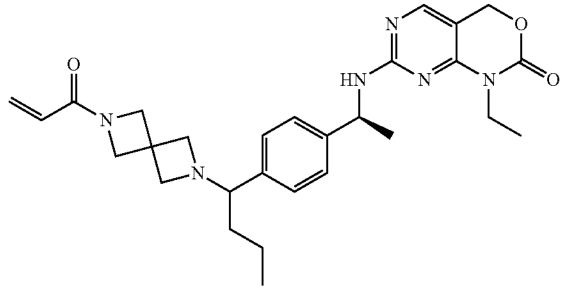

-continued
58
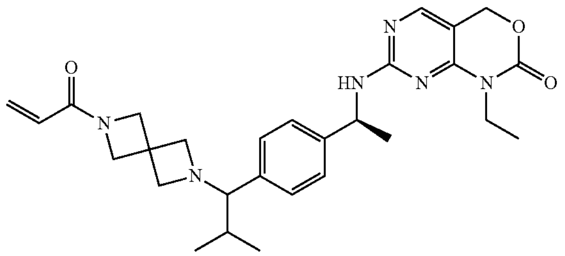
59
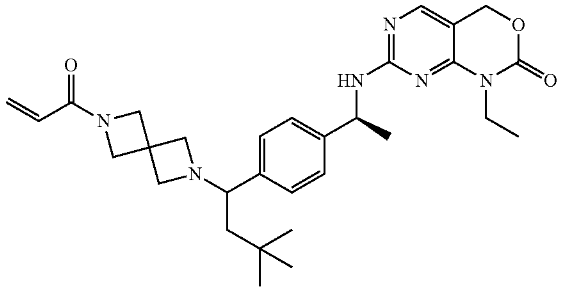
60
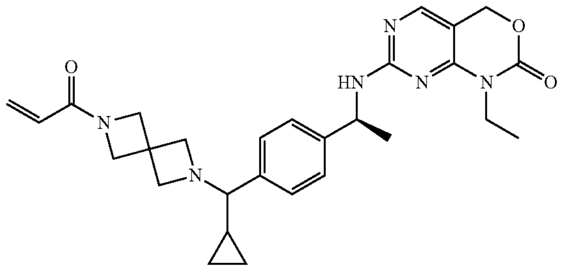
61
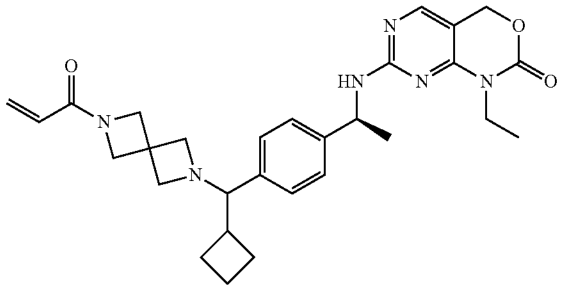
62
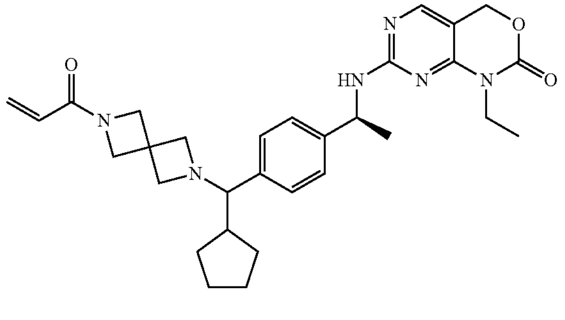
-continued
63
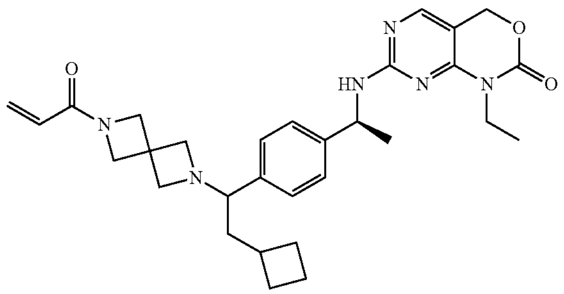
64
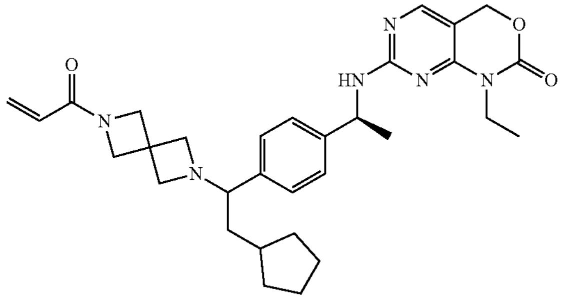
65
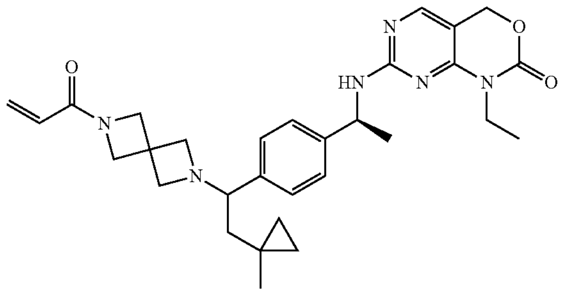
66
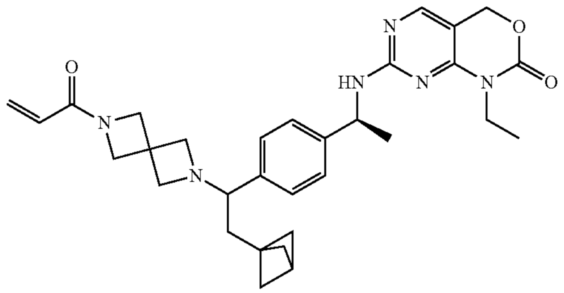
67
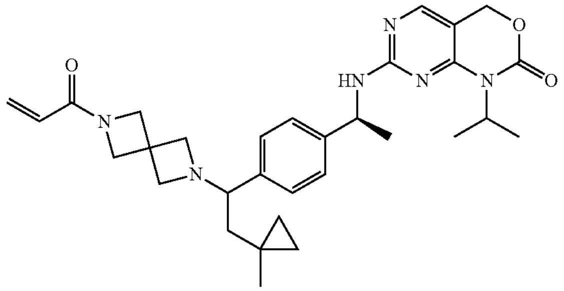
and -continued

68

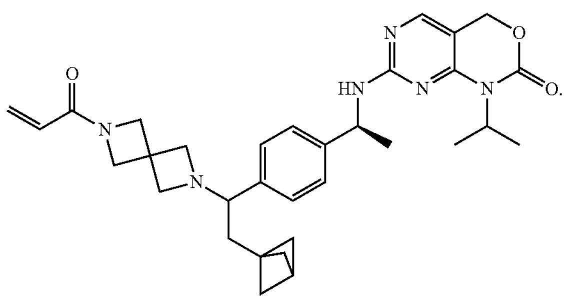

3. A pharmaceutical composition for treating, regulating and/or preventing a disease related to an IDH mutant protein, comprising a pharmaceutically acceptable excipient or carrier, and the compound or the stereoisomer, the crystalline form, the pharmaceutically acceptable salt, the hydrate or the solvate thereof according to claim 1 as an active ingredient.

4. A compound or a stereoisomer, a crystalline form, a pharmaceutically acceptable salt, a hydrate or a solvate thereof, wherein the compound is selected from the group consisting of:

69

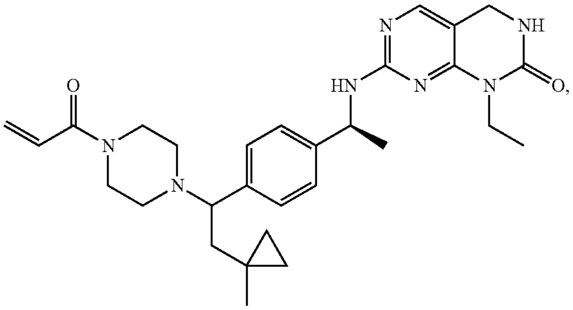

70

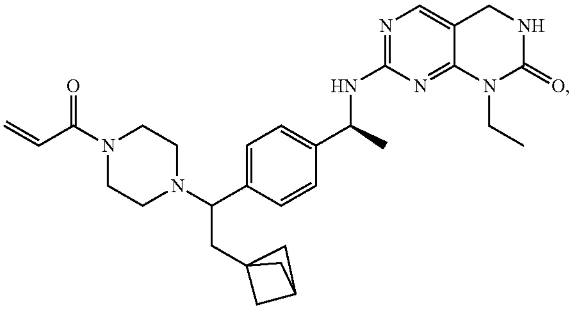

-continued

71

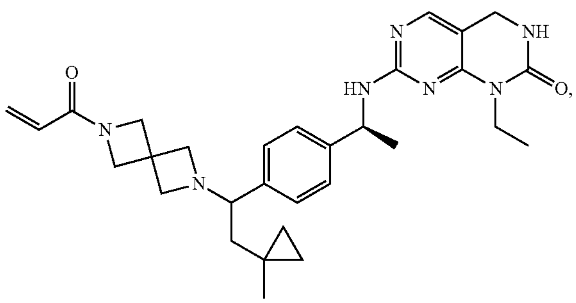

72

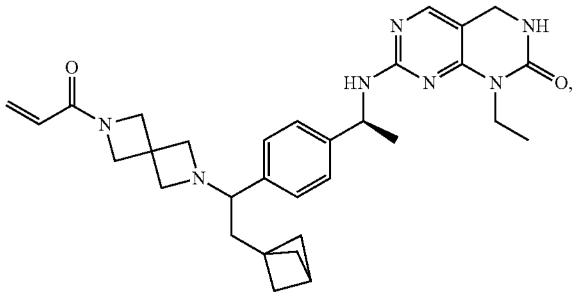

73

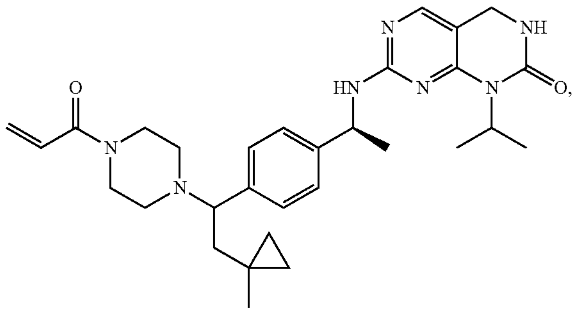

74

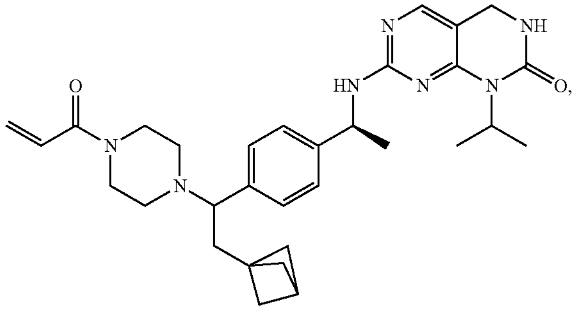

75

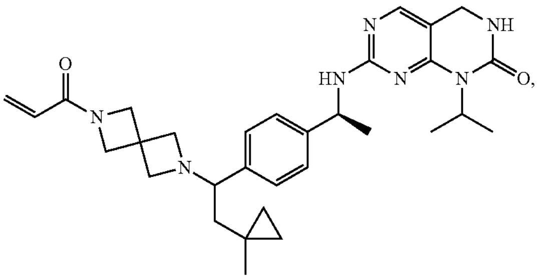

and

-continued
76
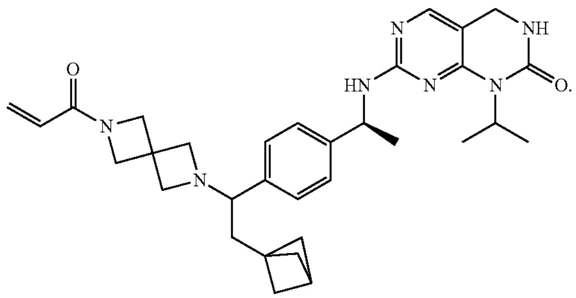
* * * * *